(12) United States Patent
Kanapuram et al.

(10) Patent No.: US 11,419,933 B2
(45) Date of Patent: Aug. 23, 2022

(54) PHARMACEUTICAL COMPOSITION COMPRISING BISPECIFIC ANTIBODY CONSTRUCTS

(71) Applicants: AMGEN INC., Thousand Oaks, CA (US); AMGEN RESEARCH (MUNICH) GMBH, Munich (DE)

(72) Inventors: Sekhar Kanapuram, Thousand Oaks, CA (US); Ramil Latypov, Wellesley, MA (US); Balakumar Thangaraj, Lexington, MA (US); Cornelius Pompe, Munich (DE)

(73) Assignees: AMGEN INC., Thousand Oaks, CA (US); AMGEN RESEARCH (MUNICH) GMBH, Munich (DE)

( * ) Notice: Subject to any disclaimer, the term of this patent is extended or adjusted under 35 U.S.C. 154(b) by 0 days.

(21) Appl. No.: 15/414,723

(22) Filed: Jan. 25, 2017

(65) Prior Publication Data
US 2017/0209571 A1    Jul. 27, 2017

Related U.S. Application Data

(60) Provisional application No. 62/286,552, filed on Jan. 25, 2016.

(51) Int. Cl.
| | | |
|---|---|---|
| *A61K 39/395* | (2006.01) | |
| *C07K 16/28* | (2006.01) | |
| *A61K 9/00* | (2006.01) | |
| *A61K 47/18* | (2017.01) | |
| *A61K 9/16* | (2006.01) | |
| *A61K 9/19* | (2006.01) | |
| *A61K 47/02* | (2006.01) | |
| *A61K 47/10* | (2017.01) | |
| *A61K 47/12* | (2006.01) | |
| *A61K 47/26* | (2006.01) | |
| *A61K 47/40* | (2006.01) | |
| *B01D 61/14* | (2006.01) | |
| *A61K 39/00* | (2006.01) | |

(52) U.S. Cl.
CPC ........ *A61K 39/3955* (2013.01); *A61K 9/0019* (2013.01); *A61K 9/1652* (2013.01); *A61K 9/19* (2013.01); *A61K 47/02* (2013.01); *A61K 47/10* (2013.01); *A61K 47/12* (2013.01); *A61K 47/183* (2013.01); *A61K 47/26* (2013.01); *A61K 47/40* (2013.01); *B01D 61/145* (2013.01); *C07K 16/2803* (2013.01); *C07K 16/2809* (2013.01); *C07K 16/2878* (2013.01); *A61K 2039/505* (2013.01); *B01D 2315/16* (2013.01); *C07K 2317/24* (2013.01); *C07K 2317/31* (2013.01); *C07K 2317/622* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,691,016 A | 9/1972 | Patel et al. |
| 3,773,919 A | 11/1973 | Boswell et al. |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,485,045 A | 11/1984 | Regen |
| 4,486,194 A | 12/1984 | Ferrara |
| 4,487,603 A | 12/1984 | Harris |
| 4,544,545 A | 10/1985 | Ryan et al. |
| 4,596,556 A | 6/1986 | Morrow et al. |
| 4,751,180 A | 6/1988 | Cousens et al. |
| 4,790,824 A | 12/1988 | Morrow et al. |
| 4,935,233 A | 6/1990 | Bell et al. |
| 4,941,880 A | 7/1990 | Burns |
| 5,013,556 A | 5/1991 | Woodle et al. |
| 5,064,413 A | 11/1991 | McKinnon et al. |
| 5,292,658 A | 3/1994 | Cormier et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,418,155 A | 5/1995 | Cormier et al. |
| 5,683,888 A | 11/1997 | Campbell |
| 5,741,668 A | 4/1998 | Ward et al. |
| 5,777,079 A | 7/1998 | Tsien et al. |

(Continued)

FOREIGN PATENT DOCUMENTS

| | | |
|---|---|---|
| EP | 0 036 676 A1 | 9/1981 |
| EP | 0 058 481 A1 | 8/1982 |

(Continued)

OTHER PUBLICATIONS

Serno et al. (Journal of Pharmaceutical Sciences, 2010, p. 1193-1206).*
Friess et al. (Cancer Therapy, 2005, p. 5300-5309).*
Aplin et al., Preparation, properties, and applications of carbohydrate conjugates of proteins and lipids. CRC Crit. Rev. Biochem. 259-306 (1981).
Chalfie et al., Green fluorescent protein as a marker for gene expression. *Science* 263: 802-5 (1994).
Chi et al., Physical stability of proteins in aqueous solution: Mechanism and driving forces in nonnative protein aggregation. *Pharm. Res.* 20(9): 1325-36 (2003).
Chothia et al., Canonical structures for the hypervariable regions of immunoglobulins. *J. Mol. Biol.*196: 901-17 (1987).

(Continued)

*Primary Examiner* — Agnieszka Boesen
(74) *Attorney, Agent, or Firm* — Marshall, Gerstein & Borun LLP

(57) ABSTRACT

The present invention provides novel and stable pharmaceutical compositions comprising bispecific single chain antibody constructs, cyclodextrins and a buffer.

19 Claims, 20 Drawing Sheets

Specification includes a Sequence Listing.

(56) References Cited

U.S. PATENT DOCUMENTS

| | | | |
|---|---|---|---|
| 5,804,387 A | 9/1998 | Cormack et al. | |
| 5,874,304 A | 2/1999 | Zolotukhin et al. | |
| 5,876,995 A | 3/1999 | Bryan | |
| 2010/0150918 A1* | 6/2010 | Kufer | C07K 14/7051 424/133.1 |
| 2011/0275787 A1* | 11/2011 | Kufer | C07K 16/2803 530/324 |

FOREIGN PATENT DOCUMENTS

| | | | |
|---|---|---|---|
| EP | 0 088 046 A2 | 9/1983 | |
| EP | 0 133 988 A2 | 3/1985 | |
| EP | 0 143 949 A1 | 6/1985 | |
| JP | 2000-226336 A | 8/2000 | |
| JP | 2006-517540 A | 7/2006 | |
| JP | 2007-537714 A | 12/2007 | |
| JP | 2014-500879 A | 1/2014 | |
| WO | WO-1987/05330 A1 | 9/1987 | |
| WO | WO-1988/09344 A1 | 12/1988 | |
| WO | WO-1992/15673 A1 | 9/1992 | |
| WO | WO-1995/07463 A1 | 3/1995 | |
| WO | WO-1997/38731 A1 | 10/1997 | |
| WO | WO-1998/14605 A1 | 4/1998 | |
| WO | WO-1998/26277 A1 | 6/1998 | |
| WO | WO-1999/49019 A2 | 9/1999 | |
| WO | WO-2004/064787 A2 | 8/2004 | |
| WO | WO-2004/106381 A1 | 12/2004 | |
| WO | WO-2005/040220 A1 | 5/2005 | |
| WO | WO-2012/066058 A1 | 5/2012 | |
| WO | WO-2013/072406 A1 | 5/2013 | |
| WO | WO 2014140368 * | 9/2014 | A61K 47/48 |
| WO | WO-2015/036583 A2 | 3/2015 | |
| WO | WO-2015/142675 A2 | 9/2015 | |
| WO | WO-2016/004108 A2 | 1/2016 | |

OTHER PUBLICATIONS

Chothia et al., Conformation of immunoglobulin hypervariable regions. *Nature* 342: 877-83 (1989).

Duskin et al., Relationship of the structure and biological activity of the natural homologues of tunicamycin. *J. Biol. Chem.* 257(6): 3105-9 (1982).

Edge et al., Deglycosylation of glycoproteins by trifluoromethanesulfonic acid. *Anal. Biochem.* 118: 131-7 (1981).

Eppstein et al., Biological activity of liposome-encapsulated murine interferon γ is mediated by a cell membrane receptor. *Proc. Natl. Acad. Sci. USA* 82: 3688-92 (1985).

Fanslow et al., Structural characteristics of CD40 ligand that determine biological function. *Semin. Immunol.* 6:267-78 (1994).

Gabizon et al., Pharmacokinetics and tissue distribution of doxorubicin encapsulated in stable liposomes with long circulation times. *J. Natl. Cancer Inst.* 8: 1484-8 (1989).

Hakimuddin et al., A chemical method for the deglycosylation of proteins. *Arch. Biochem. Biophys.* 259:52-7 (1987).

Heim et al., Engineering green fluorescent protein for improved brightness, longer wavelengths and fluorescence resonance energy transfer. *Curr. Biol.* 6: 178-82 (1996).

Hoppe et al., A parallel three stranded alpha-helical bundle at the nucleation site of collagen triple-helix formation. *FEBS Lett.* 344: 191-5 (1994).

Hwang et al., Hepatic uptake and degradation of unilamellar sphingomyelin/cholecterol liposomes: A kinetic study. *Proc. Natl. Acad. Sci. USA* 77: 4030-4 (1980).

Ichiki et al., Regulation of the expression of human C epsilon germline transcript. Identification of a novel IL-4 responsive element. *J. Immunol.* 150: 5408-17 (1993).

Kontermann et al., Bispecific antibodies. *Drug Discov. Today*, 20(7): 838-47 (2015).

Landschulz et al., The leucine zipper: a hypothetical structure common to a new class of DNA binding proteins. *Science* 240: 1759-64 (1988).

Langer et al., Biocompatibility of polymeric delivery systems for macromolecules. *J. Biomed. Mater. Res.* 15: 267-77 (1981).

Langer, Controlled release of macromolecules. *Chem. Tech.* 12: 98-105 (1982).

MacCallum et al., Antibody-antigen interactions: Contact analysis and binding site topography. *J. Mol. Biol.* 262: 732-45 (1996).

Mahler et al., Protein aggregation: Pathways, induction factors and analysis. *J. Pharm. Sci.* 98(9): 2909-34 (2009).

Martin et al., Structural families in loops of homologous proteins: automatic classification, modelling and application to antibodies. *J. Mol. Biol.* 263: 800-15 (1996).

Martin et al., Irreversible coupling of immunoglobulin fragments to preformed vesicles. *J. Biol. Chem.* 257: 286-8 (1982).

Meyer et al., Antimicrobial preservative use in parenteral products: past and present. *J. Pharm. Sci.* 96(12): 3155 (2007).

Nolan et al., Fluorescence-activated cell analysis and sorting of viable mammalian cells based on beta-D-galactosidase activity after transduction of *Escherichia coli* lacZ. *Proc. Natl. Acad. Sci. USA* 85: 2603-7 (1988).

Roberts, Therapeutic protein aggregation: Mechanisms, design, and control. *Trends Biotechnol.* 32(7): 372-80 (2014).

Sidman et al., Controlled release of macromolecules and pharmaceuticals from synthetic polypeptides based on glutamic acid. *Biopolymers* 2: 547-56 (1983).

Stauber et al., Development and applications of enhanced green fluorescent protein mutants. *Biotechniques* 24: 462-71 (1998).

Wang, Instability, stabilization, and formulation of liquid protein pharmaceuticals. *Int. J. Pharm.* 185(2): 129-88 (1999).

Aigner et al., T lymphocytes can be effectively recruited for ex vivo and in vivo lysis of AML blasts by a novel CD33/CD3-bispecific BiTE antibody construct, *Leukemia.* 27:1107-15 (2013).

Baeuerle et al., Bispecific T-cell engaging antibodies for cancer therapy, *Cancer Res.* 69:4941-4 (2009).

Database WPI Week 200025, Thomas Scientific, London, GB; AN 2000-287738 (Mar. 21, 2000).

Hartl et al., Influence of hydroxypropyl-Beta-cyclodextrin on the stability of dilute and highly concentrated immunoglobulin g formulations, *J. Pharm. Sci.* 102:4121-31 (2013).

International Preliminary Report on Patentability, PCT/EP2017/051486 (dated Jul. 31, 2018).

International Search Report and Written Opinion, PCT/EP2017/051486 (dated Apr. 18, 2017).

Ramezani et al., A comparative study on the physicochemical and biological stability of IgG1 and monoclonal antibodies during spray drying process, *Daru.* 22:31 (2014).

Serno et al., Inhibition of agitation-induced aggregation of an IgG-antibody by hydroxypropyl-beta-cyclodextrin, *J. Pharm. Sci.* 99:1193-206 (2010).

Serno et al., Protein stabilization by cyclodextrins in the liquid and dried state, *Adv. Drug Deliv. Rev.* 63:1086-106 (2011).

* cited by examiner

■ HMW (left column)
■ main (right column)

SEQUENCE LISTING

<160> NUMBER OF SEQ ID NOS: 188

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Gly Ser Ser Thr Gly Ala Val Thr Ser Gly Tyr Tyr Pro Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Gly Thr Lys Phe Leu Ala Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Ala Leu Trp Tyr Ser Asn Arg Trp Val
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Ile Tyr Ala Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Arg Ile Arg Ser Lys Tyr Asn Asn Tyr Ala Thr Tyr Tyr Ala Asp Ser
1               5                   10                  15

Val Lys Ser

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

<400> SEQUENCE: 6

His Gly Asn Phe Gly Asn Ser Tyr Val Ser Phe Phe Ala Tyr
1               5                   10

<210> SEQ ID NO 7
<211> LENGTH: 125
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser
        115                 120                 125

<210> SEQ ID NO 8
<211> LENGTH: 109
<212> TYPE: PRT
<213> ORGANISM: Artificial Sequence
<220> FEATURE:
<223> OTHER INFORMATION: Synthetic peptide

<400> SEQUENCE: 8

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 9
<211> LENGTH: 249
<212> TYPE: PRT
<213> ORGANISM: Artificial Sequence
<220> FEATURE:
<223> OTHER INFORMATION: Synthetic peptide

<400> SEQUENCE: 9

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
```

```
            195                 200                 205
Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Gly Ser Ser Thr Gly Ala Val Thr Ser Gly Tyr Tyr Pro Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Gly Thr Lys Phe Leu Ala Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Ala Leu Trp Tyr Ser Asn Arg Trp Val
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Lys Tyr Ala Met Asn
1               5

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide

<400> SEQUENCE: 14

Arg Ile Arg Ser Lys Tyr Asn Asn Tyr Ala Thr Tyr Tyr Ala Asp Ser
1               5                   10                  15

Val Lys Asp
```

```
<210> SEQ ID NO 15
<211> LENGTH: 14
<212> TYPE: PRT
<213> ORGANISM: Artificial Sequence
<220> FEATURE:
<223> OTHER INFORMATION: Synthetic peptide

<400> SEQUENCE: 15

His Gly Asn Phe Gly Asn Ser Tyr Ile Ser Tyr Trp Ala Tyr
1               5                   10

<210> SEQ ID NO 16
<211> LENGTH: 125
<212> TYPE: PRT
<213> ORGANISM: Artificial Sequence
<220> FEATURE:
<223> OTHER INFORMATION: Synthetic peptide

<400> SEQUENCE: 16

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 17
<211> LENGTH: 109
<212> TYPE: PRT
<213> ORGANISM: Artificial Sequence
<220> FEATURE:
<223> OTHER INFORMATION: Synthetic peptide

<400> SEQUENCE: 17

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 18
```

```
<211> LENGTH: 249
<212> TYPE: PRT
<213> ORGANISM: Artificial Sequence
<220> FEATURE:
<223> OTHER INFORMATION: Synthetic peptide

<400> SEQUENCE: 18
```

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

```
<210> SEQ ID NO 19
<211> LENGTH: 14
<212> TYPE: PRT
<213> ORGANISM: Artificial Sequence
<220> FEATURE:
<223> OTHER INFORMATION: Synthetic peptide

<400> SEQUENCE: 19
```

Gly Ser Ser Thr Gly Ala Val Thr Ser Gly Tyr Tyr Pro Asn
1               5                   10

```
<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20
```

Gly Thr Lys Phe Leu Ala Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Ala Leu Trp Tyr Ser Asn Arg Trp Val
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide

<400> SEQUENCE: 22

Ser Tyr Ala Met Asn
1               5

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide

<400> SEQUENCE: 23

Arg Ile Arg Ser Lys Tyr Asn Asn Tyr Ala Thr Tyr Tyr Ala Asp Ser
1               5                   10                  15

Val Lys Gly

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide

<400> SEQUENCE: 24

His Gly Asn Phe Gly Asn Ser Tyr Leu Ser Phe Trp Ala Tyr
1               5                   10

<210> SEQ ID NO 25
<211> LENGTH: 125
<212> TYPE: PRT
<213> ORGANISM: Artificial Sequence
<220> FEATURE:
<223> OTHER INFORMATION: Synthetic peptide

<400> SEQUENCE: 25

Glu Val Gln Leu Val Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

```
Ser Val Lys Gly Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser
        115                 120                 125

<210> SEQ ID NO 26
<211> LENGTH: 109
<212> TYPE: PRT
<213> ORGANISM: Artificial Sequence
<220> FEATURE:
<223> OTHER INFORMATION: Synthetic peptide

<400> SEQUENCE: 26

Gln Thr Val Val Thr Gln Glu Pro Ser Leu Thr Val Ser Pro Gly Gly
  1               5                  10                  15

Thr Val Thr Leu Thr Cys Gly Ser Ser Thr Gly Ala Val Thr Ser Gly
                 20                  25                  30

Tyr Tyr Pro Asn Trp Val Gln Gln Lys Pro Gly Gln Ala Pro Arg Gly
             35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Arg Trp Val Phe Gly Gly Gly Thr Lys Leu Thr Val Leu
            100                 105

<210> SEQ ID NO 27
<211> LENGTH: 249
<212> TYPE: PRT
<213> ORGANISM: Artificial Sequence
<220> FEATURE:
<223> OTHER INFORMATION: Synthetic peptide

<400> SEQUENCE: 27

Glu Val Gln Leu Val Glu Ser Gly Gly Gly Leu Glu Gln Pro Gly Gly
  1               5                  10                  15

Ser Leu Lys Leu Ser Cys Ala Ala Ser Gly Phe Thr Phe Asn Ser Tyr
                 20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
            130                 135                 140
```

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 28
<211> LENGTH: 14
<212> TYPE: PRT
<213> ORGANISM: Artificial Sequence
<220> FEATURE:
<223> OTHER INFORMATION: Synthetic peptide

<400> SEQUENCE: 28

Gly Ser Ser Thr Gly Ala Val Thr Ser Gly Tyr Tyr Pro Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Gly Thr Lys Phe Leu Ala Pro
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Ala Leu Trp Tyr Ser Asn Arg Trp Val
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Arg Tyr Ala Met Asn
1               5

<210> SEQ ID NO 32
<211> LENGTH: 19
<212> TYPE: PRT
<213> ORGANISM: Artificial Sequence
<220> FEATURE:
<223> OTHER INFORMATION: Synthetic peptide

<400> SEQUENCE: 32

Arg Ile Arg Ser Lys Tyr Asn Asn Tyr Ala Thr Tyr Tyr Ala Asp Ser
1               5                   10                  15

Val Lys Gly

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

His Gly Asn Phe Gly Asn Ser Tyr Leu Ser Tyr Phe Ala Tyr
1               5                   10

<210> SEQ ID NO 34
<211> LENGTH: 125
<212> TYPE: PRT
<213> ORGANISM: Artificial Sequence
<220> FEATURE:
<223> OTHER INFORMATION: Synthetic peptide

<400> SEQUENCE: 34

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser
        115                 120                 125

<210> SEQ ID NO 35
<211> LENGTH: 109
<212> TYPE: PRT
<213> ORGANISM: Artificial Sequence
<220> FEATURE:
<223> OTHER INFORMATION: Synthetic peptide

<400> SEQUENCE: 35

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 36
<211> LENGTH: 249
<212> TYPE: PRT
<213> ORGANISM: Artificial Sequence
<220> FEATURE:
<223> OTHER INFORMATION: Synthetic peptide

<400> SEQUENCE: 36

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Arg Ser Ser Thr Gly Ala Val Thr Ser Gly Tyr Tyr Pro Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Ala Thr Asp Met Arg Pro Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Ala Leu Trp Tyr Ser Asn Arg Trp Val
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Val Tyr Ala Met Asn
1               5

<210> SEQ ID NO 41
<211> LENGTH: 19
<212> TYPE: PRT
<213> ORGANISM: Artificial Sequence
<220> FEATURE:
<223> OTHER INFORMATION: Synthetic peptide

<400> SEQUENCE: 41

Arg Ile Arg Ser Lys Tyr Asn Asn Tyr Ala Thr Tyr Tyr Ala Asp Ser
1               5                   10                  15

Val Lys Lys

<210> SEQ ID NO 42
<211> LENGTH: 14
<212> TYPE: PRT
<213> ORGANISM: Artificial Sequence
<220> FEATURE:
<223> OTHER INFORMATION: Synthetic peptide

<400> SEQUENCE: 42

His Gly Asn Phe Gly Asn Ser Tyr Leu Ser Trp Trp Ala Tyr
1               5                   10

<210> SEQ ID NO 43
<211> LENGTH: 125
<212> TYPE: PRT
<213> ORGANISM: Artificial Sequence
<220> FEATURE:
<223> OTHER INFORMATION: Synthetic peptide

<400> SEQUENCE: 43

Glu Val Gln Leu Val Glu Ser Gly Gly Gly Leu Val Gln Pro Gly Gly

```
            1               5                  10                  15
        Ser Leu Lys Leu Ser Cys Ala Ala Ser Gly Phe Thr Phe Asn Val Tyr
                        20                  25                  30

Ala Met Asn Trp Val Arg Gln Ala Pro Gly Lys Gly Leu Glu Trp Val
                        35                  40                  45

Ala Arg Ile Arg Ser Lys Tyr Asn Asn Tyr Ala Thr Tyr Tyr Ala Asp
                        50                  55                  60

Ser Val Lys Lys Arg Phe Thr Ile Ser Arg Asp Asp Ser Lys Asn Thr
         65                  70                  75                  80

Ala Tyr Leu Gln Met Asn Asn Leu Lys Thr Glu Asp Thr Ala Val Tyr
                        85                  90                  95

Tyr Cys Val Arg His Gly Asn Phe Gly Asn Ser Tyr Leu Ser Trp Trp
                        100                 105                 110

Ala Tyr Trp Gly Gln Gly Thr Leu Val Thr Val Ser Ser
                        115                 120                 125

<210> SEQ ID NO 44
<211> LENGTH: 109
<212> TYPE: PRT
<213> ORGANISM: Artificial Sequence
<220> FEATURE:
<223> OTHER INFORMATION: Synthetic peptide

<400> SEQUENCE: 44

Gln Thr Val Val Thr Gln Glu Pro Ser Leu Thr Val Ser Pro Gly Gly
         1               5                  10                  15

Thr Val Thr Leu Thr Cys Arg Ser Ser Thr Gly Ala Val Thr Ser Gly
                        20                  25                  30

Tyr Tyr Pro Asn Trp Val Gln Gln Lys Pro Gly Gln Ala Pro Arg Gly
                        35                  40                  45

Leu Ile Gly Ala Thr Asp Met Arg Pro Ser Gly Thr Pro Ala Arg Phe
                        50                  55                  60

Ser Gly Ser Leu Leu Gly Gly Lys Ala Ala Leu Thr Leu Ser Gly Val
         65                  70                  75                  80

Gln Pro Glu Asp Glu Ala Glu Tyr Tyr Cys Ala Leu Trp Tyr Ser Asn
                        85                  90                  95

Arg Trp Val Phe Gly Gly Gly Thr Lys Leu Thr Val Leu
                        100                 105

<210> SEQ ID NO 45
<211> LENGTH: 249
<212> TYPE: PRT
<213> ORGANISM: Artificial Sequence
<220> FEATURE:
<223> OTHER INFORMATION: Synthetic peptide

<400> SEQUENCE: 45

Glu Val Gln Leu Val Glu Ser Gly Gly Gly Leu Val Gln Pro Gly Gly
         1               5                  10                  15

Ser Leu Lys Leu Ser Cys Ala Ala Ser Gly Phe Thr Phe Asn Val Tyr
                        20                  25                  30

Ala Met Asn Trp Val Arg Gln Ala Pro Gly Lys Gly Leu Glu Trp Val
                        35                  40                  45

Ala Arg Ile Arg Ser Lys Tyr Asn Asn Tyr Ala Thr Tyr Tyr Ala Asp
                        50                  55                  60

Ser Val Lys Lys Arg Phe Thr Ile Ser Arg Asp Asp Ser Lys Asn Thr
         65                  70                  75                  80
```

```
Ala Tyr Leu Gln Met Asn Asn Leu Lys Thr Glu Asp Thr Ala Val Tyr
            85                  90                  95

Tyr Cys Val Arg His Gly Asn Phe Gly Asn Ser Tyr Leu Ser Trp Trp
        100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Ala
            180                 185                 190

Thr Asp Met Arg Pro Ser Gly Thr Pro Ala Arg Phe Ser Gly Ser Leu
        195                 200                 205

Leu Gly Gly Lys Ala Ala Leu Thr Leu Ser Gly Val Gln Pro Glu Asp
            210                 215                 220

Glu Ala Glu Tyr Cys Ala Leu Trp Tyr Ser Asn Arg Trp Val Phe
225                 230                 235                 240

Gly Gly Gly Thr Lys Leu Thr Val Leu
                245
```

```
<210> SEQ ID NO 46
<211> LENGTH: 14
<212> TYPE: PRT
<213> ORGANISM: Artificial Sequence
<220> FEATURE:
<223> OTHER INFORMATION: Synthetic peptide

<400> SEQUENCE: 46

Gly Ser Ser Thr Gly Ala Val Thr Ser Gly Tyr Tyr Pro Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Gly Thr Lys Phe Leu Ala Pro
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Ala Leu Trp Tyr Ser Asn Arg Trp Val
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide
```

<400> SEQUENCE: 49

Lys Tyr Ala Met Asn
1               5

<210> SEQ ID NO 50
<211> LENGTH: 19
<212> TYPE: PRT
<213> ORGANISM: Artificial Sequence
<220> FEATURE:
<223> OTHER INFORMATION: Synthetic peptide

<400> SEQUENCE: 50

Arg Ile Arg Ser Lys Tyr Asn Asn Tyr Ala Thr Tyr Tyr Ala Asp Ser
1               5                   10                  15

Val Lys Ser

<210> SEQ ID NO 51
<211> LENGTH: 14
<212> TYPE: PRT
<213> ORGANISM: Artificial Sequence
<220> FEATURE:
<223> OTHER INFORMATION: Synthetic peptide

<400> SEQUENCE: 51

His Gly Asn Phe Gly Asn Ser Tyr Thr Ser Tyr Tyr Ala Tyr
1               5                   10

<210> SEQ ID NO 52
<211> LENGTH: 125
<212> TYPE: PRT
<213> ORGANISM: Artificial Sequence
<220> FEATURE:
<223> OTHER INFORMATION: Synthetic peptide

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser
        115                 120                 125

<210> SEQ ID NO 53
<211> LENGTH: 109
<212> TYPE: PRT
<213> ORGANISM: Artificial Sequence
<220> FEATURE:
<223> OTHER INFORMATION: Synthetic peptide

<400> SEQUENCE: 53

Gln Thr Val Val Thr Gln Glu Pro Ser Leu Thr Val Ser Pro Gly Gly

```
1               5                   10                  15
Thr Val Thr Leu Thr Cys Gly Ser Ser Thr Gly Ala Val Thr Ser Gly
                20                  25                  30

Tyr Tyr Pro Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
                100                 105

<210> SEQ ID NO 54
<211> LENGTH: 249
<212> TYPE: PRT
<213> ORGANISM: Artificial Sequence
<220> FEATURE:
<223> OTHER INFORMATION: Synthetic peptide

<400> SEQUENCE: 54

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

```
<210> SEQ ID NO 55
<211> LENGTH: 14
<212> TYPE: PRT
<213> ORGANISM: Artificial Sequence
<220> FEATURE:
<223> OTHER INFORMATION: Synthetic peptide

<400> SEQUENCE: 55

Arg Ser Ser Thr Gly Ala Val Thr Ser Gly Tyr Tyr Pro Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Ala Thr Asp Met Arg Pro Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Ala Leu Trp Tyr Ser Asn Arg Trp Val
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide

<400> SEQUENCE: 58

Gly Tyr Ala Met Asn
1               5

<210> SEQ ID NO 59
<211> LENGTH: 19
<212> TYPE: PRT
<213> ORGANISM: Artificial Sequence
<220> FEATURE:
<223> OTHER INFORMATION: Synthetic peptide

<400> SEQUENCE: 59

Arg Ile Arg Ser Lys Tyr Asn Asn Tyr Ala Thr Tyr Tyr Ala Asp Ser
1               5                   10                  15

Val Lys Glu

<210> SEQ ID NO 60
<211> LENGTH: 14
<212> TYPE: PRT
<213> ORGANISM: Artificial Sequence
<220> FEATURE:
<223> OTHER INFORMATION: Synthetic peptide

<400> SEQUENCE: 60

His Arg Asn Phe Gly Asn Ser Tyr Leu Ser Trp Phe Ala Tyr
1               5                   10
```

<210> SEQ ID NO 61
<211> LENGTH: 125
<212> TYPE: PRT
<213> ORGANISM: Artificial Sequence
<220> FEATURE:
<223> OTHER INFORMATION: Synthetic peptide

<400> SEQUENCE: 61

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Glu Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
            100                 105                 110

Ala Tyr Trp Gly Gln Gly Thr Leu Val Thr Val Ser Ser
        115                 120                 125
```

<210> SEQ ID NO 62
<211> LENGTH: 109
<212> TYPE: PRT
<213> ORGANISM: Artificial Sequence
<220> FEATURE:
<223> OTHER INFORMATION: Synthetic peptide

<400> SEQUENCE: 62

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 63
<211> LENGTH: 249
<212> TYPE: PRT
<213> ORGANISM: Artificial Sequence
<220> FEATURE:
<223> OTHER INFORMATION: Synthetic peptide

<400> SEQUENCE: 63

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
```

```
                    20                  25                  30
Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Glu Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                85                  90                  95

Tyr Cys Val Arg His Arg Asn Phe Gly Asn Ser Tyr Leu Ser Trp Phe
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Ala
                180                 185                 190

Thr Asp Met Arg Pro Ser Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245

<210> SEQ ID NO 64
<211> LENGTH: 14
<212> TYPE: PRT
<213> ORGANISM: Artificial Sequence
<220> FEATURE:
<223> OTHER INFORMATION: Synthetic peptide

<400> SEQUENCE: 64

Gly Ser Ser Thr Gly Ala Val Thr Ser Gly Tyr Tyr Pro Asn
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Gly Thr Lys Phe Leu Ala Pro
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66
```

```
Ala Leu Trp Tyr Ser Asn Arg Trp Val
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Val Tyr Ala Met Asn
1               5

<210> SEQ ID NO 68
<211> LENGTH: 19
<212> TYPE: PRT
<213> ORGANISM: Artificial Sequence
<220> FEATURE:
<223> OTHER INFORMATION: Synthetic peptide

<400> SEQUENCE: 68

Arg Ile Arg Ser Lys Tyr Asn Asn Tyr Ala Thr Tyr Tyr Ala Asp Ser
1               5                   10                  15

Val Lys Lys

<210> SEQ ID NO 69
<211> LENGTH: 14
<212> TYPE: PRT
<213> ORGANISM: Artificial Sequence
<220> FEATURE:
<223> OTHER INFORMATION: Synthetic peptide

<400> SEQUENCE: 69

His Gly Asn Phe Gly Asn Ser Tyr Ile Ser Trp Trp Ala Tyr
1               5                   10

<210> SEQ ID NO 70
<211> LENGTH: 125
<212> TYPE: PRT
<213> ORGANISM: Artificial Sequence
<220> FEATURE:
<223> OTHER INFORMATION: Synthetic peptide

<400> SEQUENCE: 70

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
        115                 120                 125
```

<210> SEQ ID NO 71
<211> LENGTH: 109
<212> TYPE: PRT
<213> ORGANISM: Artificial Sequence
<220> FEATURE:
<223> OTHER INFORMATION: Synthetic peptide

<400> SEQUENCE: 71

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 72
<211> LENGTH: 249
<212> TYPE: PRT
<213> ORGANISM: Artificial Sequence
<220> FEATURE:
<223> OTHER INFORMATION: Synthetic peptide

<400> SEQUENCE: 72

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205
```

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245

<210> SEQ ID NO 73
<211> LENGTH: 14
<212> TYPE: PRT
<213> ORGANISM: Artificial Sequence
<220> FEATURE:
<223> OTHER INFORMATION: Synthetic peptide

<400> SEQUENCE: 73

Gly Ser Ser Thr Gly Ala Val Thr Ser Gly Asn Tyr Pro Asn
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Gly Thr Lys Phe Leu Ala Pro
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Val Leu Trp Tyr Ser Asn Arg Trp Val
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic peptide

<400> SEQUENCE: 76

Ser Tyr Ala Met Asn
1               5

<210> SEQ ID NO 77
<211> LENGTH: 19
<212> TYPE: PRT
<213> ORGANISM: Artificial Sequence
<220> FEATURE:
<223> OTHER INFORMATION: Synthetic peptide

<400> SEQUENCE: 77

Arg Ile Arg Ser Lys Tyr Asn Asn Tyr Ala Thr Tyr Tyr Ala Asp Ser
1               5                   10                  15

Val Lys Gly

<210> SEQ ID NO 78

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 78

His Gly Asn Phe Gly Asn Ser Tyr Val Ser Trp Trp Ala Tyr
1               5                   10

<210> SEQ ID NO 79
<211> LENGTH: 125
<212> TYPE: PRT
<213> ORGANISM: Artificial Sequence
<220> FEATURE:
<223> OTHER INFORMATION: Synthetic peptide

<400> SEQUENCE: 79

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser
        115                 120                 125

<210> SEQ ID NO 80
<211> LENGTH: 109
<212> TYPE: PRT
<213> ORGANISM: Artificial Sequence
<220> FEATURE:
<223> OTHER INFORMATION: Synthetic peptide

<400> SEQUENCE: 80

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 81
<211> LENGTH: 249
```

```
<212> TYPE: PRT
<213> ORGANISM: Artificial Sequence
<220> FEATURE:
<223> OTHER INFORMATION: Synthetic peptide

<400> SEQUENCE: 81

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 82
<211> LENGTH: 14
<212> TYPE: PRT
<213> ORGANISM: Artificial Sequence
<220> FEATURE:
<223> OTHER INFORMATION: Synthetic peptide

<400> SEQUENCE: 82

Gly Ser Ser Thr Gly Ala Val Thr Ser Gly Asn Tyr Pro Asn
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Gly Thr Lys Phe Leu Ala Pro
```

```
1               5
```

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

```
Val Leu Trp Tyr Ser Asn Arg Trp Val
1               5
```

<210> SEQ ID NO 85
<211> LENGTH: 5
<212> TYPE: PRT
<213> ORGANISM: Artificial Sequence
<220> FEATURE:
<223> OTHER INFORMATION: Synthetic peptide

<400> SEQUENCE: 85

```
Lys Tyr Ala Met Asn
1               5
```

<210> SEQ ID NO 86
<211> LENGTH: 19
<212> TYPE: PRT
<213> ORGANISM: Artificial Sequence
<220> FEATURE:
<223> OTHER INFORMATION: Synthetic peptide

<400> SEQUENCE: 86

```
Arg Ile Arg Ser Lys Tyr Asn Asn Tyr Ala Thr Tyr Tyr Ala Asp Ser
1               5                   10                  15

Val Lys Asp
```

<210> SEQ ID NO 87
<211> LENGTH: 14
<212> TYPE: PRT
<213> ORGANISM: Artificial Sequence
<220> FEATURE:
<223> OTHER INFORMATION: Synthetic peptide

<400> SEQUENCE: 87

```
His Gly Asn Phe Gly Asn Ser Tyr Ile Ser Tyr Trp Ala Tyr
1               5                   10
```

<210> SEQ ID NO 88
<211> LENGTH: 125
<212> TYPE: PRT
<213> ORGANISM: Artificial Sequence
<220> FEATURE:
<223> OTHER INFORMATION: Synthetic peptide

<400> SEQUENCE: 88

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
```

```
65                  70                  75                  80
Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 89
<211> LENGTH: 109
<212> TYPE: PRT
<213> ORGANISM: Artificial Sequence
<220> FEATURE:
<223> OTHER INFORMATION: Synthetic peptide

<400> SEQUENCE: 89

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105
```

<210> SEQ ID NO 90
<211> LENGTH: 249
<212> TYPE: PRT
<213> ORGANISM: Artificial Sequence
<220> FEATURE:
<223> OTHER INFORMATION: Synthetic peptide

<400> SEQUENCE: 90

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140
```

```
Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 91
<211> LENGTH: 5
<212> TYPE: PRT
<213> ORGANISM: Artificial Sequence
<220> FEATURE:
<223> OTHER INFORMATION: Synthetic peptide

<400> SEQUENCE: 91

Asn Tyr Gly Met Asn
1               5

<210> SEQ ID NO 92
<211> LENGTH: 17
<212> TYPE: PRT
<213> ORGANISM: Artificial Sequence
<220> FEATURE:
<223> OTHER INFORMATION: Synthetic peptide

<400> SEQUENCE: 92

Trp Ile Asn Thr Tyr Thr Gly Glu Pro Thr Tyr Ala Asp Lys Phe Gln
1               5                   10                  15

Gly

<210> SEQ ID NO 93
<211> LENGTH: 13
<212> TYPE: PRT
<213> ORGANISM: Artificial Sequence
<220> FEATURE:
<223> OTHER INFORMATION: Synthetic peptide

<400> SEQUENCE: 93

Trp Ser Trp Ser Asp Gly Tyr Tyr Val Tyr Phe Asp Tyr
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Synthetic peptide

<400> SEQUENCE: 94

Lys Ser Ser Gln Ser Val Leu Asp Ser Ser Thr Asn Lys Asn Ser Leu
1               5                   10                  15

Ala

<210> SEQ ID NO 95
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 95

Trp Ala Ser Thr Arg Glu Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Gln Gln Ser Ala His Phe Pro Ile Thr
1               5

<210> SEQ ID NO 97
<211> LENGTH: 122
<212> TYPE: PRT
<213> ORGANISM: Artificial Sequence
<220> FEATURE:
<223> OTHER INFORMATION: Synthetic peptide

<400> SEQUENCE: 97

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Tyr Ala Asp Lys Phe
        50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120

<210> SEQ ID NO 98
<211> LENGTH: 113
<212> TYPE: PRT
<213> ORGANISM: Artificial Sequence
<220> FEATURE:
<223> OTHER INFORMATION: Synthetic peptide

<400> SEQUENCE: 98

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Thr Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
        50                  55                  60
```

Pro Asp Arg Phe Ser Gly Ser Gly Ser Gly Thr Asp Phe Thr Leu Thr
65                  70                  75                  80

Ile Asp Ser Pro Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 99
<211> LENGTH: 250
<212> TYPE: PRT
<213> ORGANISM: Artificial Sequence
<220> FEATURE:
<223> OTHER INFORMATION: Synthetic peptide

<400> SEQUENCE: 99

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Lys Phe
        50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 100
<211> LENGTH: 505
<212> TYPE: PRT
<213> ORGANISM: Artificial Sequence
<220> FEATURE:
<223> OTHER INFORMATION: Synthetic peptide

<400> SEQUENCE: 100

Gln Val Gln Leu Val Gln Ser Gly Ala Glu Val Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Thr Asn Lys Asn Ser Leu
            165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
            245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
            325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

```
Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465             470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
            500                 505

<210> SEQ ID NO 101
<211> LENGTH: 5
<212> TYPE: PRT
<213> ORGANISM: Artificial Sequence
<220> FEATURE:
<223> OTHER INFORMATION: Synthetic peptide

<400> SEQUENCE: 101

Asn Tyr Gly Met Asn
1               5

<210> SEQ ID NO 102
<211> LENGTH: 17
<212> TYPE: PRT
<213> ORGANISM: Artificial Sequence
<220> FEATURE:
<223> OTHER INFORMATION: Synthetic peptide

<400> SEQUENCE: 102

Trp Ile Asn Thr Tyr Thr Gly Glu Pro Thr Tyr Ala Asp Lys Phe Gln
1               5                   10                  15

Gly

<210> SEQ ID NO 103
<211> LENGTH: 13
<212> TYPE: PRT
<213> ORGANISM: Artificial Sequence
<220> FEATURE:
<223> OTHER INFORMATION: Synthetic peptide

<400> SEQUENCE: 103

Trp Ser Trp Ser Asp Gly Tyr Tyr Val Tyr Phe Asp Tyr
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Synthetic peptide

<400> SEQUENCE: 104

Lys Ser Ser Gln Ser Val Leu Asp Ser Ser Thr Asn Lys Asn Ser Leu
1               5                   10                  15

Ala

<210> SEQ ID NO 105
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 105

Trp Ala Ser Thr Arg Glu Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide

<400> SEQUENCE: 106

Gln Gln Ser Ala His Phe Pro Ile Thr
1               5

<210> SEQ ID NO 107
<211> LENGTH: 122
<212> TYPE: PRT
<213> ORGANISM: Artificial Sequence
<220> FEATURE:
<223> OTHER INFORMATION: Synthetic peptide

<400> SEQUENCE: 107

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Cys Leu Glu Trp Met
            35                  40                  45

Gly Trp Ile Asn Thr Tyr Thr Gly Glu Pro Thr Tyr Ala Asp Lys Phe
        50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120

<210> SEQ ID NO 108
<211> LENGTH: 113
<212> TYPE: PRT
<213> ORGANISM: Artificial Sequence
<220> FEATURE:
<223> OTHER INFORMATION: Synthetic peptide

<400> SEQUENCE: 108

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Thr Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80
```

Ile Asp Ser Pro Gln Pro Glu Asp Ser Ala Thr Tyr Tyr Cys Gln Gln
            85                  90                  95

Ser Ala His Phe Pro Ile Thr Phe Gly Cys Gly Thr Arg Leu Glu Ile
            100                 105                 110

Lys

<210> SEQ ID NO 109
<211> LENGTH: 250
<212> TYPE: PRT
<213> ORGANISM: Artificial Sequence
<220> FEATURE:
<223> OTHER INFORMATION: Synthetic peptide

<400> SEQUENCE: 109

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
            35                  40                  45

Gly Trp Ile Asn Thr Tyr Thr Gly Glu Pro Thr Tyr Ala Asp Lys Phe
        50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
            115                 120                 125

Gly Gly Ser Gly Gly Gly Ser Asp Ile Val Met Thr Gln Ser
        130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
            165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
        210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys
            245                 250

<210> SEQ ID NO 110
<211> LENGTH: 505
<212> TYPE: PRT
<213> ORGANISM: Artificial Sequence
<220> FEATURE:
<223> OTHER INFORMATION: Synthetic peptide

<400> SEQUENCE: 110

Gln Val Gln Leu Val Gln Ser Gly Ala Glu Val Lys Lys Pro Gly Glu
1               5                   10                  15

```
Ser Val Lys Val Ser Cys Lys Ala Ser Gly Tyr Thr Phe Thr Asn Tyr
            20                  25                  30
Gly Met Asn Trp Val Lys Gln Ala Pro Gly Gln Cys Leu Glu Trp Met
            35                  40                  45
Gly Trp Ile Asn Thr Tyr Thr Gly Glu Pro Thr Tyr Ala Asp Lys Phe
 50                  55                  60
Gln Gly Arg Val Thr Met Thr Thr Asp Thr Ser Thr Ser Thr Ala Tyr
 65                  70                  75                  80
Met Glu Ile Arg Asn Leu Gly Asp Asp Thr Ala Val Tyr Tyr Cys
             85                  90                  95
Ala Arg Trp Ser Trp Ser Asp Gly Tyr Tyr Val Tyr Phe Asp Tyr Trp
            100                 105                 110
Gly Gln Gly Thr Ser Val Thr Val Ser Ser Gly Gly Gly Gly Ser Gly
            115                 120                 125
Gly Gly Gly Ser Gly Gly Gly Gly Ser Asp Ile Val Met Thr Gln Ser
            130                 135                 140
Pro Asp Ser Leu Thr Val Ser Leu Gly Glu Arg Thr Thr Ile Asn Cys
145                 150                 155                 160
Lys Ser Ser Gln Ser Val Leu Asp Ser Ser Thr Asn Lys Asn Ser Leu
            165                 170                 175
Ala Trp Tyr Gln Gln Lys Pro Gly Gln Pro Pro Lys Leu Leu Leu Ser
            180                 185                 190
Trp Ala Ser Thr Arg Glu Ser Gly Ile Pro Asp Arg Phe Ser Gly Ser
            195                 200                 205
Gly Ser Gly Thr Asp Phe Thr Leu Thr Ile Asp Ser Pro Gln Pro Glu
            210                 215                 220
Asp Ser Ala Thr Tyr Tyr Cys Gln Gln Ser Ala His Phe Pro Ile Thr
225                 230                 235                 240
Phe Gly Cys Gly Thr Arg Leu Glu Ile Lys Ser Gly Gly Gly Gly Ser
            245                 250                 255
Glu Val Gln Leu Val Glu Ser Gly Gly Gly Leu Val Gln Pro Gly Gly
            260                 265                 270
Ser Leu Lys Leu Ser Cys Ala Ala Ser Gly Phe Thr Phe Asn Lys Tyr
            275                 280                 285
Ala Met Asn Trp Val Arg Gln Ala Pro Gly Lys Gly Leu Glu Trp Val
            290                 295                 300
Ala Arg Ile Arg Ser Lys Tyr Asn Asn Tyr Ala Thr Tyr Tyr Ala Asp
305                 310                 315                 320
Ser Val Lys Asp Arg Phe Thr Ile Ser Arg Asp Ser Lys Asn Thr
            325                 330                 335
Ala Tyr Leu Gln Met Asn Asn Leu Lys Thr Glu Asp Thr Ala Val Tyr
            340                 345                 350
Tyr Cys Val Arg His Gly Asn Phe Gly Asn Ser Tyr Ile Ser Tyr Trp
            355                 360                 365
Ala Tyr Trp Gly Gln Gly Thr Leu Val Thr Val Ser Ser Gly Gly Gly
            370                 375                 380
Gly Ser Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
            405                 410                 415
Thr Cys Gly Ser Ser Thr Gly Ala Val Thr Ser Gly Asn Tyr Pro Asn
            420                 425                 430
```

```
Trp Val Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
                500                 505

<210> SEQ ID NO 111
<211> LENGTH: 5
<212> TYPE: PRT
<213> ORGANISM: Artificial Sequence
<220> FEATURE:
<223> OTHER INFORMATION: Synthetic peptide

<400> SEQUENCE: 111

Asn Tyr Gly Met Asn
1               5

<210> SEQ ID NO 112
<211> LENGTH: 17
<212> TYPE: PRT
<213> ORGANISM: Artificial Sequence
<220> FEATURE:
<223> OTHER INFORMATION: Synthetic peptide

<400> SEQUENCE: 112

Trp Ile Asn Thr Tyr Thr Gly Glu Pro Thr Tyr Ala Asp Asp Phe Lys
1               5                   10                  15

Gly

<210> SEQ ID NO 113
<211> LENGTH: 13
<212> TYPE: PRT
<213> ORGANISM: Artificial Sequence
<220> FEATURE:
<223> OTHER INFORMATION: Synthetic peptide

<400> SEQUENCE: 113

Trp Ser Trp Ser Asp Gly Tyr Tyr Val Tyr Phe Asp Tyr
1               5                   10

<210> SEQ ID NO 114
<211> LENGTH: 17
<212> TYPE: PRT
<213> ORGANISM: Artificial Sequence
<220> FEATURE:
<223> OTHER INFORMATION: Synthetic peptide

<400> SEQUENCE: 114

Lys Ser Ser Gln Ser Val Leu Asp Ser Ser Lys Asn Lys Asn Ser Leu
1               5                   10                  15

Ala

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 115

Trp Ala Ser Thr Arg Glu Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide

<400> SEQUENCE: 116

Gln Gln Ser Ala His Phe Pro Ile Thr
1               5

<210> SEQ ID NO 117
<211> LENGTH: 122
<212> TYPE: PRT
<213> ORGANISM: Artificial Sequence
<220> FEATURE:
<223> OTHER INFORMATION: Synthetic peptide

<400> SEQUENCE: 117

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 118
<211> LENGTH: 113
<212> TYPE: PRT
<213> ORGANISM: Artificial Sequence
<220> FEATURE:
<223> OTHER INFORMATION: Synthetic peptide

<400> SEQUENCE: 118

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Lys Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
             100                 105                 110

Lys

<210> SEQ ID NO 119
<211> LENGTH: 250
<212> TYPE: PRT
<213> ORGANISM: Artificial Sequence
<220> FEATURE:
<223> OTHER INFORMATION: Synthetic peptide

<400> SEQUENCE: 119

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Ser Ser Asp Thr Ser Thr Ser Thr Ala Tyr
65                  70                  75                  80

Leu Glu Ile Asn Ser Leu Arg Ser Asp Asp Thr Ala Ile Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 120
<211> LENGTH: 5
<212> TYPE: PRT
<213> ORGANISM: Artificial Sequence
<220> FEATURE:
<223> OTHER INFORMATION: Synthetic peptide

<400> SEQUENCE: 120

Asn Tyr Gly Met Asn
1               5

<210> SEQ ID NO 121

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 121

Trp Ile Asn Thr Tyr Thr Gly Glu Pro Thr Tyr Ala Asp Asp Phe Lys
1               5                   10                  15
Gly

<210> SEQ ID NO 122
<211> LENGTH: 13
<212> TYPE: PRT
<213> ORGANISM: Artificial Sequence
<220> FEATURE:
<223> OTHER INFORMATION: Synthetic peptide

<400> SEQUENCE: 122

Trp Ser Trp Ser Asp Gly Tyr Tyr Val Tyr Phe Asp Tyr
1               5                   10

<210> SEQ ID NO 123
<211> LENGTH: 122
<212> TYPE: PRT
<213> ORGANISM: Artificial Sequence
<220> FEATURE:
<223> OTHER INFORMATION: Synthetic peptide

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Leu Glu Leu His Asn Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 124
<211> LENGTH: 17
<212> TYPE: PRT
<213> ORGANISM: Artificial Sequence
<220> FEATURE:
<223> OTHER INFORMATION: Synthetic peptide

<400> SEQUENCE: 124

Lys Ser Ser Gln Ser Val Leu Asp Ser Ser Lys Asn Lys Asn Ser Leu
1               5                   10                  15
Ala

<210> SEQ ID NO 125
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 125

Trp Ala Ser Thr Arg Glu Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

Gln Gln Ser Ala His Phe Pro Ile Thr
1               5

<210> SEQ ID NO 127
<211> LENGTH: 113
<212> TYPE: PRT
<213> ORGANISM: Artificial Sequence
<220> FEATURE:
<223> OTHER INFORMATION: Synthetic peptide

<400> SEQUENCE: 127

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Lys Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 128
<211> LENGTH: 250
<212> TYPE: PRT
<213> ORGANISM: Artificial Sequence
<220> FEATURE:
<223> OTHER INFORMATION: Synthetic peptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Tyr Ala Asp Asp Phe
    50                  55                  60

Lys Gly Arg Val Thr Met Thr Ser Asp Thr Ser Thr Ser Thr Ala Tyr
65                  70                  75                  80
```

```
Leu Glu Leu His Asn Leu Arg Ser Asp Asp Thr Ala Val Tyr Tyr Cys
                85                  90                  95
Ala Arg Trp Ser Trp Ser Asp Gly Tyr Tyr Val Tyr Phe Asp Tyr Trp
            100                 105                 110
Gly Gln Gly Thr Thr Val Thr Val Ser Gly Gly Gly Gly Ser Gly
        115                 120                 125
Gly Gly Ser Gly Gly Gly Ser Asp Ile Val Met Thr Gln Ser
130                 135                 140
Pro Asp Ser Leu Thr Val Ser Leu Gly Glu Arg Thr Thr Ile Asn Cys
145                 150                 155                 160
Lys Ser Ser Gln Ser Val Leu Asp Ser Ser Lys Asn Lys Asn Ser Leu
                165                 170                 175
Ala Trp Tyr Gln Gln Lys Pro Gly Gln Pro Pro Lys Leu Leu Leu Ser
            180                 185                 190
Trp Ala Ser Thr Arg Glu Ser Gly Ile Pro Asp Arg Phe Ser Gly Ser
        195                 200                 205
Gly Ser Gly Thr Asp Phe Thr Leu Thr Ile Asp Ser Leu Gln Pro Glu
    210                 215                 220
Asp Ser Ala Thr Tyr Tyr Cys Gln Gln Ser Ala His Phe Pro Ile Thr
225                 230                 235                 240
Phe Gly Gln Gly Thr Arg Leu Glu Ile Lys
                245                 250

<210> SEQ ID NO 129
<211> LENGTH: 5
<212> TYPE: PRT
<213> ORGANISM: Artificial Sequence
<220> FEATURE:
<223> OTHER INFORMATION: Synthetic peptide

<400> SEQUENCE: 129

Asn Tyr Gly Met Asn
1               5

<210> SEQ ID NO 130
<211> LENGTH: 17
<212> TYPE: PRT
<213> ORGANISM: Artificial Sequence
<220> FEATURE:
<223> OTHER INFORMATION: Synthetic peptide

<400> SEQUENCE: 130

Trp Ile Asn Thr Tyr Thr Gly Glu Pro Thr Tyr Ala Asp Asp Phe Lys
1               5                   10                  15
Gly

<210> SEQ ID NO 131
<211> LENGTH: 13
<212> TYPE: PRT
<213> ORGANISM: Artificial Sequence
<220> FEATURE:
<223> OTHER INFORMATION: Synthetic peptide

<400> SEQUENCE: 131

Trp Ser Trp Ser Asp Gly Tyr Tyr Val Tyr Phe Asp Tyr
1               5                   10

<210> SEQ ID NO 132
<211> LENGTH: 17
<212> TYPE: PRT
```

<213> ORGANISM: Artificial Sequence
<220> FEATURE:
<223> OTHER INFORMATION: Synthetic peptide

<400> SEQUENCE: 132

Lys Ser Ser Gln Ser Val Leu Asp Ser Ser Lys Asn Lys Asn Ser Leu
1               5                   10                  15

Ala

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide

<400> SEQUENCE: 133

Trp Ala Ser Thr Arg Glu Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide

<400> SEQUENCE: 134

Gln Gln Ser Ala His Phe Pro Ile Thr
1               5

<210> SEQ ID NO 135
<211> LENGTH: 122
<212> TYPE: PRT
<213> ORGANISM: Artificial Sequence
<220> FEATURE:
<223> OTHER INFORMATION: Synthetic peptide

<400> SEQUENCE: 135

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
            115                 120

<210> SEQ ID NO 136
<211> LENGTH: 113
<212> TYPE: PRT
<213> ORGANISM: Artificial Sequence
<220> FEATURE:
<223> OTHER INFORMATION: Synthetic peptide

<400> SEQUENCE: 136

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
            20                  25                  30

Ser Lys Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 137
<211> LENGTH: 250
<212> TYPE: PRT
<213> ORGANISM: Artificial Sequence
<220> FEATURE:
<223> OTHER INFORMATION: Synthetic peptide

<400> SEQUENCE: 137

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
50                  55                  60

Lys Gly Arg Val Thr Met Thr Thr Asp Thr Ser Thr Ser Thr Ala Tyr
65                  70                  75                  80

Met Glu Ile Arg Asn Leu Arg Asn Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Val Met Thr Gln Ser
130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
210                 215                 220

Asp Ser Ala Thr Tyr Tyr Cys Gln Gln Ser Ala His Phe Pro Ile Thr
225                 230                 235                 240

```
Phe Gly Gln Gly Thr Arg Leu Glu Ile Lys
            245                 250

<210> SEQ ID NO 138
<211> LENGTH: 5
<212> TYPE: PRT
<213> ORGANISM: Artificial Sequence
<220> FEATURE:
<223> OTHER INFORMATION: Synthetic peptide

<400> SEQUENCE: 138

Asn Tyr Gly Met Asn
1               5

<210> SEQ ID NO 139
<211> LENGTH: 17
<212> TYPE: PRT
<213> ORGANISM: Artificial Sequence
<220> FEATURE:
<223> OTHER INFORMATION: Synthetic peptide

<400> SEQUENCE: 139

Trp Ile Asn Thr Tyr Thr Gly Glu Pro Thr Tyr Ala Asp Asp Phe Lys
1               5                   10                  15

Gly

<210> SEQ ID NO 140
<211> LENGTH: 13
<212> TYPE: PRT
<213> ORGANISM: Artificial Sequence
<220> FEATURE:
<223> OTHER INFORMATION: Synthetic peptide

<400> SEQUENCE: 140

Trp Ser Trp Ser Asp Gly Tyr Tyr Val Tyr Phe Asp Tyr
1               5                   10

<210> SEQ ID NO 141
<211> LENGTH: 17
<212> TYPE: PRT
<213> ORGANISM: Artificial Sequence
<220> FEATURE:
<223> OTHER INFORMATION: Synthetic peptide

<400> SEQUENCE: 141

Lys Ser Ser Gln Ser Val Leu Asp Ser Ser Lys Asn Lys Asn Ser Leu
1               5                   10                  15

Ala

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide

<400> SEQUENCE: 142

Trp Ala Ser Thr Arg Glu Ser
1               5

<210> SEQ ID NO 143
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 143

Gln Gln Ser Ala His Phe Pro Ile Thr
1               5

<210> SEQ ID NO 144
<211> LENGTH: 122
<212> TYPE: PRT
<213> ORGANISM: Artificial Sequence
<220> FEATURE:
<223> OTHER INFORMATION: Synthetic peptide

<400> SEQUENCE: 144

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Gly Glu Pro Tyr Ala Asp Asp Phe
        50                  55                  60

Lys Gly Arg Val Thr Met Thr Ser Asp Thr Ser Thr Ser Thr Ala Tyr
65                  70                  75                  80

Met Glu Ile Ser Ser Leu Arg Ser Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 145
<211> LENGTH: 113
<212> TYPE: PRT
<213> ORGANISM: Artificial Sequence
<220> FEATURE:
<223> OTHER INFORMATION: Synthetic peptide

<400> SEQUENCE: 145

Asp Ile Val Met Thr Gln Ser Pro Asp Ser Leu Thr Val Ser Leu Gly
1               5                   10                  15

Glu Arg Thr Thr Ile Asn Cys Lys Ser Ser Gln Ser Val Leu Asp Ser
                20                  25                  30

Ser Lys Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
        50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 146
<211> LENGTH: 250
<212> TYPE: PRT
<213> ORGANISM: Artificial Sequence

```
<220> FEATURE:
<223> OTHER INFORMATION: Synthetic peptide

<400> SEQUENCE: 146

Gln Val Gln Leu Val Gln Ser Gly Ala Glu Val Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Ser Asp Thr Ser Thr Ser Thr Ala Tyr
65                  70                  75                  80

Met Glu Ile Ser Ser Leu Arg Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Ile Asn Cys
145                 150                 155                 160

Lys Ser Ser Gln Ser Val Leu Asp Ser Ser Lys Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 147
<211> LENGTH: 5
<212> TYPE: PRT
<213> ORGANISM: Artificial Sequence
<220> FEATURE:
<223> OTHER INFORMATION: Synthetic peptide

<400> SEQUENCE: 147

Asn Tyr Gly Met Asn
1               5

<210> SEQ ID NO 148
<211> LENGTH: 17
<212> TYPE: PRT
<213> ORGANISM: Artificial Sequence
<220> FEATURE:
<223> OTHER INFORMATION: Synthetic peptide

<400> SEQUENCE: 148

Trp Ile Asn Thr Tyr Thr Gly Glu Thr Asn Tyr Ala Asp Lys Phe Gln
1               5                   10                  15
```

Gly

<210> SEQ ID NO 149
<211> LENGTH: 13
<212> TYPE: PRT
<213> ORGANISM: Artificial Sequence
<220> FEATURE:
<223> OTHER INFORMATION: Synthetic peptide

<400> SEQUENCE: 149

Trp Ser Trp Ser Asp Gly Tyr Tyr Val Tyr Phe Asp Tyr
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Synthetic peptide

<400> SEQUENCE: 150

Lys Ser Ser Gln Ser Val Leu Asp Ser Ser Thr Asn Lys Asn Ser Leu
1               5                   10                  15

Ala

<210> SEQ ID NO 151
<211> LENGTH: 6
<212> TYPE: PRT
<213> ORGANISM: Artificial Sequence
<220> FEATURE:
<223> OTHER INFORMATION: Synthetic peptide

<400> SEQUENCE: 151

Trp Ala Ser Thr Arg Glu
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic peptide

<400> SEQUENCE: 152

Gln Gln Ser Ala His Phe Pro Ile Thr
1               5

<210> SEQ ID NO 153
<211> LENGTH: 122
<212> TYPE: PRT
<213> ORGANISM: Artificial Sequence
<220> FEATURE:
<223> OTHER INFORMATION: Synthetic peptide

<400> SEQUENCE: 153

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Thr Asn Tyr Ala Asp Lys Phe
        50                  55                  60

Gln Gly Arg Val Thr Phe Thr Ser Asp Thr Ser Thr Ser Thr Ala Tyr

```
                65                  70                  75                  80
Met Glu Leu Arg Asn Leu Lys Ser Asp Asp Thr Ala Val Tyr Tyr Cys
                    85                  90                  95

Ala Arg Trp Ser Trp Ser Asp Gly Tyr Tyr Val Tyr Phe Asp Tyr Trp
                100                 105                 110

Gly Gln Gly Thr Thr Val Thr Val Ser Ser
            115                 120

<210> SEQ ID NO 154
<211> LENGTH: 113
<212> TYPE: PRT
<213> ORGANISM: Artificial Sequence
<220> FEATURE:
<223> OTHER INFORMATION: Synthetic peptide

<400> SEQUENCE: 154

Asp Ile Val Met Thr Gln Ser Pro Asp Ser Met Thr Val Ser Leu Gly
1               5                   10                  15

Glu Arg Thr Thr Ile Asn Cys Lys Ser Ser Gln Ser Val Leu Asp Ser
                20                  25                  30

Ser Thr Asn Lys Asn Ser Leu Ala Trp Tyr Gln Gln Lys Pro Gly Gln
            35                  40                  45

Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Asp Ile
            100                 105                 110

Lys

<210> SEQ ID NO 155
<211> LENGTH: 250
<212> TYPE: PRT
<213> ORGANISM: Artificial Sequence
<220> FEATURE:
<223> OTHER INFORMATION: Synthetic peptide

<400> SEQUENCE: 155

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
                100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Val Met Thr Gln Ser
```

```
                    130                 135                 140
Pro Asp Ser Met Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
                180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Leu Gln Pro Glu
        210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Asp Ile Lys
                245                 250

<210> SEQ ID NO 156
<211> LENGTH: 5
<212> TYPE: PRT
<213> ORGANISM: Artificial Sequence
<220> FEATURE:
<223> OTHER INFORMATION: Synthetic peptide

<400> SEQUENCE: 156

Asn Tyr Gly Met Asn
1               5

<210> SEQ ID NO 157
<211> LENGTH: 17
<212> TYPE: PRT
<213> ORGANISM: Artificial Sequence
<220> FEATURE:
<223> OTHER INFORMATION: Synthetic peptide

<400> SEQUENCE: 157

Trp Ile Asn Thr Tyr Thr Gly Glu Thr Asn Tyr Ala Asp Lys Phe Gln
1               5                   10                  15

Gly

<210> SEQ ID NO 158
<211> LENGTH: 13
<212> TYPE: PRT
<213> ORGANISM: Artificial Sequence
<220> FEATURE:
<223> OTHER INFORMATION: Synthetic peptide

<400> SEQUENCE: 158

Trp Ser Trp Ser Asp Gly Tyr Tyr Val Tyr Phe Asp Tyr
1               5                   10

<210> SEQ ID NO 159
<211> LENGTH: 17
<212> TYPE: PRT
<213> ORGANISM: Artificial Sequence
<220> FEATURE:
<223> OTHER INFORMATION: Synthetic peptide

<400> SEQUENCE: 159

Lys Ser Ser Gln Ser Val Leu Asp Ser Ser Thr Asn Lys Asn Ser Leu
1               5                   10                  15

Ala
```

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Trp Ala Ser Thr Arg Glu Ser
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic peptide

<400> SEQUENCE: 161

Gln Gln Ser Ala His Phe Pro Ile Thr
1               5

<210> SEQ ID NO 162
<211> LENGTH: 122
<212> TYPE: PRT
<213> ORGANISM: Artificial Sequence
<220> FEATURE:
<223> OTHER INFORMATION: Synthetic peptide

<400> SEQUENCE: 162

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65                  70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser
        115                 120

<210> SEQ ID NO 163
<211> LENGTH: 113
<212> TYPE: PRT
<213> ORGANISM: Artificial Sequence
<220> FEATURE:
<223> OTHER INFORMATION: Synthetic peptide

<400> SEQUENCE: 163

Asp Ile Val Met Thr Gln Ser Pro Asp Ser Leu Ser Val Ser Leu Gly
1               5                   10                  15

Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Gln Lys Pro Gly Gln
        35                  40                  45

```
Pro Pro Lys Leu Leu Leu Ser Trp Ala Ser Thr Arg Glu Ser Gly Ile
    50                  55                  60

Pro Asp Arg Phe Ser Gly Ser Gly Ser Gly Thr Asp Phe Thr Leu Thr
65              70                  75                  80

Ile Asp Ser Leu Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 164
<211> LENGTH: 250
<212> TYPE: PRT
<213> ORGANISM: Artificial Sequence
<220> FEATURE:
<223> OTHER INFORMATION: Synthetic peptide

<400> SEQUENCE: 164

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Thr Asn Tyr Ala Asp Lys Phe
    50                  55                  60

Gln Gly Arg Val Thr Phe Thr Ser Asp Thr Ser Thr Ser Thr Ala Tyr
65              70                  75                  80

Met Glu Leu Arg Asn Leu Lys Ser Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Val Met Thr Gln Ser
        130                 135                 140

Pro Asp Ser Leu Ser Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Leu Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 165
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 165

Asn Tyr Gly Met Asn
1               5

<210> SEQ ID NO 166
<211> LENGTH: 17
<212> TYPE: PRT
<213> ORGANISM: Artificial Sequence
<220> FEATURE:
<223> OTHER INFORMATION: Synthetic peptide

<400> SEQUENCE: 166

Trp Ile Asn Thr Tyr Thr Gly Glu Pro Thr Tyr Ala Asp Lys Phe Gln
1               5                   10                  15

Gly

<210> SEQ ID NO 167
<211> LENGTH: 13
<212> TYPE: PRT
<213> ORGANISM: Artificial Sequence
<220> FEATURE:
<223> OTHER INFORMATION: Synthetic peptide

<400> SEQUENCE: 167

Trp Ser Trp Ser Asp Gly Tyr Tyr Val Tyr Phe Asp Tyr
1               5                   10

<210> SEQ ID NO 168
<211> LENGTH: 17
<212> TYPE: PRT
<213> ORGANISM: Artificial Sequence
<220> FEATURE:
<223> OTHER INFORMATION: Synthetic peptide

<400> SEQUENCE: 168

Lys Ser Ser Gln Ser Val Leu Asp Ser Ser Asn Asn Lys Asn Ser Leu
1               5                   10                  15

Ala

<210> SEQ ID NO 169
<211> LENGTH: 7
<212> TYPE: PRT
<213> ORGANISM: Artificial Sequence
<220> FEATURE:
<223> OTHER INFORMATION: Synthetic peptide

<400> SEQUENCE: 169

Trp Ala Ser Thr Arg Glu Ser
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic peptide

<400> SEQUENCE: 170

Gln Gln Ser Ala His Phe Pro Ile Thr
1               5

<210> SEQ ID NO 171
<211> LENGTH: 122
<212> TYPE: PRT
```

```
<213> ORGANISM: Artificial Sequence
<220> FEATURE:
<223> OTHER INFORMATION: Synthetic peptide

<400> SEQUENCE: 171
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Glu
1| | | |5| | | | |10| | | | |15|
|Ser|Val|Lys|Val|Ser|Cys|Lys|Ala|Ser|Gly|Tyr|Thr|Phe|Thr|Asn|Tyr
| | | |20| | | | |25| | | | |30| |
|Gly|Met|Asn|Trp|Val|Lys|Gln|Ala|Pro|Gly|Gln|Gly|Leu|Glu|Trp|Met
| | |35| | | | |40| | | | |45| | |
|Gly|Trp|Ile|Asn|Thr|Tyr|Thr|Gly|Glu|Pro|Thr|Tyr|Ala|Asp|Lys|Phe
|50| | | | |55| | | | |60| | | | |
|Gln|Gly|Arg|Val|Thr|Met|Thr|Thr|Asp|Thr|Ser|Thr|Ser|Thr|Ala|Tyr
65| | | | |70| | | | |75| | | | |80
|Met|Glu|Ile|Arg|Asn|Leu|Arg|Ser|Asp|Asp|Thr|Ala|Val|Tyr|Tyr|Cys
| | | | |85| | | | |90| | | | |95| |
|Ala|Arg|Trp|Ser|Trp|Ser|Asp|Gly|Tyr|Tyr|Val|Tyr|Phe|Asp|Tyr|Trp
| | | |100| | | | |105| | | | |110| | |
|Gly|Gln|Gly|Thr|Thr|Val|Thr|Val|Ser|Ser| | | | | | |
| | |115| | | | |120| | | | | | | | |

```
<210> SEQ ID NO 172
<211> LENGTH: 113
<212> TYPE: PRT
<213> ORGANISM: Artificial Sequence
<220> FEATURE:
<223> OTHER INFORMATION: Synthetic peptide

<400> SEQUENCE: 172
```

| | | | | | | | | | | | | | | |
|---|---|---|---|---|---|---|---|---|---|---|---|---|---|---|
|Asp|Ile|Val|Met|Thr|Gln|Ser|Pro|Asp|Ser|Leu|Thr|Val|Ser|Leu|Gly
1| | | |5| | | | |10| | | | |15|
|Glu|Arg|Thr|Thr|Ile|Asn|Cys|Lys|Ser|Ser|Gln|Ser|Val|Leu|Asp|Ser
| | | |20| | | | |25| | | | |30| |
|Ser|Asn|Asn|Lys|Asn|Ser|Leu|Ala|Trp|Tyr|Gln|Gln|Lys|Pro|Gly|Gln
| | |35| | | | |40| | | | |45| | |
|Pro|Pro|Lys|Leu|Leu|Leu|Ser|Trp|Ala|Ser|Thr|Arg|Glu|Ser|Gly|Ile
| |50| | | | |55| | | | |60| | | |
|Pro|Asp|Arg|Phe|Ser|Gly|Ser|Gly|Ser|Gly|Thr|Asp|Phe|Thr|Leu|Thr
65| | | | |70| | | | |75| | | | |80
|Ile|Asp|Gly|Leu|Gln|Pro|Glu|Asp|Ser|Ala|Thr|Tyr|Tyr|Cys|Gln|Gln
| | | |85| | | | |90| | | | |95| |
|Ser|Ala|His|Phe|Pro|Ile|Thr|Phe|Gly|Gln|Gly|Thr|Arg|Leu|Glu|Ile
| | |100| | | | |105| | | | |110| | |
|Lys| | | | | | | | | | | | | | | |

```
<210> SEQ ID NO 173
<211> LENGTH: 250
<212> TYPE: PRT
<213> ORGANISM: Artificial Sequence
<220> FEATURE:
<223> OTHER INFORMATION: Synthetic peptide

<400> SEQUENCE: 173
```

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Glu
1| | | |5| | | | |10| | | | |15|
|Ser|Val|Lys|Val|Ser|Cys|Lys|Ala|Ser|Gly|Tyr|Thr|Phe|Thr|Asn|Tyr
| | | |20| | | | |25| | | | |30| |

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Lys Phe
 50                  55                  60

Gln Gly Arg Val Thr Met Thr Thr Asp Thr Ser Thr Ser Thr Ala Tyr
 65                  70                  75                  80

Met Glu Ile Arg Asn Leu Arg Ser Asp Asp Thr Ala Val Tyr Tyr Cys
                 85                  90                  95

Ala Arg Trp Ser Trp Ser Asp Gly Tyr Tyr Val Tyr Phe Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Ser Asp Ile Val Met Thr Gln Ser
            130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Asn Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Gly Leu Gln Pro Glu
            210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 174
<211> LENGTH: 504
<212> TYPE: PRT
<213> ORGANISM: Artificial Sequence
<220> FEATURE:
<223> OTHER INFORMATION: Synthetic peptide

<400> SEQUENCE: 174

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Ser Gln Val
            115                 120                 125

Gln Leu Gln Gln Ser Gly Ala Glu Leu Val Arg Pro Gly Ser Ser Val
            130                 135                 140

-continued

```
Lys Ile Ser Cys Lys Ala Ser Gly Tyr Ala Phe Ser Ser Tyr Trp Met
145                 150                 155                 160
Asn Trp Val Lys Gln Arg Pro Gly Gln Gly Leu Glu Trp Ile Gly Gln
            165                 170                 175
Ile Trp Pro Gly Asp Gly Asp Thr Asn Tyr Asn Gly Lys Phe Lys Gly
        180                 185                 190
Lys Ala Thr Leu Thr Ala Asp Glu Ser Ser Thr Ala Tyr Met Gln
    195                 200                 205
Leu Ser Ser Leu Ala Ser Glu Asp Ser Ala Val Tyr Phe Cys Ala Arg
210                 215                 220
Arg Glu Thr Thr Thr Val Gly Arg Tyr Tyr Ala Met Asp Tyr Trp
225                 230                 235                 240
Gly Gln Gly Thr Thr Val Thr Val Ser Ser Gly Gly Gly Ser Asp
            245                 250                 255
Ile Lys Leu Gln Gln Ser Gly Ala Glu Leu Ala Arg Pro Gly Ala Ser
        260                 265                 270
Val Lys Met Ser Cys Lys Thr Ser Gly Tyr Thr Phe Thr Arg Tyr Thr
    275                 280                 285
Met His Trp Val Lys Gln Arg Pro Gly Gln Gly Leu Glu Trp Ile Gly
290                 295                 300
Tyr Ile Asn Pro Ser Arg Gly Tyr Thr Asn Tyr Asn Gln Lys Phe Lys
305                 310                 315                 320
Asp Lys Ala Thr Leu Thr Thr Asp Lys Ser Ser Thr Ala Tyr Met
            325                 330                 335
Gln Leu Ser Ser Leu Thr Ser Glu Asp Ser Ala Val Tyr Tyr Cys Ala
        340                 345                 350
Arg Tyr Tyr Asp Asp His Tyr Cys Leu Asp Tyr Trp Gly Gln Gly Thr
    355                 360                 365
Thr Leu Thr Val Ser Ser Val Glu Gly Gly Ser Gly Gly Ser Gly Gly
370                 375                 380
Ser Gly Gly Ser Gly Gly Val Asp Asp Ile Gln Leu Thr Gln Ser Pro
385                 390                 395                 400
Ala Ile Met Ser Ala Ser Pro Gly Glu Lys Val Thr Met Thr Cys Arg
            405                 410                 415
Ala Ser Ser Ser Val Ser Tyr Met Asn Trp Tyr Gln Gln Lys Ser Gly
        420                 425                 430
Thr Ser Pro Lys Arg Trp Ile Tyr Asp Thr Ser Lys Val Ala Ser Gly
    435                 440                 445
Val Pro Tyr Arg Phe Ser Gly Ser Gly Ser Gly Thr Ser Tyr Ser Leu
450                 455                 460
Thr Ile Ser Ser Met Glu Ala Glu Asp Ala Ala Thr Tyr Tyr Cys Gln
465                 470                 475                 480
Gln Trp Ser Ser Asn Pro Leu Thr Phe Gly Ala Gly Thr Lys Leu Glu
            485                 490                 495
Leu Lys His His His His His His
            500
```

<210> SEQ ID NO 175
<211> LENGTH: 1104
<212> TYPE: PRT
<213> ORGANISM: Artificial Sequence
<220> FEATURE:
<223> OTHER INFORMATION: Synthetic peptide

<400> SEQUENCE: 175

```
Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Met Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
```

```
            420                 425                 430
Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
            450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                    485                 490                 495

Gly Gly Gly Thr Lys Leu Thr Val Leu Pro Gly Gly Gly Ser Asp
                500                 505                 510

Ala His Lys Ser Glu Val Ala His Arg Phe Lys Asp Leu Gly Glu Glu
            515                 520                 525

Asn Phe Lys Ala Leu Val Leu Ile Ala Phe Ala Gln Tyr Leu Gln Gln
            530                 535                 540

Cys Pro Phe Glu Asp His Val Lys Leu Val Asn Glu Val Thr Glu Phe
545                 550                 555                 560

Ala Lys Thr Cys Val Ala Asp Glu Ser Ala Glu Asn Cys Asp Lys Ser
                565                 570                 575

Leu His Thr Leu Phe Gly Asp Lys Leu Cys Thr Val Ala Thr Leu Arg
            580                 585                 590

Glu Thr Tyr Gly Glu Met Ala Asp Cys Cys Ala Lys Gln Glu Pro Glu
            595                 600                 605

Arg Asn Glu Cys Phe Leu Gln His Lys Asp Asp Asn Pro Asn Leu Pro
            610                 615                 620

Arg Leu Val Arg Pro Glu Val Asp Val Met Cys Thr Ala Phe His Asp
625                 630                 635                 640

Asn Glu Glu Thr Phe Leu Lys Lys Tyr Leu Tyr Glu Ile Ala Arg Arg
                645                 650                 655

His Pro Tyr Phe Tyr Ala Pro Glu Leu Leu Phe Phe Ala Lys Arg Tyr
                660                 665                 670

Lys Ala Ala Phe Thr Glu Cys Cys Gln Ala Ala Asp Lys Ala Ala Cys
            675                 680                 685

Leu Leu Pro Lys Leu Asp Glu Leu Arg Asp Glu Gly Lys Ala Ser Ser
            690                 695                 700

Ala Lys Gln Arg Leu Lys Cys Ala Ser Leu Gln Lys Phe Gly Glu Arg
705                 710                 715                 720

Ala Phe Lys Ala Trp Ala Val Ala Arg Leu Ser Gln Arg Phe Pro Lys
                725                 730                 735

Ala Glu Phe Ala Glu Val Ser Lys Leu Val Thr Asp Leu Thr Lys Val
            740                 745                 750

His Thr Glu Cys Cys His Gly Asp Leu Leu Glu Cys Ala Asp Asp Arg
            755                 760                 765

Ala Asp Leu Ala Lys Tyr Ile Cys Glu Asn Gln Asp Ser Ile Ser Ser
770                 775                 780

Lys Leu Lys Glu Cys Cys Glu Lys Pro Leu Leu Glu Lys Ser His Cys
785                 790                 795                 800

Ile Ala Glu Val Glu Asn Asp Glu Met Pro Ala Asp Leu Pro Ser Leu
                805                 810                 815

Ala Ala Asp Phe Val Glu Ser Lys Asp Val Cys Lys Asn Tyr Ala Glu
            820                 825                 830

Ala Lys Asp Val Phe Leu Gly Met Phe Leu Tyr Glu Tyr Ala Arg Arg
            835                 840                 845
```

His Pro Asp Tyr Ser Val Val Leu Leu Arg Leu Ala Lys Thr Tyr
        850                 855                 860

Glu Thr Thr Leu Glu Lys Cys Cys Ala Ala Ala Asp Pro His Glu Cys
865                 870                 875                 880

Tyr Ala Lys Val Phe Asp Glu Phe Lys Pro Leu Val Glu Glu Pro Gln
                885                 890                 895

Asn Leu Ile Lys Gln Asn Cys Glu Leu Phe Glu Gln Leu Gly Glu Tyr
            900                 905                 910

Lys Phe Gln Asn Ala Leu Leu Val Arg Tyr Thr Lys Lys Val Pro Gln
        915                 920                 925

Val Ser Thr Pro Thr Leu Val Glu Val Ser Arg Asn Leu Gly Lys Val
    930                 935                 940

Gly Ser Lys Cys Cys Lys His Pro Glu Ala Lys Arg Met Pro Cys Ala
945                 950                 955                 960

Glu Asp Tyr Leu Ser Val Val Leu Asn Gln Leu Cys Val Leu His Glu
                965                 970                 975

Lys Thr Pro Val Ser Asp Arg Val Thr Lys Cys Cys Thr Glu Ser Leu
            980                 985                 990

Val Asn Arg Arg Pro Cys Phe Ser Ala Leu Glu Val Asp Glu Thr Tyr
        995                 1000                1005

Val Pro Lys Glu Phe Asn Ala Glu Thr Phe Thr Phe His Ala Asp
    1010                1015                1020

Ile Cys Thr Leu Ser Glu Lys Glu Arg Gln Ile Lys Lys Gln Thr
    1025                1030                1035

Ala Leu Val Glu Leu Val Lys His Lys Pro Lys Ala Thr Lys Glu
    1040                1045                1050

Gln Leu Lys Ala Val Met Asp Asp Phe Ala Ala Phe Val Glu Lys
    1055                1060                1065

Cys Cys Lys Ala Asp Asp Lys Glu Thr Cys Phe Ala Glu Glu Gly
    1070                1075                1080

Lys Lys Leu Val Ala Ala Ser Gln Ala Ala Leu Gly Leu Asp Tyr
    1085                1090                1095

His His His His His His
    1100

<210> SEQ ID NO 176
<211> LENGTH: 1093
<212> TYPE: PRT
<213> ORGANISM: Artificial Sequence
<220> FEATURE:
<223> OTHER INFORMATION: Synthetic peptide

<400> SEQUENCE: 176

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Ser Gly Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

```
Ala Arg Asp Arg Asn Ser His Phe Asp Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Asp Ile Gln Met Thr Gln Ser Pro Ser Ser Val Ser
            130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
            165                 170                 175

Lys Leu Leu Ile Tyr Gly Ala Ser Gly Leu Gln Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Ala Lys
            210                 215                 220

Ser Phe Pro Arg Thr Phe Gly Gln Gly Thr Lys Val Glu Ile Lys Ser
225                 230                 235                 240

Gly Gly Gly Gly Ser Glu Val Gln Leu Val Glu Ser Gly Gly Gly Leu
            245                 250                 255

Val Gln Pro Gly Gly Ser Leu Lys Leu Ser Cys Ala Ala Ser Gly Phe
            260                 265                 270

Thr Phe Asn Lys Tyr Ala Met Asn Trp Val Arg Gln Ala Pro Gly Lys
            275                 280                 285

Gly Leu Glu Trp Val Ala Arg Ile Arg Ser Lys Tyr Asn Asn Tyr Ala
            290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
            325                 330                 335

Asp Thr Ala Val Tyr Tyr Cys Val Arg His Gly Asn Phe Gly Asn Ser
            340                 345                 350

Tyr Ile Ser Tyr Trp Ala Tyr Trp Gly Gln Gly Thr Leu Val Thr Val
            355                 360                 365

Ser Ser Gly Gly Gly Gly Ser Gly Gly Gly Gly Ser Gly Gly Gly Gly
            370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
            405                 410                 415

Gly Asn Tyr Pro Asn Trp Val Gln Gln Lys Pro Gly Gln Ala Pro Arg
            420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
            450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Thr Lys Leu Thr Val Leu Pro Gly
            485                 490                 495

Gly Gly Gly Ser Asp Ala His Lys Ser Glu Val Ala His Arg Phe Lys
            500                 505                 510
```

```
Asp Leu Gly Glu Glu Asn Phe Lys Ala Leu Val Leu Ile Ala Phe Ala
        515                 520                 525

Gln Tyr Leu Gln Gln Cys Pro Phe Glu Asp His Val Lys Leu Val Asn
530                 535                 540

Glu Val Thr Glu Phe Ala Lys Thr Cys Val Ala Asp Glu Ser Ala Glu
545                 550                 555                 560

Asn Cys Asp Lys Ser Leu His Thr Leu Phe Gly Asp Lys Leu Cys Thr
                565                 570                 575

Val Ala Thr Leu Arg Glu Thr Tyr Gly Glu Met Ala Asp Cys Cys Ala
            580                 585                 590

Lys Gln Glu Pro Glu Arg Asn Glu Cys Phe Leu Gln His Lys Asp Asp
        595                 600                 605

Asn Pro Asn Leu Pro Arg Leu Val Arg Pro Glu Val Asp Val Met Cys
    610                 615                 620

Thr Ala Phe His Asp Asn Glu Glu Thr Phe Leu Lys Lys Tyr Leu Tyr
625                 630                 635                 640

Glu Ile Ala Arg Arg His Pro Tyr Phe Tyr Ala Pro Glu Leu Leu Phe
                645                 650                 655

Phe Ala Lys Arg Tyr Lys Ala Ala Phe Thr Glu Cys Cys Gln Ala Ala
            660                 665                 670

Asp Lys Ala Ala Cys Leu Leu Pro Lys Leu Asp Glu Leu Arg Asp Glu
        675                 680                 685

Gly Lys Ala Ser Ser Ala Lys Gln Arg Leu Lys Cys Ala Ser Leu Gln
    690                 695                 700

Lys Phe Gly Glu Arg Ala Phe Lys Ala Trp Ala Val Ala Arg Leu Ser
705                 710                 715                 720

Gln Arg Phe Pro Lys Ala Glu Phe Ala Glu Val Ser Lys Leu Val Thr
                725                 730                 735

Asp Leu Thr Lys Val His Thr Glu Cys Cys His Gly Asp Leu Leu Glu
            740                 745                 750

Cys Ala Asp Asp Arg Ala Asp Leu Ala Lys Tyr Ile Cys Glu Asn Gln
        755                 760                 765

Asp Ser Ile Ser Ser Lys Leu Lys Glu Cys Cys Glu Lys Pro Leu Leu
    770                 775                 780

Glu Lys Ser His Cys Ile Ala Glu Val Glu Asn Asp Glu Met Pro Ala
785                 790                 795                 800

Asp Leu Pro Ser Leu Ala Ala Asp Phe Val Glu Ser Lys Asp Val Cys
                805                 810                 815

Lys Asn Tyr Ala Glu Ala Lys Asp Val Phe Leu Gly Met Phe Leu Tyr
            820                 825                 830

Glu Tyr Ala Arg Arg His Pro Asp Tyr Ser Val Val Leu Leu Leu Arg
        835                 840                 845

Leu Ala Lys Thr Tyr Glu Thr Thr Leu Glu Lys Cys Cys Ala Ala Ala
    850                 855                 860

Asp Pro His Glu Cys Tyr Ala Lys Val Phe Asp Glu Phe Lys Pro Leu
865                 870                 875                 880

Val Glu Glu Pro Gln Asn Leu Ile Lys Gln Asn Cys Glu Leu Phe Glu
                885                 890                 895

Gln Leu Gly Glu Tyr Lys Phe Gln Asn Ala Leu Leu Val Arg Tyr Thr
            900                 905                 910

Lys Lys Val Pro Gln Val Ser Thr Pro Thr Leu Val Glu Val Ser Arg
        915                 920                 925

Asn Leu Gly Lys Val Gly Ser Lys Cys Cys Lys His Pro Glu Ala Lys
```

```
                930            935              940
Arg Met Pro Cys Ala Glu Asp Tyr Leu Ser Val Val Leu Asn Gln Leu
945                 950              955                 960

Cys Val Leu His Glu Lys Thr Pro Val Ser Asp Arg Val Thr Lys Cys
                965              970                 975

Cys Thr Glu Ser Leu Val Asn Arg Arg Pro Cys Phe Ser Ala Leu Glu
                980              985                 990

Val Asp Glu Thr Tyr Val Pro Lys Glu Phe Asn Ala Glu Thr Phe Thr
                995              1000                1005

Phe His Ala Asp Ile Cys Thr Leu Ser Glu Lys Glu Arg Gln Ile
    1010            1015                1020

Lys Lys Gln Thr Ala Leu Val Glu Leu Val Lys His Lys Pro Lys
    1025            1030                1035

Ala Thr Lys Glu Gln Leu Lys Ala Val Met Asp Asp Phe Ala Ala
    1040            1045                1050

Phe Val Glu Lys Cys Cys Lys Ala Asp Asp Lys Glu Thr Cys Phe
    1055            1060                1065

Ala Glu Glu Gly Lys Lys Leu Val Ala Ala Ser Gln Ala Ala Leu
    1070            1075                1080

Gly Leu Asp Tyr His His His His His His
    1085            1090
```

<210> SEQ ID NO 177
<211> LENGTH: 513
<212> TYPE: PRT
<213> ORGANISM: Artificial Sequence
<220> FEATURE:
<223> OTHER INFORMATION: Synthetic peptide

<400> SEQUENCE: 177

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala His Gly Gln Ser Leu Glu Trp Met
            35                  40                  45

Gly Gly Ile Asn Pro Asn Asn Gly Ile Pro Asn Tyr Asn Gln Lys Phe
        50                  55                  60

Lys Gly Arg Val Thr Ile Thr Val Asp Thr Ser Ala Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Ser Asp Ile Val Met Thr
    130                 135                 140

Gln Thr Pro Phe Ser Leu Pro Val Thr Pro Gly Glu Pro Ala Ser Ile
145                 150                 155                 160

Ser Cys Lys Ser Ser Gln Ser Leu Leu Tyr Ser Arg Asn Gln Lys Asn
                165                 170                 175

Tyr Leu Ala Trp Tyr Gln Gln Lys Pro Gly Gln Ser Pro Lys Leu Leu
            180                 185                 190

Ile Tyr Trp Ala Ser Thr Arg Glu Ser Gly Val Pro Asp Arg Phe Ser
```

```
                195                 200                 205
Gly Ser Gly Ser Gly Thr Asp Phe Thr Leu Lys Ile Ser Arg Val Glu
            210                 215                 220
Ala Glu Asp Val Gly Val Tyr Tyr Cys Gln Gln Tyr Phe Ser Tyr Pro
225                 230                 235                 240
Leu Thr Phe Gly Gly Gly Thr Lys Val Glu Ile Lys Ser Gly Gly Gly
                245                 250                 255
Gly Ser Glu Val Gln Leu Val Glu Ser Gly Gly Gly Leu Val Gln Pro
            260                 265                 270
Gly Gly Ser Leu Lys Leu Ser Cys Ala Ala Ser Gly Phe Thr Phe Asn
        275                 280                 285
Lys Tyr Ala Met Asn Trp Val Arg Gln Ala Pro Gly Lys Gly Leu Glu
        290                 295                 300
Trp Val Ala Arg Ile Arg Ser Lys Tyr Asn Asn Tyr Ala Thr Tyr Tyr
305                 310                 315                 320
Ala Asp Ser Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Gly Asn Phe Gly Asn Ser Tyr Ile Ser
        355                 360                 365
Tyr Trp Ala Tyr Trp Gly Gln Gly Thr Leu Val Thr Val Ser Ser Gly
        370                 375                 380
Gly Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Gly Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
        435                 440                 445
Gly Gly Thr Lys Phe Leu Ala Pro Gly Thr Pro Ala Arg Phe Ser Gly
        450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Val Leu Trp Tyr Ser Asn Arg Trp
                485                 490                 495
Val Phe Gly Gly Gly Thr Lys Leu Thr Val Leu His His His His His
            500                 505                 510
His

<210> SEQ ID NO 178
<211> LENGTH: 4
<212> TYPE: PRT
<213> ORGANISM: Artificial Sequence
<220> FEATURE:
<223> OTHER INFORMATION: Synthetic linker

<400> SEQUENCE: 178

Gly Gly Gly Ser
1

<210> SEQ ID NO 179
<211> LENGTH: 249
<212> TYPE: PRT
<213> ORGANISM: Artificial Sequence
```

<220> FEATURE:
<223> OTHER INFORMATION: Synthetic peptide

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 180
<211> LENGTH: 993
<212> TYPE: PRT
<213> ORGANISM: Artificial Sequence
<220> FEATURE:
<223> OTHER INFORMATION: Synthetic peptide

<400> SEQUENCE: 180

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys

```
                    85                  90                  95
Ala Arg Trp Ser Trp Ser Asp Gly Tyr Tyr Val Tyr Phe Asp Tyr Trp
                100                 105                 110

Gly Gln Gly Thr Ser Val Thr Val Ser Ser Gly Gly Gly Ser Gly
            115                 120                 125

Gly Gly Gly Ser Gly Gly Gly Ser Asp Ile Val Met Thr Gln Ser
        130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
        210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
        290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
        370                 375                 380

Gly Ser Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
        450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu Gly Gly Gly Gly Asp Lys Thr
            500                 505                 510
```

His Thr Cys Pro Pro Cys Pro Ala Pro Glu Leu Leu Gly Gly Pro Ser
            515                 520                 525

Val Phe Leu Phe Pro Pro Lys Pro Lys Asp Thr Leu Met Ile Ser Arg
    530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
                565                 570                 575

Lys Thr Lys Pro Cys Glu Glu Gln Tyr Gly Ser Thr Tyr Arg Cys Val
                580                 585                 590

Ser Val Leu Thr Val Leu His Gln Asp Trp Leu Asn Gly Lys Glu Tyr
            595                 600                 605

Lys Cys Lys Val Ser Asn Lys Ala Leu Pro Ala Pro Ile Glu Lys Thr
        610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
                645                 650                 655

Leu Val Lys Gly Phe Tyr Pro Ser Asp Ile Ala Val Glu Trp Glu Ser
            660                 665                 670

Asn Gly Gln Pro Glu Asn Asn Tyr Lys Thr Thr Pro Pro Val Leu Asp
        675                 680                 685

Ser Asp Gly Ser Phe Phe Leu Tyr Ser Lys Leu Thr Val Asp Lys Ser
    690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
                725                 730                 735

Gly Gly Gly Gly Ser Gly Gly Gly Ser Gly Gly Gly Gly Ser Gly
            740                 745                 750

Gly Gly Ser Gly Gly Gly Ser Gly Gly Gly Ser Asp Lys
        755                 760                 765

Thr His Thr Cys Pro Pro Cys Pro Ala Pro Glu Leu Leu Gly Gly Pro
    770                 775                 780

Ser Val Phe Leu Phe Pro Pro Lys Pro Lys Asp Thr Leu Met Ile Ser
785                 790                 795                 800

Arg Thr Pro Glu Val Thr Cys Val Val Val Asp Val Ser His Glu Asp
                805                 810                 815

Pro Glu Val Lys Phe Asn Trp Tyr Val Asp Gly Val Glu Val His Asn
            820                 825                 830

Ala Lys Thr Lys Pro Cys Glu Glu Gln Tyr Gly Ser Thr Tyr Arg Cys
        835                 840                 845

Val Ser Val Leu Thr Val Leu His Gln Asp Trp Leu Asn Gly Lys Glu
    850                 855                 860

Tyr Lys Cys Lys Val Ser Asn Lys Ala Leu Pro Ala Pro Ile Glu Lys
865                 870                 875                 880

Thr Ile Ser Lys Ala Lys Gly Gln Pro Arg Glu Pro Gln Val Tyr Thr
                885                 890                 895

Leu Pro Pro Ser Arg Glu Glu Met Thr Lys Asn Gln Val Ser Leu Thr
            900                 905                 910

Cys Leu Val Lys Gly Phe Tyr Pro Ser Asp Ile Ala Val Glu Trp Glu
        915                 920                 925

Ser Asn Gly Gln Pro Glu Asn Asn Tyr Lys Thr Thr Pro Pro Val Leu
        930                 935                 940

Asp Ser Asp Gly Ser Phe Phe Leu Tyr Ser Lys Leu Thr Val Asp Lys
945                 950                 955                 960

Ser Arg Trp Gln Gln Gly Asn Val Phe Ser Cys Ser Val Met His Glu
                965                 970                 975

Ala Leu His Asn His Tyr Thr Gln Lys Ser Leu Ser Leu Ser Pro Gly
                980                 985                 990

Lys

<210> SEQ ID NO 181
<211> LENGTH: 246
<212> TYPE: PRT
<213> ORGANISM: Artificial Sequence
<220> FEATURE:
<223> OTHER INFORMATION: Synthetic peptide

<400> SEQUENCE: 181

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
                20                  25                  30

Arg Met Gly Val Ser Trp Ile Arg Gln Pro Pro Gly Lys Cys Leu Glu
            35                  40                  45

Trp Leu Ala His Ile Phe Ser Asn Asp Glu Lys Ser Tyr Ser Thr Ser
        50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
                85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
                165                 170                 175

Gln Lys Pro Gly Lys Ala Pro Lys Arg Leu Ile Tyr Ala Ala Ser Thr
            180                 185                 190

Leu Gln Ser Gly Val Pro Ser Arg Phe Ser Gly Ser Gly Ser Gly Thr
        195                 200                 205

Glu Phe Thr Leu Thr Ile Ser Ser Leu Gln Pro Glu Asp Phe Ala Thr
210                 215                 220

Tyr Tyr Cys Leu Gln His Asn Ser Tyr Pro Leu Thr Phe Gly Cys Gly
225                 230                 235                 240

Thr Lys Val Glu Ile Lys
                245

<210> SEQ ID NO 182
<211> LENGTH: 989
<212> TYPE: PRT
<213> ORGANISM: Artificial Sequence
<220> FEATURE:
<223> OTHER INFORMATION: Synthetic peptide

<400> SEQUENCE: 182

```
Gln Val Thr Leu Lys Glu Ser Gly Pro Thr Leu Val Lys Pro Thr Glu
1               5                   10                  15
Thr Leu Thr Leu Thr Cys Thr Leu Ser Gly Phe Ser Leu Asn Asn Ala
            20                  25                  30
Arg Met Gly Val Ser Trp Ile Arg Gln Pro Pro Gly Lys Cys Leu Glu
        35                  40                  45
Trp Leu Ala His Ile Phe Ser Asn Asp Glu Lys Ser Tyr Ser Thr Ser
    50                  55                  60
Leu Lys Asn Arg Leu Thr Ile Ser Lys Asp Ser Ser Lys Thr Gln Val
65                  70                  75                  80
Val Leu Thr Met Thr Asn Val Asp Pro Val Asp Thr Ala Thr Tyr Tyr
                85                  90                  95
Cys Ala Arg Ile Val Gly Tyr Gly Ser Gly Trp Tyr Gly Phe Phe Asp
            100                 105                 110
Tyr Trp Gly Gln Gly Thr Leu Val Thr Val Ser Ser Gly Gly Gly Gly
        115                 120                 125
Ser Gly Gly Gly Gly Ser Gly Gly Gly Ser Asp Ile Gln Met Thr
    130                 135                 140
Gln Ser Pro Ser Ser Leu Ser Ala Ser Val Gly Asp Arg Val Thr Ile
145                 150                 155                 160
Thr Cys Arg Ala Ser Gln Gly Ile Arg Asn Asp Leu Gly Trp Tyr Gln
                165                 170                 175
Gln Lys Pro Gly Lys Ala Pro Lys Arg Leu Ile Tyr Ala Ala Ser Thr
            180                 185                 190
Leu Gln Ser Gly Val Pro Ser Arg Phe Ser Gly Ser Gly Ser Gly Thr
        195                 200                 205
Glu Phe Thr Leu Thr Ile Ser Ser Leu Gln Pro Glu Asp Phe Ala Thr
    210                 215                 220
Tyr Tyr Cys Leu Gln His Asn Ser Tyr Pro Leu Thr Phe Gly Cys Gly
225                 230                 235                 240
Thr Lys Val Glu Ile Lys Ser Gly Gly Gly Gly Ser Glu Val Gln Leu
                245                 250                 255
Val Glu Ser Gly Gly Gly Leu Val Gln Pro Gly Gly Ser Leu Lys Leu
            260                 265                 270
Ser Cys Ala Ala Ser Gly Phe Thr Phe Asn Lys Tyr Ala Met Asn Trp
        275                 280                 285
Val Arg Gln Ala Pro Gly Lys Gly Leu Glu Trp Val Ala Arg Ile Arg
    290                 295                 300
Ser Lys Tyr Asn Asn Tyr Ala Thr Tyr Tyr Ala Asp Ser Val Lys Asp
305                 310                 315                 320
Arg Phe Thr Ile Ser Arg Asp Asp Ser Lys Asn Thr Ala Tyr Leu Gln
                325                 330                 335
Met Asn Asn Leu Lys Thr Glu Asp Thr Ala Val Tyr Tyr Cys Val Arg
            340                 345                 350
His Gly Asn Phe Gly Asn Ser Tyr Ile Ser Tyr Trp Ala Tyr Trp Gly
        355                 360                 365
Gln Gly Thr Leu Val Thr Val Ser Ser Gly Gly Gly Gly Ser Gly Gly
    370                 375                 380
Gly Gly Ser Gly Gly Gly Gly Ser Gln Thr Val Val Thr Gln Glu Pro
385                 390                 395                 400
Ser Leu Thr Val Ser Pro Gly Gly Thr Val Thr Leu Thr Cys Gly Ser
```

-continued

```
                405                 410                 415
Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu Gly Gly Gly Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
    530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
    610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
        675                 680                 685

Phe Phe Leu Tyr Ser Lys Leu Thr Val Asp Lys Ser Arg Trp Gln Gln
    690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
                725                 730                 735

Ser Gly Gly Gly Gly Ser Gly Gly Gly Ser Gly Gly Gly Gly Ser
            740                 745                 750

Gly Gly Gly Gly Ser Gly Gly Gly Ser Asp Lys Thr His Thr Cys
        755                 760                 765

Pro Pro Cys Pro Ala Pro Glu Leu Leu Gly Gly Pro Ser Val Phe Leu
    770                 775                 780

Phe Pro Pro Lys Pro Lys Asp Thr Leu Met Ile Ser Arg Thr Pro Glu
785                 790                 795                 800

Val Thr Cys Val Val Val Asp Val Ser His Glu Asp Pro Glu Val Lys
                805                 810                 815

Phe Asn Trp Tyr Val Asp Gly Val Glu Val His Asn Ala Lys Thr Lys
            820                 825                 830
```

```
Pro Cys Glu Glu Gln Tyr Gly Ser Thr Tyr Arg Cys Val Ser Val Leu
            835                 840                 845

Thr Val Leu His Gln Asp Trp Leu Asn Gly Lys Glu Tyr Lys Cys Lys
850                 855                 860

Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
            900                 905                 910

Gly Phe Tyr Pro Ser Asp Ile Ala Val Glu Trp Glu Ser Asn Gly Gln
            915                 920                 925

Pro Glu Asn Asn Tyr Lys Thr Thr Pro Pro Val Leu Asp Ser Asp Gly
            930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 183
<211> LENGTH: 246
<212> TYPE: PRT
<213> ORGANISM: Artificial Sequence
<220> FEATURE:
<223> OTHER INFORMATION: Synthetic peptide

<400> SEQUENCE: 183

Gln Val Thr Leu Lys Glu Ser Gly Pro Ala Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Ala Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Glu Asp Thr Ala Thr Tyr Tyr
                85                  90                  95

Cys Ala Arg Ile Val Gly Tyr Gly Thr Gly Trp Tyr Gly Phe Phe Asp
            100                 105                 110

Tyr Trp Gly Gln Gly Ile Leu Val Thr Val Ser Ser Gly Gly Gly Gly
        115                 120                 125

Ser Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Ala Trp Tyr Gln
                165                 170                 175

Gln Lys Pro Gly Lys Ala Pro Lys Arg Leu Ile Tyr Ala Ala Ser Ser
            180                 185                 190

Leu Gln Ser Gly Val Pro Ser Arg Phe Ser Gly Ser Gly Ser Gly Thr
        195                 200                 205
```

Glu Phe Thr Leu Thr Ile Ser Ser Leu Gln Pro Glu Asp Phe Ala Thr
    210                 215                 220

Tyr Tyr Cys Leu Gln His Asn Ser Tyr Pro Leu Thr Phe Gly Cys Gly
225                 230                 235                 240

Thr Lys Val Glu Ile Lys
            245

<210> SEQ ID NO 184
<211> LENGTH: 989
<212> TYPE: PRT
<213> ORGANISM: Artificial Sequence
<220> FEATURE:
<223> OTHER INFORMATION: Synthetic peptide

<400> SEQUENCE: 184

Gln Val Thr Leu Lys Glu Ser Gly Pro Ala Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Ala Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Glu Asp Thr Ala Thr Tyr Tyr
                85                  90                  95

Cys Ala Arg Ile Val Gly Tyr Gly Thr Gly Trp Tyr Gly Phe Phe Asp
            100                 105                 110

Tyr Trp Gly Gln Gly Ile Leu Val Thr Val Ser Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Ala Trp Tyr Gln
                165                 170                 175

Gln Lys Pro Gly Lys Ala Pro Lys Arg Leu Ile Tyr Ala Ala Ser Ser
            180                 185                 190

Leu Gln Ser Gly Val Pro Ser Arg Phe Ser Gly Ser Gly Ser Gly Thr
        195                 200                 205

Glu Phe Thr Leu Thr Ile Ser Ser Leu Gln Pro Glu Asp Phe Ala Thr
    210                 215                 220

Tyr Tyr Cys Leu Gln His Asn Ser Tyr Pro Leu Thr Phe Gly Cys Gly
225                 230                 235                 240

Thr Lys Val Glu Ile Lys Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

```
Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Ser Gly Gly
            370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
            405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Ala Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
            485                 490                 495

Lys Leu Thr Val Leu Gly Gly Gly Asp Lys Thr His Thr Cys Pro
            500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
            530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
            565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
            610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
            645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
            675                 680                 685

Phe Phe Leu Tyr Ser Lys Leu Thr Val Asp Lys Ser Arg Trp Gln Gln
            690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
            725                 730                 735
```

Ser Gly Gly Gly Gly Ser Gly Gly Gly Ser Gly Gly Gly Ser
            740                 745                 750

Gly Gly Gly Gly Ser Gly Gly Gly Ser Asp Lys Thr His Thr Cys
            755                 760                 765

Pro Pro Cys Pro Ala Pro Glu Leu Leu Gly Gly Pro Ser Val Phe Leu
            770                 775                 780

Phe Pro Pro Lys Pro Lys Asp Thr Leu Met Ile Ser Arg Thr Pro Glu
785                 790                 795                 800

Val Thr Cys Val Val Val Asp Val Ser His Glu Asp Pro Glu Val Lys
                805                 810                 815

Phe Asn Trp Tyr Val Asp Gly Val Glu Val His Asn Ala Lys Thr Lys
                820                 825                 830

Pro Cys Glu Glu Gln Tyr Gly Ser Thr Tyr Arg Cys Val Ser Val Leu
                835                 840                 845

Thr Val Leu His Gln Asp Trp Leu Asn Gly Lys Glu Tyr Lys Cys Lys
            850                 855                 860

Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
                900                 905                 910

Gly Phe Tyr Pro Ser Asp Ile Ala Val Glu Trp Glu Ser Asn Gly Gln
            915                 920                 925

Pro Glu Asn Asn Tyr Lys Thr Thr Pro Pro Val Leu Asp Ser Asp Gly
930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 185
<211> LENGTH: 243
<212> TYPE: PRT
<213> ORGANISM: Artificial Sequence
<220> FEATURE:
<223> OTHER INFORMATION: Synthetic peptide

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
                20                  25                  30

Ile Ile His Trp Val Arg Gln Ala Pro Gly Gln Cys Leu Glu Trp Met
            35                  40                  45

Gly Tyr Ile Asn Pro Tyr Pro Gly Tyr His Ala Tyr Asn Glu Lys Phe
        50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

```
Gln Gly Thr Leu Val Thr Val Ser Ser Gly Gly Gly Ser Gly Gly
            115                 120                 125

Gly Gly Ser Gly Gly Gly Gly Ser Asp Ile Gln Met Thr Gln Ser Pro
        130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
            195                 200                 205

Phe Thr Ile Ser Ser Leu Glu Pro Glu Asp Ile Ala Thr Tyr Tyr Cys
        210                 215                 220

Gln Gln Gly Asn Thr Leu Pro Trp Thr Phe Gly Cys Gly Thr Lys Leu
225                 230                 235                 240

Glu Ile Lys

<210> SEQ ID NO 186
<211> LENGTH: 986
<212> TYPE: PRT
<213> ORGANISM: Artificial Sequence
<220> FEATURE:
<223> OTHER INFORMATION: Synthetic peptide

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Gly Ser Asp Ile Gln Met Thr Gln Ser Pro
        130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
            195                 200                 205

Phe Thr Ile Ser Ser Leu Glu Pro Glu Asp Ile Ala Thr Tyr Tyr Cys
        210                 215                 220

Gln Gln Gly Asn Thr Leu Pro Trp Thr Phe Gly Cys Gly Thr Lys Leu
```

-continued

```
                225                 230                 235                 240
        Glu Ile Lys Ser Gly Gly Gly Ser Glu Val Gln Leu Val Glu Ser
                        245                 250                 255
        Gly Gly Gly Leu Val Gln Pro Gly Gly Ser Leu Lys Leu Ser Cys Ala
                        260                 265                 270
        Ala Ser Gly Phe Thr Phe Asn Lys Tyr Ala Met Asn Trp Val Arg Gln
                        275                 280                 285
        Ala Pro Gly Lys Gly Leu Glu Trp Val Ala Arg Ile Arg Ser Lys Tyr
                        290                 295                 300
        Asn Asn Tyr Ala Thr Tyr Tyr Ala Asp Ser Val Lys Asp Arg Phe Thr
        305                 310                 315                 320
        Ile Ser Arg Asp Asp Ser Lys Asn Thr Ala Tyr Leu Gln Met Asn Asn
                        325                 330                 335
        Leu Lys Thr Glu Asp Thr Ala Val Tyr Tyr Cys Val Arg His Gly Asn
                        340                 345                 350
        Phe Gly Asn Ser Tyr Ile Ser Tyr Trp Ala Tyr Trp Gly Gln Gly Thr
                        355                 360                 365
        Leu Val Thr Val Ser Ser Gly Gly Gly Gly Ser Gly Gly Gly Gly Ser
                        370                 375                 380
        Gly Gly Gly Gly Ser Gln Thr Val Val Thr Gln Glu Pro Ser Leu Thr
        385                 390                 395                 400
        Val Ser Pro Gly Gly Thr Val Thr Leu Thr Cys Gly Ser Ser Thr Gly
                        405                 410                 415
        Ala Val Thr Ser Gly Asn Tyr Pro Asn Trp Val Gln Gln Lys Pro Gly
                        420                 425                 430
        Gln Ala Pro Arg Gly Leu Ile Gly Gly Thr Lys Phe Leu Ala Pro Gly
                        435                 440                 445
        Thr Pro Ala Arg Phe Ser Gly Ser Leu Leu Gly Gly Lys Ala Ala Leu
                        450                 455                 460
        Thr Leu Ser Gly Val Gln Pro Glu Asp Glu Ala Glu Tyr Tyr Cys Val
        465                 470                 475                 480
        Leu Trp Tyr Ser Asn Arg Trp Val Phe Gly Gly Gly Thr Lys Leu Thr
                        485                 490                 495
        Val Leu Gly Gly Gly Gly Asp Lys Thr His Thr Cys Pro Pro Cys Pro
                        500                 505                 510
        Ala Pro Glu Leu Leu Gly Gly Pro Ser Val Phe Leu Phe Pro Pro Lys
                        515                 520                 525
        Pro Lys Asp Thr Leu Met Ile Ser Arg Thr Pro Glu Val Thr Cys Val
        530                 535                 540
        Val Val Asp Val Ser His Glu Asp Pro Glu Val Lys Phe Asn Trp Tyr
        545                 550                 555                 560
        Val Asp Gly Val Glu Val His Asn Ala Lys Thr Lys Pro Cys Glu Glu
                        565                 570                 575
        Gln Tyr Gly Ser Thr Tyr Arg Cys Val Ser Val Leu Thr Val Leu His
                        580                 585                 590
        Gln Asp Trp Leu Asn Gly Lys Glu Tyr Lys Cys Lys Val Ser Asn Lys
                        595                 600                 605
        Ala Leu Pro Ala Pro Ile Glu Lys Thr Ile Ser Lys Ala Lys Gly Gln
                        610                 615                 620
        Pro Arg Glu Pro Gln Val Tyr Thr Leu Pro Pro Ser Arg Glu Glu Met
        625                 630                 635                 640
        Thr Lys Asn Gln Val Ser Leu Thr Cys Leu Val Lys Gly Phe Tyr Pro
                        645                 650                 655
```

Ser Asp Ile Ala Val Glu Trp Glu Ser Asn Gly Gln Pro Glu Asn Asn
         660                 665                 670

Tyr Lys Thr Thr Pro Pro Val Leu Asp Ser Asp Gly Ser Phe Phe Leu
     675                 680                 685

Tyr Ser Lys Leu Thr Val Asp Lys Ser Arg Trp Gln Gln Gly Asn Val
 690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly Gly
             725                 730                 735

Gly Gly Ser Gly Gly Gly Ser Gly Gly Gly Ser Gly Gly Gly
             740                 745                 750

Gly Ser Gly Gly Gly Ser Asp Lys Thr His Thr Cys Pro Pro Cys
         755                 760                 765

Pro Ala Pro Glu Leu Leu Gly Gly Pro Ser Val Phe Leu Phe Pro Pro
     770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                 805                 810                 815

Tyr Val Asp Gly Val Glu Val His Asn Ala Lys Thr Lys Pro Cys Glu
             820                 825                 830

Glu Gln Tyr Gly Ser Thr Tyr Arg Cys Val Ser Val Leu Thr Val Leu
         835                 840                 845

His Gln Asp Trp Leu Asn Gly Lys Glu Tyr Lys Cys Lys Val Ser Asn
     850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                 885                 890                 895

Met Thr Lys Asn Gln Val Ser Leu Thr Cys Leu Val Lys Gly Phe Tyr
             900                 905                 910

Pro Ser Asp Ile Ala Val Glu Trp Glu Ser Asn Gly Gln Pro Glu Asn
         915                 920                 925

Asn Tyr Lys Thr Thr Pro Pro Val Leu Asp Ser Asp Gly Ser Phe Phe
     930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                 965                 970                 975

Gln Lys Ser Leu Ser Leu Ser Pro Gly Lys
             980                 985

<210> SEQ ID NO 187
<211> LENGTH: 243
<212> TYPE: PRT
<213> ORGANISM: Artificial Sequence
<220> FEATURE:
<223> OTHER INFORMATION: Synthetic peptide

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
             20                  25                  30

Ile Ile His Trp Val Arg Gln Ala Pro Gly Gln Gly Leu Glu Trp Met
            35                  40                  45

Gly Tyr Ile Asn Pro Tyr Pro Gly Tyr His Ala Tyr Asn Glu Lys Phe
 50                  55                  60

Gln Gly Arg Ala Thr Met Thr Ser Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
            130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
            195                 200                 205

Phe Thr Ile Ser Ser Leu Glu Pro Glu Asp Ile Ala Thr Tyr Tyr Cys
            210                 215                 220

Gln Gln Gly Asn Thr Leu Pro Trp Thr Phe Gly Gln Gly Thr Lys Leu
225                 230                 235                 240

Glu Ile Lys

<210> SEQ ID NO 188
<211> LENGTH: 986
<212> TYPE: PRT
<213> ORGANISM: Artificial Sequence
<220> FEATURE:
<223> OTHER INFORMATION: Synthetic peptide

<400> SEQUENCE: 188

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Gly Leu Glu Trp Met
            35                  40                  45

Gly Tyr Ile Asn Pro Tyr Pro Gly Tyr His Ala Tyr Asn Glu Lys Phe
 50                  55                  60

Gln Gly Arg Ala Thr Met Thr Ser Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
            130                 135                 140

-continued

```
Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
            165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
            195                 200                 205

Phe Thr Ile Ser Ser Leu Glu Pro Glu Asp Ile Ala Thr Tyr Tyr Cys
210                 215                 220

Gln Gln Gly Asn Thr Leu Pro Trp Thr Phe Gly Gln Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
            530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
```

-continued

```
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
            645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
            690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
            725                 730                 735

Gly Gly Ser Gly Gly Gly Gly Ser Gly Gly Gly Gly Ser Gly Gly Gly
            740                 745                 750

Gly Ser Gly Gly Gly Ser Asp Lys Thr His Thr Cys Pro Pro Cys
            755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
            805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
            835                 840                 845

His Gln Asp Trp Leu Asn Gly Lys Glu Tyr Lys Cys Lys Val Ser Asn
850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
            885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
            915                 920                 925

Asn Tyr Lys Thr Thr Pro Pro Val Leu Asp Ser Asp Gly Ser Phe Phe
            930                 935                 940
```

```
Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965              970             975

Gln Lys Ser Leu Ser Leu Ser Pro Gly Lys
            980             985
```

PHARMACEUTICAL COMPOSITION COMPRISING BISPECIFIC ANTIBODY CONSTRUCTS

BACKGROUND

The advent of recombinant DNA technology has allowed the development of many protein pharmaceuticals in the past three decades. Protein-based pharmaceuticals are now among the fastest growing categories of therapeutic agents in (pre)clinical development and as commercial products. In comparison with small chemical drugs, protein pharmaceuticals have high specificity and activity at relatively low concentrations, and typically provide for therapy of high impact diseases such as various cancers, auto-immune diseases, and metabolic disorders (Roberts, *Trends Biotechnol.* 2014 July; 32(7):372-80, Wang, *Int J Pharm.* 1999 Aug. 20; 185(2):129-88).

Due to advances in commercial scale purification processes, recombinant proteins can now be obtained in high purity when first manufactured. However, proteins are only marginally stable and are highly susceptible to degradation, both chemical and physical. Chemical degradation refers to modifications involving covalent bonds, such as deamidation, oxidation, cleavage or formation of new disulfide bridges, hydrolysis, isomerization, or deglycosylation. Physical degradation includes protein unfolding, undesirable adsorption to surfaces, and aggregation. Dealing with these physical and chemical instabilities is one of the most challenging tasks in the development of protein pharmaceuticals (Chi et al., *Pharm Res*, Vol. 20, No. 9, September 2003, pp. 1325-1336, Roberts, *Trends Biotechnol.* 2014 July; 32(7):372-80).

Protein aggregation represents a major event of physical instability of proteins and occurs due to the inherent tendency to minimize the thermodynamically unfavorable interaction between the solvent and hydrophobic protein residues. It is particularly problematic because it is encountered routinely during refolding, purification, sterilization, shipping, and storage processes. Aggregation can occur even under solution conditions where the protein native state is highly thermodynamically favored (e.g., neutral pH and 37° C.) and in the absence of stresses (Chi et al., *Pharm Res*, Vol. 20, No. 9, September 2003, pp. 1325-1336, Roberts, *Trends Biotechnol.* 2014 July; 32(7):372-80, Wang, *Int J Pharm.* 1999 Aug. 20; 185(2):129-88, Mahler *J Pharm Sci.* 2009 September; 98(9):2909-34).

Protein aggregation is problematic because it can impair biological activity of the therapeutic proteins. Moreover, aggregation of proteins leads to undesirable aesthetics of the drug product, and decreases product yield due to elaborate purification steps that are required to remove the aggregates from the end product. More recently, there has also been growing concern and evidence that the presence of aggregated proteins (even humanized or fully human proteins) can significantly increase the risk that a patient will develop an immune response to the active protein monomer, resulting in the formation of neutralizing antibodies and drug resistance, or other adverse side effects (Mahler *J Pharm Sci.* 2009 September; 98(9):2909-34.

Several efforts have been reported in the literature to minimize protein aggregation by various mechanisms. Proteins can be stabilized and thus protected from aggregate formation and other chemical changes by modifying their primary structure, thereby increasing interior hydrophobicity and reducing outer hydrophobicity. However, genetic engineering of proteins may result in impaired functionality and/or increased immunogenicity. Another approach focuses on the dissociation of aggregates (referred to as "disaggregation") to recover functional, native monomers by using various mechanisms such as temperature, pressure, pH, and salts. Currently, protein aggregates are removed as impurities mainly in the polishing steps of downstream processing. However, in cases of high levels of high-molecular weight (HMW), removing significant amount of HMW not only results in substantial yield loss but also makes the design of a robust downstream process challenging (Chi et al., *Pharm Res*, Vol. 20, No. 9, September 2003, pp. 1325-1336).

Preserving protein stability and activity in biological and biotechnological applications poses serious challenges. There is a need in the art for optimized pharmaceutical compositions that provide for enhanced stabilization of therapeutic proteins and reduce aggregation and denaturation during formulation, filling, shipping, storage and administration, thereby preventing loss-of-function and adverse immunogenic reactions. It is the object of the present invention to comply with thus need.

SUMMARY

Protein instability, and in particular protein aggregation, is an increasing challenge in the biotechnology industry, where aggregation is encountered throughout the lifetime of a therapeutic protein, including during refolding, purification, sterilization, shipping, and storage processes. It is thus the object of the present invention to provide a stable pharmaceutical composition comprising a bispecific single chain antibody construct, binding to a target cell surface antigen via a first binding domain and to the T cell surface antigen CD3 via a second binding domain; a β-cyclodextrin; and a buffer.

The β-cyclodextrin may be present in a selected from the group consisting of β-cyclodextrin, methyl-β-cyclodextrin, hydroxyethyl-β-cyclodextrin, hydroxypropyl-β-cyclodextrin, ethyl-β-cyclodextrin, butyl-β-cyclodextrin Succinyl-(2-hydroxypropyl)-β-cyclodextrin, heptakis(2,3,6-tri-O-methyl)-β-cyclodextrin, heptakis(2,3,6-tri-O-benzoyl)-β-cyclodextrin, β-cyclodextrin phosphate sodium salt, β-cyclodextrin sulphate sodium salt, triacetyl-β-cyclodextrin, heptakis(6-O-sulfo)-β-cyclodextrin heptasodium salt, carboxymethyl-β-cyclodextrin sodium salt, sulfobutylether-β-cyclodextrin sodium salt, 6-O-β-toluenesulfonyl-β-cyclodextrin, and in particular from sulfobutylether-β-cyclodextrin sodium salt, hydroxypropyl-β-cyclodextrin. It may be present in a concentration in the range of 0.1% to 20% (w/v), preferably of 0.5% to 2% (w/v) and more preferably of 0.8% to 1.5% (w/v).

The bispecific single chain antibody construct may be present in a concentration range of 0.1-5 mg/ml, preferably of 0.2-2.5 mg/ml, more preferably of 0.25-1.0 mg/ml. Its first binding domain may bind to CD33. In particular, the amino acid sequence of the first binding domain of the bispecific single chain construct is selected form the group consisting of SEQ ID 99, 109, 119, 128, 137, 146, 155, 164 and 173 and the amino acid sequence of the second binding domain of the bispecific single chain construct is selected form the group consisting of SEQ ID NO: 9, 18, 27, 36, 45, 54, 63, 72, 81, 179 and 90.

The buffer may be selected from the group consisting of potassium phosphate, acetic acid/sodium acetate, citric acid/sodium citrate, succinic acid/sodium succinate, tartaric acid/sodium tartrate, histidine/histidine HCl, glycine, Tris, glutamate, acetate and mixtures thereof, and in particular from potassium phosphate, citric acid/sodium citrate, succinic acid, histidine, glutamate, acetate and combinations thereof.

The pH of the pharmaceutical composition may be in the range of 4 to 7.5.

One or more excipients may be present in the pharmaceutical composition provided herein, including sucrose, trehalose, mannitol, sorbitol, arginine, lysine, polysorbate 20, polysorbate 80, poloxamer 188, pluronic and combinations thereof.

The composition may comprise one or more preservatives, particularly benzyl alcohol, chlorobutanol, phenol, meta-cresol, methylparaben, phenoxyethanol, propylparaben thiomerosal. The structure and typical concentration for the use of these preservatives are described in Table 1 of Meyer et al. J Pharm Sci. 96(12), 3155.

Also provided herein is a pharmaceutical composition free of preservatives, comprising a bispecific single chain antibody construct having the amino acid sequence of SEQ ID NO: 100 or 110 and being in a concentration of about 0.5 mg/ml, and further a cyclodextrin being sulfobutylether-β-cyclodextrin sodium salt in a concentration of about 1% (w/v), and further a buffer being potassium phosphate in concentration of about 10 mM, said formulation further comprising sucrose in concentration of about 8% (w/v) of and polysorbate 80 in concentration of about 0.01% (w/v) at a pH of about 6.0.

DESCRIPTION OF THE FIGURES

FIG. 12A: Summary of maximal AMG 330 concentrations achieved by overconcentration, calculated by SEC mainpeak+HMW. SBE-β-CD formulations (indicated by asterisks) reached higher concentrations and maintained higher % monomer. FIG. 12B: Data from the same experiment as shown in FIG. 12A where AMG 330 was concentrated up to 7-8 mg/mL in the presence of increasing concentrations of SBE-β-CD with or without glycine and sucrose (see asterisks). The control on the left was concentrated without SBE-β-CD. The control on the right was not concentrated beyond its starting concentration of 0.4 mg/ml. Additional sample labeled as '2% Glycine, 1% Sucrose" was concentrated without SBE-β-CD to demonstrate the advantage of using SBE-β-CD. FIG. 12C: AMG 330 CEX relative peak areas after 5 days incubation at 4° C., average of two replicates. All samples contain 20 mM citrate, 0.01% PS-80, pH 6.0. FIG. 12D: AMG 330 relative main peak area after SEC analysis. All samples also include 20 mM Citrate, 0.01% PS-80, pH 6.0.

FIG. 17A: Although SBE-β-CD at 0.5% may not be fully sufficient to provide an elegant lyo cake on its own, it is compatible with more common bulking agents, such as glycine and mannitol. All of these lyo cakes reconstituted well and produced little to no aggregation or particulation in the presence of SBE-β-CD. FIG. 17B: The use of SBE-β-CD (blue chromatogram, indicated by arrow) but not α-cyclodextran (pink chromatogram, indicated by arrow) reduces % aggregate post-reconstitution. Control formulation without any cyclodextrin (in thick black line) also shows an elevated level of aggregates, albeit lower than α-cyclodextran. These results demonstrate the advantage of using SBE-β-CD. FIG. 17C: Analytical SEC of different formulations (pre and post represents pre-lyophilization and post-constitution). FIG. 17D: MFI analysis for different formulations following lyophilization.

DETAILED DESCRIPTION

Figure 1:
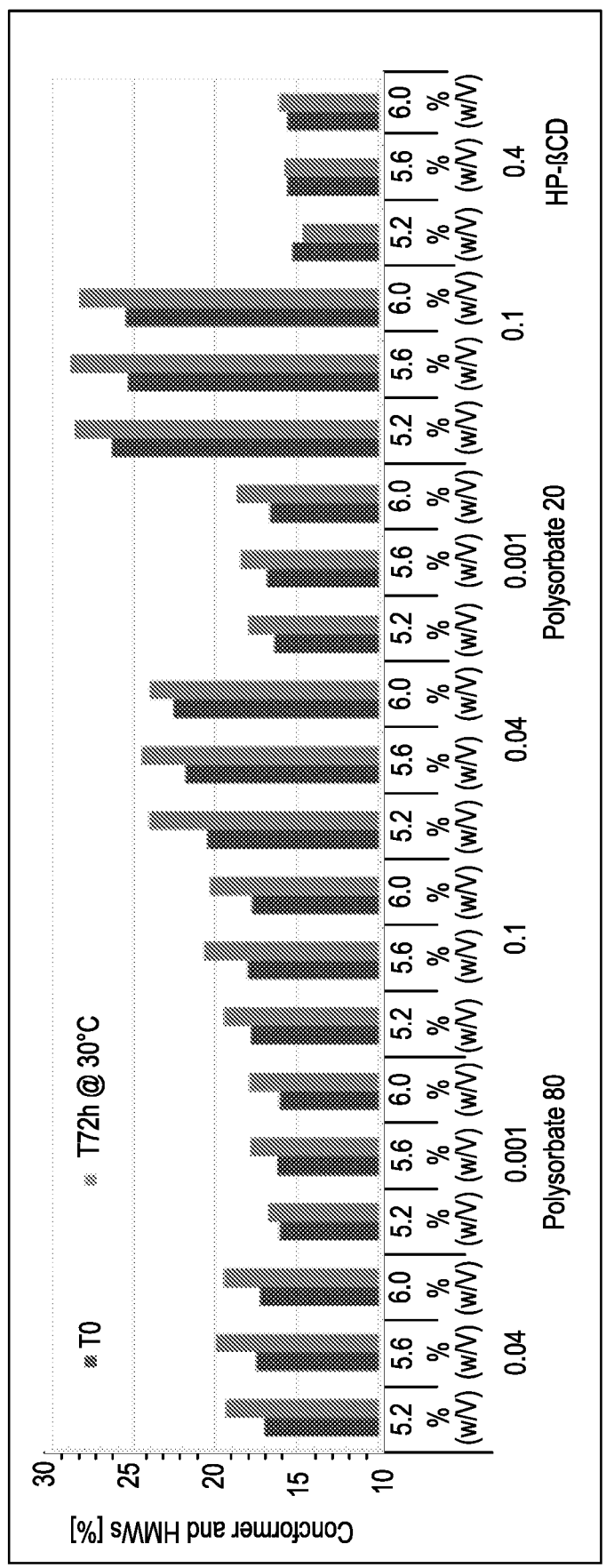
FIG. 1: Quantitation of high molecular weight species and conformer by size exclusion ultra high performance liquid chromatography (SE-UPLC) in AMG 330 (SEQ ID NO: 100) preparations containing polysorbate 20, 80 or HP-β-CD.

Despite the high quality of current therapeutic biotech products and the resemblance of recombinant human proteins and antibodies to endogenous human proteins, protein instability remains an important concern. In addition to the quality-related consequences of protein aggregation such as possible loss of protein activity and undesirable aesthetics of drug product, soluble protein aggregates have been reported to have significant cytotoxic effects, and, importantly, are a potential risk factor for the development of an the immune response to protein products.

Protein aggregation can occur during at various points throughout the lifetime of a protein, including fermentation, refolding, purification, filling, shipment, storage or administration and is strongly dependent on various environmental factors. There is a critical need in the art to increase stability and reduce aggregation of therapeutic proteins; and optimized pharmaceutical formulations can aid in doing so. The present inventors investigated the effects of different cyclodextrins to on the aggregation of bispecific antibody constructs (specifically, Bi-specific T-cell engagers, BiTE®) when exposed to various environmental stress factors. Surprisingly, the inventors found that antibody constructs could be significantly stabilized in the presence of cyclodextrins, and in particular β-cyclodextrins.

Thus, the present invention provides a stable pharmaceutical composition comprising a) a bispecific single chain antibody construct, binding to a target cell surface antigen via a first binding domain and to the T cell surface antigen CD3 via a second binding domain, b) a β-cyclodextrin and c) a buffer.

Stability

Within the present invention, the term "stability" or "stabilization" relates to the stability of the pharmaceutical composition in total and in particular to the stability of the active ingredient (i.e. the bispecific single chain antibody construct) itself, specifically during formulation, filling, shipment, storage and administration. The terms "stability" or "stable" in the context of the pharmaceutical composition of the invention and the bispecific single chain antibody construct particularly refers to the reduction or prevention of the formation of protein aggregates (HMWS). Specifically, the term "stability" also relates to the colloidal stability of the bispecific single chain antibody constructs comprised within the pharmaceutical composition described herein. "Colloidal stability" is the ability of colloidal particles (such as proteins) to remain dispersed in liquids for a prolonged period of time (days to years).

The term "(protein) aggregate" as used herein generally encompasses protein species of higher molecular weight such as "oligomers" or "multimers" instead of the desired defined species (e.g., a monomer). The term is used interchangeably herein with the terms "high molecular weight species" and "HMWS". Protein aggregates may generally differ in size (ranging from small (dimers) to large assemblies (subvisible or even visible particles) and from the nanometer to micrometer range in diameter), morphology (approximately spherical to fibrillar), protein structure (native vs. non-native/denatured), type of intermolecular bonding (covalent vs. non-covalent), reversibility and solubility. Soluble aggregates cover the size range of roughly 1 to 100 nm, and protein particulates cover subvisible (~0.1-100 .m) and visible (>100 .m) ranges. All of the aforementioned types protein aggregates are generally encompassed by the term. The term "(protein) aggregate" thus refers to all kinds physically-associated or chemically linked non-native species of two or more protein monomers.

The term "protein aggregation" or "non-native aggregation" thus denotes the process(es) by which protein molecules assemble into complexes composed of two or more proteins, with the individual proteins denoted as the monomer. There are multiple pathways leading to protein aggregation that can be induced by a wide variety of conditions, including temperature, mechanical stress such as shaking and stirring, pumping, freezing and/or thawing and formulation.

Temperature

An increase in temperature accelerates chemical reactions such as oxidation and deamidation of proteins, which can in turn promote aggregation. Higher temperature also directly influences conformation of proteins on the quaternary, tertiary, and secondary structure level, and can lead to temperature-induced unfolding that can promote aggregation.

Freezing and Thawing

Protein denaturation and aggregation can occur during freeze/thawing due to complex physical and chemical changes such as creation of new ice/solution interfaces, adsorption to container surfaces, cryoconcentration of the protein and solutes, and pH changes due to crystallization of buffer components.

Protein Concentration

An increase in protein concentration can also enhance the formation of protein aggregates. At high protein concentrations, macromolecular crowding occurs, a term used to describe the effect of high total volume occupancy by macromolecular solutes upon the behavior of each macromolecular species in that solution. According to this excluded volume theory, self-assembly and thus potentially aggregation may be favored.

Preservatives

Antimicrobial preservatives, such as benzyl alcohol and phenol, are often needed in protein liquid formulations to ensure sterility during its shelf life, and in addition required in multidose formulations and certain drug delivery systems, e.g., injection pens, minipumps and topical applications. Many preservatives have been reported to induce protein aggregation, although the underlying mechanism is not well understood. It has been proposed that preservatives bind to and populate unfolded protein states that are prone to aggregation.

Advantageously, the pharmaceutical compositions of the invention are envisaged to be stable, i.e. to remain free or substantially free from protein aggregates even when subjected to stress, in particular thermal stress, storage, surface-induced stress (such as freeze/thaw cycles, foaming), concentration (by ultra- and diafiltration) or being mixed with organic compounds such as antimicrobial preservatives. Preferably, the pharmaceutical compositions may have similar or even improved characteristics as compared to the compositions comprising SBE-β-CD or HP β-CD that have been evaluated in the appended Examples. Pharmaceutical compositions of the invention are preferably homogenous solutions of dispersed monomeric bispecific single chain antibody constructs.

The skilled person will appreciate that even though the pharmaceutical composition effectively provides for stabilization of the active ingredient (i.e. reduces or inhibits formation of protein aggregates of the bispecific single chain antibody construct), some aggregates or conformers may occasionally form, however without substantially compromising overall usability of the pharmaceutical composition. In this context "substantially free" of aggregates means that the amount of aggregates remains lower than 10%, 9%, 8%, 7%, 6%, 5%, 4%, 3%, 2% or 1% (w/v), particularly also when being subjected to environmental stress, e.g. as evaluated in the appended Examples.

Methods for determining the presence of soluble and insoluble protein aggregates have been, inter alia, reviewed by Mahler et al., *J Pharm Sci.* 2009 September; 98(9):2909-34. Formation of soluble protein aggregates can be evaluated by size exclusion ultra high performance liquid chromatography (SE-UPLC) as described in the appended Examples. SEC is one of the most used analytical methods for the detection and quantification of protein aggregates. SEC analysis allows both for sizing of aggregates, and their quantification. SEQ-UPLC allows for the selective and rapid separation of macromolecules based on their shape and size (hydrodynamic radius) in a molecular weight range of about 5-1000 kDa.

Protein solutions show an optical property, called opalescence or turbidity. The optical property of a solution is a function of the particles present to scatter and absorb light. Proteins are natural colloids and the turbidity of aqueous formulations depends on protein concentration, the presence of nondissolved particles, particle size and particle number per volume unit. Turbidity can be measured by UV-Vis spectroscopy as optical density in the 340-360 nm range and be used to detect both soluble and insoluble aggregates.

Moreover, the inspection of samples by visual means is still an important aspect of assessing protein aggregates. Visual evaluation for the absence or presence of visible aggregates is preferably performed according to Deutscher Arzneimittel Codex (DAC) Test 5.

As set out elsewhere herein, it is envisaged pharmaceutical composition of the invention—most likely by the action of β-cyclodextrins comprised therein—favor an increased colloidal stability of the bispecific single chain antibody constructs, and thus exhibit a reduced or even absent liquid-liquid phase separation (LLPS). LLPS is a thermodynamically driven event, in which a homogenous protein solution separates into a protein-poor phase (usually the top layer) and a protein-rich phase (usually the bottom layer) with decreasing temperatures. LLPS is typically fully reversible simply by mixing the two phases and raising the temperature of the solution. The occurrence of LLPS has been attributed to short-range attractive protein-protein interactions—making it a measure of strength of protein-protein attraction. Pharmaceutical compositions comprising β-cyclodextrins according to the invention have been found to comprise higher concentrations of the bispecific single chain antibody construct in the LLPS protein-poor phase, as compared to pharmaceutical compositions not comprising β-cyclodextrins. Accordingly, pharmaceutical compositions of the invention are envisaged to exhibit reduced LLPS or no LLPS at all when compared to controls, and thus promoting an increased colloidal stability of the bispecific single chain antibody constructs of the present invention. LLPS can be induced and the protein content of the different phases can be examined as described in the appended Examples.

Environmental stress can, in particular due to thermal and/or chemical denaturation, also lead to conformational changes, which may in turn favor aggregation. Surprisingly, the present inventors found that bispecific single chain antibody constructs are also stabilized with regard to conformational changes as evaluated by measuring intrinsic fluorescence emission intensity of aromatic amino acids. The pharmaceutical composition of the present invention therefore preferably also reduces or inhibits the formation of conformers (i.e. non-native, abnormally folded protein species).

Antibody Construct

As explained previously, the stable pharmaceutical composition of the present invention comprises a bispecific single chain antibody construct, binding to a target cell surface antigen via a first binding domain and to the T Cell surface antigen CD3 via a second binding domain.

The term "antibody construct" generally refers to a molecule in which the structure and/or function is/are based on the structure and/or function of an antibody, e.g. of a full-length or whole immunoglobulin molecule. An antibody construct is hence capable of binding to its specific target or antigen. Furthermore, an antibody construct according to the invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region). The antibodies on which the constructs described herein are based include for example monoclonal, recombinant, chimeric, deimmunized, humanized and human antibodies.

Within the definition of "antibody constructs" are full-length or whole antibodies including camelid antibodies and other immunoglobulin antibodies generated by biotechnological or protein engineering methods or processes. These full-length antibodies may be for example monoclonal, recombinant, chimeric, deimmunized, humanized and human antibodies. Also within the definition of "antibody constructs" are fragments of full-length antibodies, such as VH, VHH, VL, (s)dAb, Fv, Fd, Fab, Fab', F(ab')2 or "r IgG" ("half antibody"). Antibody constructs may also be modified fragments of antibodies, also called antibody variants, such as scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, "minibodies" exemplified by a structure which is as follows: (VH-VL-CH3)2, (scFv-CH3)2 or (scFv-CH3-scFv)2, multibodies such as triabodies or tetrabodies, and single domain antibodies such as nanobodies or single variable domain antibodies comprising merely one variable domain, which might be $V_HH$, $V_{NAR}$ VH or VL, that specifically bind an antigen or epitope independently of other V regions or domains. Also encompassed by the term "antibody construct" are single domain antibody constructs composed of (at least) two single domain monoclonal antibodies which are individually selected from the group comprising VH, VL, $V_HH$ and $V_{NAR}$, and a linker. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

Furthermore, the definition of the term "antibody constructs" generally includes monovalent, bivalent and polyvalent/multivalent constructs and, thus, monospecific constructs, specifically binding to only one antigenic structure, as well as bispecific and polyspecific/multispecific constructs, which specifically bind more than one antigenic structure, e.g. two, three or more, through distinct binding domains. Moreover, the definition of the term "antibody constructs" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). In the context of the present invention, bispecific single chain antibody constructs binding to a target cell surface antigen via a first binding domain and to the T cell surface antigen CD3 via a second binding domain are particularly envisaged.

Binding Domains

The term "binding domain" characterizes a domain which (specifically) binds to/interacts with/recognizes a given target epitope or a given target site on the target molecules (antigens). Binding domains are preferably in the form of polypeptides. Such polypeptides may include proteinaceous parts and non-proteinaceous parts (e.g. chemical linkers or chemical cross-linking agents such as glutaraldehyde). Proteins (including fragments thereof, preferably biologically active fragments, and peptides, usually having less than 30 amino acids) comprise two or more amino acids coupled to each other via a covalent peptide bond (resulting in a chain of amino acids). The term "polypeptide" as used herein describes a group of molecules, which usually consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a hetero multimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

The structure and function of the first binding domain, and preferably also the structure and/or function of the second binding domain is based on the structure and/or function of an antibody, e.g. of a full-length or whole immunoglobulin molecule. The first binding domain is characterized by the presence of three light chain CDRs (i.e. CDR1, CDR2 and CDR3 of the variable light (VL) region) and three heavy chain CDRs (i.e. CDR1, CDR2 and CDR3 of the variable heavy (VH) region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region).

As mentioned above, a binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of (modified) antigen-binding antibody fragments include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv).

Variable Regions

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding site. The CH domain most proximal to VH is designated as CH1. Each light (L) chain is linked to a heavy (H) chain by one covalent disulfide bond, while the two H chains are linked to each other by one or more disulfide bonds depending on the H chain isotype.

Variability is not evenly distributed throughout the variable domains of antibodies; it is concentrated in sub-domains of each of the heavy and light chain variable regions. These sub-domains are called "hypervariable regions" or "complementarity determining regions" (CDRs). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding site is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding site. H3, for example, can be as short as two amino acid residues or greater than 26 amino acids.

Framework and Constant Regions

The more conserved (i.e., non-hypervariable) portions of the variable domains are called the "framework" regions (FRM) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit.). The constant domains are not directly involved in antigen binding, but exhibit various effector functions, such as, for example, antibody-dependent, cell-mediated cytotoxicity and complement activation.

Binding Specificity

Bispecific Antibody Constructs

As explained previously, the antibody construct comprised within the pharmaceutical composition of the invention is particularly envisaged to be a bispecific single chain antibody construct. The term "bispecific" as used herein refers to an antibody construct which is "at least bispecific", i.e., it comprises at least a first binding domain and a second binding domain, wherein the first binding domain binds to one antigen or target, and the second binding domain binds to another antigen or target. Accordingly, antibody constructs encompassed by the term comprise specificities for at least two different antigens or targets. The term "bispecific antibody construct" thus also encompasses multispecific antibody constructs such as trispecific antibody constructs, the latter ones including three binding domains, or constructs having more than three (e.g. four, five . . . ) specificities. Given that the antibody constructs are (at least) bispecific, they do not occur naturally and they are markedly different from naturally occurring products. A "bispecific" antibody construct is hence an artificial hybrid antibody or immunoglobulin having at least two distinct binding sites with different specificities. Bispecific antibodies can be produced by a variety of methods known in the art, e.g. by chemical conjugation of two different, purified monoclonal antibodies (mAbs) or antibody fragments or by fusing two hybridomas resulting in a quadroma cell line producing, among others, bispecific IgG molecules (see Kontermann and Brinkmann, *Drug Discov Today.* 2015 July; 20(7):838-47 for review).

Targets

As set out previously, the pharmaceutical composition of the invention comprises a bispecific single chain antibody construct binding to a target cell surface antigen via a first binding domain and to the T Cell surface antigen CD3 via a second binding domain.

The terms "(specifically) binds to", (specifically) recognizes", "is (specifically) directed to", and "(specifically) reacts with" mean in accordance with this invention that a binding domain interacts or specifically interacts with one or more, preferably at least two, more preferably at least three and most preferably at least four amino acids of an epitope located on the target protein or antigen.

The term "epitope" refers to a site on an antigen to which a binding domain, such as an antibody or immunoglobulin or derivative or fragment of an antibody or of an immunoglobulin, specifically binds. An "epitope" is antigenic and thus the term epitope is sometimes also referred to herein as "antigenic structure" or "antigenic determinant". Thus, the binding domain is an "antigen interaction site". Said binding/interaction is also understood to define a "specific recognition". "Epitopes" can be formed both by contiguous amino acids (linear epitope) or non-contiguous amino acids juxtaposed by tertiary folding of a protein (conformational epitope. Linear epitopes typically includes at least 3 or at least 4, and more usually, at least 5 or at least 6 or at least 7, for example, about 8 to about 10 amino acids in a unique sequence. A conformational epitope typically comprises an increased number of amino acids relative to a linear epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

The interaction between the binding domain and the epitope or epitope cluster implies that a binding domain exhibits appreciable affinity for the epitope or epitope cluster on a particular protein or antigen and, generally, does not exhibit significant reactivity with non-target proteins or antigens. "Appreciable affinity" includes binding with an affinity of about $10^{-6}$ M (KD) or stronger. Preferably, binding is considered specific when the binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Preferably, a binding domain of the invention does not essentially or substantially bind to proteins or antigens other than its target proteins or antigens (i.e., the first binding and second binding domain are not capable of binding to proteins other than their respective target protein).

The term "does not essentially/substantially bind" or "is not capable of binding" means that a binding domain of the present invention does not bind a protein or antigen other than its target protein or antigen, i.e., does not show reactivity of more than 30%, preferably not more than 20%, more preferably not more than 10%, particularly preferably not more than 9%, 8%, 7%, 6% or 5% with proteins or antigens other than its target protein or antigen, whereby binding to its respective target protein or antigen is set to be 100%.

As explained herein, the bispecific single chain antibody construct is envisaged to comprise a first binding domain capable of binding to a target cell surface antigen and a second binding domain capable of binding to the T Cell surface antigen CD3. The antibody construct, the binding domains and in particular the second binding domain (which binds to human CD3 on the surface of a T cell) is in particular envisaged to have the following format: The pairs of VH regions and VL regions are in the format of a single chain antibody (scFv). The VH and VL regions are arranged in the order VH-VL or VL-VH. It is preferred that the VH-region is positioned N-terminally to a linker sequence, and the VL-region is positioned C-terminally of the linker sequence.

The second binding domain of the antibody construct comprised within the pharmaceutical composition of the invention is capable of binding to the T Cell surface antigen CD3. T cells or T lymphocytes are a type of lymphocyte (itself a type of white blood cell) that play a central role in cell-mediated immunity. There are several subsets of T cells, each with a distinct function. T cells can be distinguished from other lymphocytes, such as B cells and NK cells, by the presence of a T cell receptor (TCR) on the cell surface. The TCR is responsible for recognizing antigens bound to major histocompatibility complex (MHC) molecules and is composed of two different protein chains. In 95% of the T cells, the TCR consists of an alpha (α) and beta (β) chain. When the TCR engages with antigenic peptide and MHC (peptide/MHC complex), the T lymphocyte is activated through a series of biochemical events mediated by associated enzymes, co-receptors, specialized adaptor molecules, and activated or released transcription factors The CD3 receptor complex is a protein complex and is composed of four chains. In mammals, the complex contains a CD3γ (gamma) chain, a CD3δ (delta) chain, and two CD3ε (epsilon) chains. These chains associate with the T cell receptor (TCR) and the so-called ζ (zeta) chain to form the T cell receptor CD3 complex and to generate an activation signal in T lymphocytes. The CD3γ (gamma), CD3δ (delta), and CD3ε (epsilon) chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signaling capacity of the TCR. The CD3 epsilon molecule is a polypeptide which in humans is encoded by the CD3E gene which resides on chromosome 11.

The second binding domain of the bispecific single chain antibody construct comprised within the pharmaceutical composition of the invention is capable of binding to a target cell surface antigen. Said target cell surface antigen may in general be any antigen that can be recognized by and bind to the second binding domain. The bispecific single chain antibody construct is envisaged to form a link between T cells and target cells by binding to both CD3 and the target cell surface antigen. The bispecific single chain antibody construct is thus thought to recruit T cells to target cells, and preferably to cause T cells to exert cytotoxic activity on target cells by producing pro-apoptotic proteins like perforin and granzymes, thereby causing target cell. The target cell will therefore typically be a cell intended as a target for T cell mediated cytotoxicity and, hence, cytolysis. For instance, the target cell may be a tumor cell such as a malignant blast cell. The target cell surface antigen may thus be selected from CD33, CD19, FAPalpha, MSLN, FLT3 or BCMA. CD33 is particularly envisaged as a target for the first binding domain of the bispecific single chain antibody construct of the invention.

Preferred bispecific single chain antibody constructs of the present invention include AMG 103 (comprising a first binding domain recognizing CD19), AMG 330 (comprising a first binding domain recognizing CD33) a CD33 specific HLE BiTE, a FLT3 specific HLE BiTE and a BCMA specific HLE BiTE as evaluated in the appended Examples.

Specifically, the amino acid sequence of the first binding domain of the bispecific single chain construct may be selected form the group consisting of SEQ ID 99, 109, 119, 128, 137, 146, 155, 164, 173, 183, 185 and 187 and the amino acid sequence of the second binding domain of the bispecific single chain construct may be selected form the group consisting of SEQ ID NO: 9, 18, 27, 36, 45, 54, 63, 72, 81, 179 and 90.

Preferred bispecific single chain antibody constructs of the invention thus include constructs comprising or consisting of polypeptide having an amino acid sequence as depicted in a SEQ ID NO selected from the group consisting of SEQ ID NO:100, SEQ ID NO:110, SEQ ID NO:174, SEQ ID NO:175, SEQ ID NO:176, SEQ ID NO:177, SEQ ID NO:180, SEQ ID NO:182, SEQ ID NO:184, SEQ ID NO:186, SEQ ID NO:188.

Peptide Linkers

The at least two binding domains and the variable domains of the antibody construct of the present invention may or may not comprise peptide linkers (spacer peptides).

The term "peptide linker" defines in accordance with the present invention an amino acid sequence by which the amino acid sequences of one (variable and/or binding) domain and another (variable and/or binding) domain of the antibody construct of the invention are linked with each other. An essential technical feature of such peptide linker is that said peptide linker does not comprise any polymerization activity. Among the suitable peptide linkers are those described in U.S. Pat. Nos. 4,751,180 and 4,935,233 or WO 88/09344.

In the event that a linker is used, this linker is preferably of a length and sequence sufficient to ensure that each of the first and second domains can, independently from one another, retain their differential binding specificities. For peptide linkers which connect the at least two binding domains in the antibody construct (or two variable domains), those peptide linkers may comprise only a few number of amino acid residues, e.g. 12 amino acid residues or less, such as 11, 10, 9, 8, 7, 6 or 5 amino acid residues. An envisaged peptide linker with less than 5 amino acids comprises 4, 3, 2 or one amino acid(s) and may be Gly-rich, i.e. may consist of the single amino acid Gly. Other useful peptide linker are characterized by the amino acid sequence Gly-Gly-Gly-Gly-Ser (SEQ ID NO: 178), i.e. Gly$_4$Ser, or polymers thereof, i.e. (Gly$_4$Ser)x, where x is an integer of 1 or greater. Preferably, peptide linkers do not promote any secondary structures are preferred. Methods for preparing fused and operatively linked bispecific single chain constructs and expressing them in mammalian cells or bacteria are well-known in the art (e.g. Sambrook et al., Molecular Cloning: A Laboratory Manual, 4$^{th}$ ed., Cold Spring Harbor Laboratory Press, Cold Spring Harbor, N.Y., 2012).

Derivatives

The term "antibody construct" also encompasses derivatives. The term "derivative" generally refers to an antibody construct that has been covalently modified to introduce an additional functionality. Covalent modifications of the antibody constructs can be introduced post-translationally by reacting specific amino acid residues of the molecule with an organic derivatizing agent that is capable of reacting with selected side chains or the N- or C-terminal residues. Derivatization of antibody constructs can be used to attach therapeutic or diagnostic agents, labels, groups extending the serum half-life of the molecule, or insertion of non-natural amino acids. Commonly applied chemical modifications include the following:

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the antibody constructs of the present invention to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Glycosylation and De-Glycosylation

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody construct is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the amino acid sequence of an antibody construct is preferably altered through changes at the DNA level, particularly by mutating the DNA encoding the polypeptide at preselected bases such that codons are generated that will translate into the desired amino acids.

Another means of increasing the number of carbohydrate moieties on the antibody construct is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, 1981, CRC Crit. Rev. Biochem., pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Non-Proteinaceous Polymers

Other modifications of the antibody construct are contemplated herein. For example, another type of covalent modification of the antibody construct comprises linking the antibody construct to various non-proteinaceous polymers, including, but not limited to, various polyols such as various polyols such as polyethylene glycol (PEGylation), polypropylene glycol, polyoxyalkylenes, or copolymers of polyethylene glycol and polypropylene glycol, or of carbohydrates, such as hydroxyethyl starch (e.g., HESylation®) or polysialic acid (e.g., PolyXen® technology. In addition, as is known in the art, amino acid substitutions may be made in various positions within the antibody construct, e.g. in order to facilitate the addition of polymers such as PEG.

Labels

In some embodiments, the covalent modification of the antibody constructs of the invention comprises the addition of one or more labels. The labelling group may be coupled to the antibody construct via spacer arms of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to:

a) isotopic labels, which may be radioactive or heavy isotopes, such as radioisotopes or radionuclides e. $^3$H, $^{14}$C, $^{15}$N, $^{35}$S, $^{89}$Zr, $^{90}$Y, $^{111}$In, $^{125}$I, $^{131}$I)
b) magnetic labels (e.g., magnetic particles)
c) redox active moieties
d) optical dye (including, but not limited to, chromophores, phosphors and fluorophores) such as fluorescent groups (e.g., FITC, rhodamine, lanthanide phosphors), chemiluminescent groups, and fluorophores which can be either "small molecule" fluores or proteinaceous fluores
e) enzymatic groups (e.g. horseradish peroxidase, β-galactosidase, luciferase, alkaline phosphatase)
f) biotinylated groups
g) predetermined polypeptide epitopes recognized by a secondary reporter (e.g., leucine zipper pair sequences, binding sites for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc.*

Natl. Acad. Sci. U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558).

Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising CDH19 antibody fragment or derivative fused to a leucine zipper peptide are expressed in suitable host cells, and the soluble oligomeric CDH19 antibody fragments or derivatives that form are recovered from the culture supernatant.

The antibody construct may also comprise additional peptides or domains, which are e.g. helpful in the isolation of the molecule or relate to an adapted pharmacokinetic profile of the molecule. Domains helpful for the isolation of an antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. His-tag domains are generally known as a repeat of consecutive His residues in the amino acid sequence of a molecule, preferably of six His residues. Domains or peptides useful for extending the serum half-life (i.e. the time where 50% of an administered drug are eliminated through biological processes, e.g. metabolism, excretion, etc.) of the antibody constructs include those capable of binding to other proteins with a preferred pharmacokinetic profile in the human body such as serum albumin (e.g. the AB156 peptide) or the constant region of immunoglobulins (Fc domains or variants thereof).

The bispecific single chain antibody construct is envisaged to be present in the pharmaceutical composition of the invention in a concentration of up to about 5 mg/mL, i.e. about 4.0 mg/mL, 3.0 mg/mL, 2.0 mg/mL, 1.0 mg/mL, 0.5 mg/mL, 0.25 mg/mL or 0.1 mg/mL. Preferably, the bispecific single chain antibody construct is present in the pharmaceutical composition in a concentration between 0.1 to 5 mg/mL, preferably of 0.2-2.5 mg/mL, more preferably of 0.25-1.0 mg/mL.

Cyclodextrins

Besides the bispecific single chain antibody construct and the buffer, the pharmaceutical composition of the present invention further comprises a β-cyclodextrin. In general, the term "cyclodextrin" or "CD" refers to a cyclic oligosaccharides composed of at least 6 or more 1→4 linked α-D-glucopyranoside units. The unitary structure of the cyclodextrins is characterized by a hydrophobic cavity with ether groups inside and a polar exterior which is characterized by primary hydroxyl groups. Many cyclodextrins are known in the art, including 6-membered (α-cyclodextrins), 7-membered (β-cyclodextrins) and 8-membered (γ-cylodextrins) cyclodextrins. β-cyclodextrins comprising 7 α-D-glucopyranoside units are particularly preferred components of the pharmaceutical composition of the invention, as they have been shown to be capable of effectively stabilizing the bispecific single chain antibody constructs under various stress conditions.

The term "cyclodextrin" (and in particular "β-cyclodextrin") also encompasses chemically modified (β-)cyclodextrin derivatives. In general, any chemical modification is conceivable as long as it does not reduce or abolish the advantageous properties of the pharmaceutical composition as demonstrated in the appended examples, and in particular as long as the pharmaceutical compositions retains its stability. Chemically modified cyclodextrin derivatins typically result from etherification or the introduction of other functional groups at the 2-, 3- and 6-hydroxyl groups of the glucose residues. Thus, the term includes cyclodextrins comprising one or more substitutions of the hydroxyl groups, e.g. alkylated and hydroxyalkylated cyclodextrins.

For the purpose of the invention, the term "cyclodextrin" also includes pharmaceutically acceptable salt(s) thereof. The phrase "pharmaceutically acceptable salt(s)", as used herein, means those salts of cyclodextrins that are safe and effective for the administration. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Of course, any counterions used in pharmaceuticals must be considered safe, and several lists of pharmaceutically approved counterions exist, which vary depending on the source. Approved salt formers can e.g. be found in the Handbook of Pharmaceutical Salts (Stahl P H, Wermuth C G, editors. 2002. Handbook of pharmaceutical salts: Properties, selection and use. Weinheim/Zurich: Wiley-VCH/VHCA).

Thus, the pharmaceutical composition of the invention is envisaged to comprise a β-cyclodextrin, particularly one selected from the group consisting of β-cyclodextrin, methyl-β-cyclodextrin, hydroxyethyl-β-cyclodextrin, hydroxypropyl-β-cyclodextrin, ethyl-β-cyclodextrin, butyl-β-cyclodextrin Succinyl-(2-hydroxypropyl)-β-cyclodextrin, heptakis(2,3,6-tri-O-methyl)-β-cyclodextrin, heptakis(2,3,6-tri-O-benzoyl)-β-cyclodextrin, β-cyclodextrin phosphate sodium salt, β-cyclodextrin sulphate sodium salt, triacetyl-β-cyclodextrin, heptakis(6-O-sulfo)-β-cyclodextrin heptasodium salt, carboxymethyl-β-cyclodextrin sodium salt, sulfobutylether-β-cyclodextrin sodium salt, and 6-O-p-toluenesulfonyl-β-cyclodextrin. In particular, the β-cyclodextrin may be sulfobutylether-β-cyclodextrin ("SBE-β-CD") sodium salt, hydroxypropyl-β-cyclodextrin ("HP-β-CD").

The β-cyclodextrin may be present in the pharmaceutical composition in a concentration in the range of 0.1% to 20% (w/v), preferably of 0.5% to 2% (w/v) and more preferably of 0.8% to 1.5% (w/v). It is in particular envisaged that the concentration of chemically unmodified β-cyclodextrin is about 1.8% (w/v) or less, such as about 1.6% (w/v), about 1.5% (w/v), about 1.4% (w/v), about 1.3% (w/v), about 1.2% (w/v), about 1.1% (w/v), about 1.0% (w/v), about 0.9% (w/v), about 0.8% (w/v), or less, down to a concentration of about 0.1% (w/v).

Buffer

The pharmaceutical composition of the invention further comprises a buffer, which may be selected from the group consisting of potassium phosphate, acetic acid/sodium acetate, citric acid/sodium citrate, succinic acid/sodium succinate, tartaric acid/sodium tartrate, histidine/histidine HCl, glycine, Tris, glutamate, acetate and mixtures thereof, and in particular from potassium phosphate, citric acid/sodium citrate, succinic acid, histidine, glutamate, acetate and combinations thereof.

Suitable buffer concentrations encompass concentrations of about 200 mM or less, such as about 190, 180, 170, 160, 150, 140, 130, 120, 110, 100, 80, 70, 60, 50, 40, 30, 20, 10 or 5 mM. The skilled person will be readily able to adjust the buffer concentrations in order to provide for stability of the pharmaceutical composition as described herein. Envisaged buffer concentrations in the pharmaceutical composition of the invention specifically range from about 5 to about 200 mM, preferably from about 5 to about 100 mM, and more preferably from about 10 to about 50 mM.

pH

The pharmaceutical composition according to the invention may have a pH in the range from about 4 to about 7.5, i.e. a pH of 4, 4.5, 5, 5.5, 6, 6.5, 7 or 7.5. Preferably, the pH is in the range from about 5 to about 7.5, more preferably from about 5.5 to about 7.5.

Pharmaceutical Composition

As used herein, the term "pharmaceutical composition" relates to a composition which is suitable for administration to a subject in need thereof. The terms "subject" or "individual" or "animal" or "patient" are used interchangeably herein to refer to any subject, particularly a mammalian subject, for whom administration of the pharmaceutical composition of the invention is desired. Mammalian subjects include humans, non-human primates, dogs, cats, guinea pigs, rabbits, rats, mice, horses, cattle, cows, and the like, with humans being preferred. The pharmaceutical composition of the present invention is stable and pharmaceutically acceptable, i.e. capable of eliciting the desired therapeutic effect without causing any undesirable local or systemic effects in the subject to which the pharmaceutical composition is administered. Pharmaceutically acceptable compositions of the invention may in particular be sterile and/or pharmaceutically inert. Specifically, the term "pharmaceutically acceptable" can mean approved by a regulatory agency or other generally recognized pharmacopoeia for use in animals, and more particularly in humans.

The pharmaceutical composition of the invention comprises one or a plurality of the bispecific single chain antibody construct(s) described herein, preferably in a therapeutically effective amount, a β-cyclodextrin and a buffer. By "therapeutically effective amount" is meant an amount of said construct that elicits the desired therapeutic effect. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are generally preferred.

Excipients

Besides the β-cyclodextrin and the buffer described previously, the pharmaceutical composition may optionally comprise one or more further excipients as long as they do not reduce or abolish its advantageous properties as described herein, and in particular its stability.

Excipients can be used in the invention for a wide variety of purposes, such as adjusting physical, chemical, or biological properties of formulations, such as adjustment of viscosity, and or processes of the invention to further improve effectiveness and or to further stabilize such formulations and processes against degradation and spoilage due to, for instance, stresses that occur during manufacturing, shipping, storage, pre-use preparation, administration, and thereafter. The term "excipient" generally includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers.

Acceptable excipients are preferably pharmaceutically acceptable, i.e. nontoxic to recipients at the dosages and concentrations employed.

Exemplary excipients include, without limitation:
amino acids such as glycine, alanine, glutamine, asparagine, threonine, proline, 2-phenylalanine, including charged amino acids, preferably lysine, lysine acetate, arginine, glutamate and/or histidine
preservatives, including antimicrobials such as antibacterial and antifungal agents
antioxidants such as ascorbic acid, methionine, sodium sulfite or sodium hydrogen-sulfite;
buffers, buffer systems and buffering agents which are used to maintain the composition at physiological pH or at a slightly lower pH, typically within a pH range of from about 5 to about 8 or 9; examples of buffers are borate, bicarbonate, Tris-HCl, citrates, phosphates or other organic acids, succinate, phosphate, histidine and acetate; for example Tris buffer of about pH 7.0-8.5, or acetate buffer of about pH 4.0-5.5;
non-aqueous solvents such as propylene glycol, polyethylene glycol, vegetable oils such as olive oil, and injectable organic esters such as ethyl oleate;
aqueous carriers including water, alcoholic/aqueous solutions, emulsions or suspensions, including saline and buffered media;
biodegradable polymers such as polyesters;
bulking agents such as mannitol or glycine;
chelating agents such as ethylenediamine tetraacetic acid (EDTA);
isotonic and absorption delaying agents;
complexing agents such as caffeine, polyvinylpyrrolidone, beta-cyclodextrin or hydroxypropyl-beta-cyclodextrin)
fillers;
monosaccharides; disaccharides; and other carbohydrates (such as glucose, mannose or dextrins); carbohydrates may be non-reducing sugars, preferably trehalose, sucrose, octasulfate, sorbitol or xylitol;
(low molecular weight) proteins, polypeptides or proteinaceous carriers such as human or bovine serum albumin, gelatin or immunoglobulins, preferably of human origin;
coloring and flavouring agents;
sulfur containing reducing agents, such as glutathione, thioctic acid, sodium thioglycolate, thioglycerol, [alpha]-monothioglycerol, and sodium thio sulfate
diluting agents;
emulsifying agents;
hydrophilic polymers such as polyvinylpyrrolidone)
salt-forming counter-ions such as sodium;
preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);

metal complexes such as Zn-protein complexes;

solvents and co-solvents (such as glycerin, propylene glycol or polyethylene glycol);

sugars and sugar alcohols, including polyols, trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;

suspending agents;

surfactants or wetting agents such as pluronics, PEG, sorbitan esters, polysorbates such as polysorbate 20, polysorbate, triton, tromethamine, lecithin, cholesterol, tyloxapal; surfactants may be detergents, preferably with a molecular weight of >1.2 KD and/or a polyether, preferably with a molecular weight of >3 KD; non-limiting examples for preferred detergents are Tween 20, Tween 40, Tween 60, Tween 80 and Tween 85; non-limiting examples for preferred polyethers are PEG 3000, PEG 3350, PEG 4000 and PEG 5000;

stability enhancing agents such as sucrose or sorbitol;

tonicity enhancing agents such as alkali metal halides, preferably sodium or potassium chloride, mannitol sorbitol;

parenteral delivery vehicles including sodium chloride solution, Ringer's dextrose, dextrose and sodium chloride, lactated Ringer's, or fixed oils;

intravenous delivery vehicles including fluid and nutrient replenishers, electrolyte replenishers (such as those based on Ringer's dextrose).

It is evident to those skilled in the art that the different excipients of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

Polyols are useful stabilizing agents in both liquid and lyophilized formulations to protect proteins from physical and chemical degradation processes, and are also useful for adjusting the tonicity of formulations. Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Mannitol is commonly used to ensure structural stability of the cake in lyophilized formulations. It ensures structural stability to the cake. It is generally used with a lyoprotectant, e.g., sucrose. Sorbitol and sucrose are commonly used agents for adjusting tonicity and as stabilizers to protect against freeze-thaw stresses during transport or the preparation of bulks during the manufacturing process. PEG is useful to stabilize proteins and as a cryoprotectant.

Surfactants routinely are used to prevent, minimize, or reduce surface adsorption. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Commonly used surfactants include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration.

Antioxidants can—to some extent—prevent deleterious oxidation of proteins in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations are preferably water-soluble and maintain their activity throughout the shelf life of a product. EDTA is a useful example.

Metal ions can act as protein co-factors and enable the formation of protein coordination complexes. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Preservatives have the primary function to inhibit microbial growth and ensure product sterility throughout the shelf-life or term of use of the drug product, and are in particular needed for multi-dose formulations. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

Salts may be used in accordance with the invention to, for example, adjust the ionic strength and/or the isotonicity of the pharmaceutical formulation and/or to further improve the solubility and/or physical stability of the antibody construct or other ingredient. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility. Ionic species differ in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the pharmaceutical composition as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Particularly useful excipients for formulating the pharmaceutical composition include sucrose, trehalose, mannitol, sorbitol, arginine, lysine, polysorbate 20, polysorbate 80, poloxamer 188, pluronic and combinations thereof. Said excipients may be present in the pharmaceutical composition in different concentrations, as long as the composition exhibits the desirable properties as exemplified herein, and in particular promotes stabilization of the contained bispecific single chain antibody constructs. For instance, sucrose may be present in the pharmaceutical composition in a concentration between 2% (w/v) and 12% (w/v), i.e. in a concentration of 12% (w/v), 11% (w/v), 10% (w/v), 9% (w/v), 8% (w/v), 7% (w/v), 6% (w/v), 5% (w/v), 4% (w/v), 3% (w/v) or 2% (w/v). Preferred sucrose concentrations range between 4% (w/v) and 10% (w/v) and more preferably between 6% (w/v) and 10% (w/v). Polysorbate 80 may be present in the pharmaceutical composition in a concentration between 0.001% (w/v) and 0.5% (w/v), i.e. in a concentration of 0.5% (w/v), 0.2% (w/v), 0.1% (w/v), 0.08% (w/v), 0.05% (w/v), 0.02% (w/v), 0.01% (w/v), 0.008% (w/v), 0.005% (w/v), 0.002% (w/v) or 0.001% (w/v). Preferred Polysorbate 80 concentrations range between 0.002% (w/v) and 0.5% (w/v), and preferably between 0.005% (w/v) and 0.02% (w/v).

The pharmaceutical composition provided herein may in particular comprise one or more preservatives.

Useful preservatives for formulating pharmaceutical compositions generally include antimicrobials (e.g. anti-bacterial or anti-fungal agents), anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide). Antimicrobial preservatives are substances which are used to extend the shelf-life of medicines by reducing microbial proliferation. Preservatives that particularly useful for formulating the pharmaceutical composition of the invention include benzyl alcohol, chlorobutanol, phenol, meta-cresol, methylparaben, phenoxyethanol, propylparaben thiomerosal. The structure and typical concentration for the use of these preservatives are described in Table 1 of Meyer et al. J Pharm Sci. 96(12), 3155.

The aforementioned preservatives may be present in the pharmaceutical composition in different concentrations. For instance, benzyl alcohol may be present in a concentration ranging between 0.2 and 1.1% (v/v), chlorobutanol in a concentration ranging between 0.3-0.5% (v/v), phenol in a concentration ranging between 0.07 and 0.5% (v/v), meta-cresol in a concentration ranging between 0.17 and 0-32% (v/v) or thiomerosal in a concentration ranging between 0.003 to 0.01% (v/v). Preferred concentrations for methylparaben are in the range of 0.05 and 0.5% (v/v), for phenoxyethanol in the range of 0.1 and 3% (v/v) and for propylparaben in the range of 0.05 and 0.5% (v/v).

However, it is also conceivable that the pharmaceutical composition does not comprise any preservatives. In particular, the present invention inter alia provides a pharmaceutical composition being free of preservatives, comprising a bispecific single chain antibody construct having an amino acid sequence as depicted in SEQ ID Nos. 100 and 110 in a concentration of about 0.5 mg/ml, sulfobutylether-β-cyclodextrin sodium salt in a concentration of about 1% (w/v), and potassium phosphate in concentration of about 10 mM, and further sucrose in concentration of about 8% (w/v) of and polysorbate 80 in concentration of about 0.01% (w/v) at a pH of about 6.0.

Form

The pharmaceutical compositions of the invention can be formulated in various forms, e.g. in solid, liquid, frozen, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts.

Generally, various storage and/or dosage forms are conceivable for the pharmaceutical composition of the invention, depending, La., on the intended route of administration, delivery format and desired dosage (see, for example, Remington's Pharmaceutical Sciences, 22nd edition, Oslo, A., Ed., (2012)). The skilled person will be aware that such choice of a particular dosage form may for example influence the physical state, stability, rate of in vivo release and rate of in vivo clearance of the antibody construct of the invention.

For instance, the primary vehicle or carrier in a pharmaceutical composition may be either aqueous or non-aqueous in nature. A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles.

When parenteral administration is contemplated, the therapeutic compositions of the invention may be provided in the form of a pyrogen-free, parenterally acceptable aqueous solution comprising the desired antibody construct in a pharmaceutically acceptable vehicle. A particularly suitable vehicle for parenteral injection is sterile distilled water in which the antibody construct is formulated as a sterile, isotonic solution, properly preserved. The preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. Hyaluronic acid may also be used, having the effect of promoting sustained duration in the circulation. Implantable drug delivery devices may be used to introduce the desired antibody construct.

Sustained- or controlled-delivery/release formulations are also envisaged herein. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949. The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 22nd edition, Oslo, A., Ed., (2012).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544, 545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Further Active Agents

It is envisaged that the composition of the invention might comprise, in addition to the bispecific single chained antibody construct defined herein, further biologically active agents, depending on the intended use of the composition. Such agents might be in particular drugs acting on tumors and/or malignant cells, but other active agents are also conceivable depending on the intended use of the pharmaceutical composition, including agents acting on on the gastro-intestinal system, drugs inhibiting immunoreactions (e.g. corticosteroids), drugs modulating the inflammatory response, drugs acting on the circulatory system and/or agents such as cytokines known in the art. It is also envisaged that the pharmaceutical composition of the present invention is applied in a co-therapy, i.e., in combination with another anti-cancer medicament.

Storage

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. E.g., lyophilized compositions may be reconstituted in, e.g., bacteriostatic water for injection (BWFI), physiological saline, phosphate buffered saline (PBS), or the same formulation the protein had been in prior to lyophilization.

Route of Administration

The pharmaceutical composition of the invention may in general be formulated for delivery by any suitable route of administration. In the context of the present invention, the routes of administration include, but are not limited totopical routes (such as epicutaneous, inhalational, nasal, opthalmic, auricular/aural, vaginal, mucosal); enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions described herein are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447,233; 4,486,194; 4,487,603; 4,596,556; 4,790,824; 4,941,880; 5,064,413; 5,312,335; 5,312,335; 5,383,851; and 5,399,163.

The pharmaceutical composition of the invention can also be administered uninterruptedly. As a non-limiting example, uninterrupted or substantially uninterrupted, i.e. continuous administration may be realized by a small pump system worn by the patient for metering the influx of the antibody construct into the body of the patient. The pharmaceutical composition can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the pharmaceutical composition of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

Continuous administration may also be achieved transdermally by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

The skilled person will readily understand that the pharmaceutical composition of the invention may in general comprise any of the aforementioned excipients, or additional active agents, or may be provided in any suitable form as long as it is stable and preferably exhibits the same advantageous properties as the pharmaceutical compositions comprising β-cyclodextrins that have been evaluated in the appended Examples. The skilled person will readily be able to adjust the various components so as to provide a pharmaceutical composition that is stable, i.e. is preferably substantially free from aggregates and/or conformers of the bispecific single chain antibody fragments comprised within.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following examples, offered for illustrative purposes only. The examples are not intended to limit the scope of the present invention in any way.

EXAMPLES

Example 1

Effect of Temperature-Induced Stress on Formulations Comprising AMG330 and HP-β-CD AMG 330 protein pool (SEQ ID NO: 100) derived from hydroxyapatite chromatography was dialyzed into a formulation base buffer composed of 100 mM tris base, 50 mM disodiumhydrogen phosphate, 4% (w/v) trehalose dihydrate at pH 5.2. The endpoint of dialysis was verified by osmolality measurements. The dialyzed bulk was concentrated by ultrafiltration and centrifugation to a concentration of 0.96 mg/mL and sterile filtered by means of a 0.2 µm PVDF filter. The preformulated bulk was divided into three equally sized volume fractions. These were adjusted to pH 5.2, 5.6 and 6.0 respectively using 5M sodium hydroxide and again filtered with a 0.2 µm PVDF filter. After pH adjustment preformulated bulks were spiked with the required volumes of stock solutions containing either 1% (w/V) polysorbate 20, 1% (w/V) polysorbate 80 or 4% (w/V) HP-β-CD. The concentrations of polysorbate 20, polysorbate 80 and HP-β-CD in the final formulations are shown in FIG. 1. The concentration of each formulation was adjusted to 0.4 mg/mL using base buffer composed as described above. All excipients were applied in compendial grade. The final formulations were filled to 150 µL in polypropylene reaction tubes and incubated in a controlled cabinet at 30° C. for 72 hours. The content of conformer and high molecular weight species (HMWS) was determined with size exclusion ultra high performance liquid chromatography (SE-UPLC). SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C. within the autosampler until analysis. The injection volume was 7.5 µL. In order to avoid carry over an intermediate injection with 40% ACN was performed after each sample. Detection was based on fluorescence (Ex 280 nm, Em 325 nm). Peak integration was performed using Empower® software. Relative AUC of monomer and size variants was reported. It could be shown that the formation of non-monomeric protein species (including conformers and high molecular weight species) during thermal stress (30° C.) can be inhibited in presence of HP-β-CD (FIG. 1). In contrast formulations containing polysorbate 20 or 80 exhibited formation of non-monomeric species over time.

Example 2

Effect of Surface-Induced Stress on Formulations Comprising AMG330 and HP-β-CD

Figure 2A:
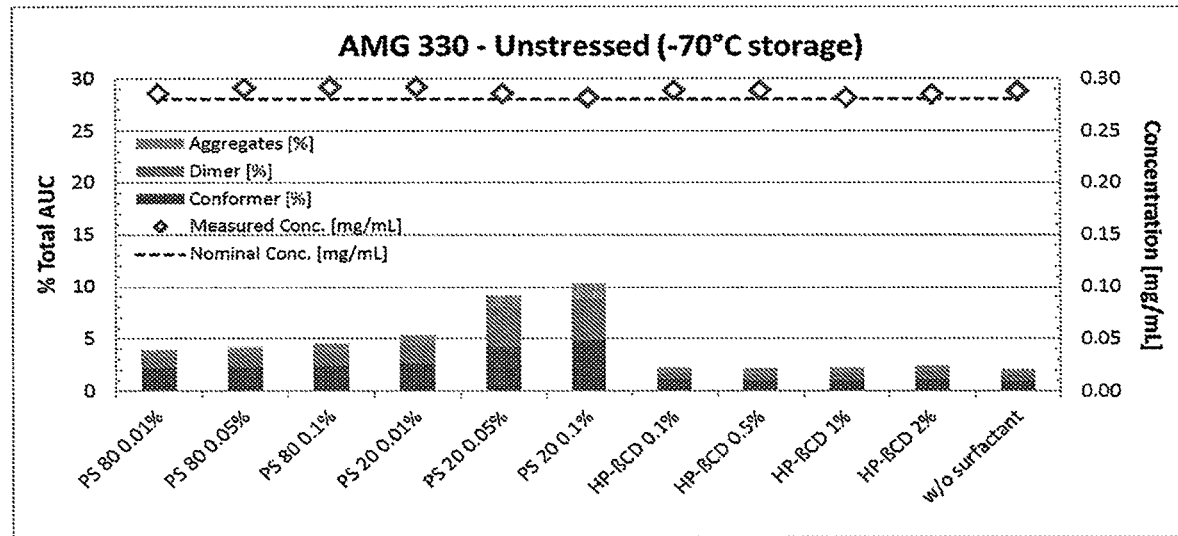
FIGS. 2A-2C: Effect of polysorbate (PS) 20, 80 and HP-β-CD on the amount of non-monomeric species (including conformers, dimers, aggregates) in AMG 330 preparations in function of stress factors: unstressed (FIG. 2A), foaming (FIG. 2B) and 10 freeze/thaw cycles (FIG. 2C). Quantitation of species was achieved by size exclusion ultra high performance chromatography (SE-UPLC). Protein concentration was addressed by the same assay (A280 detection).
Figure 2B:
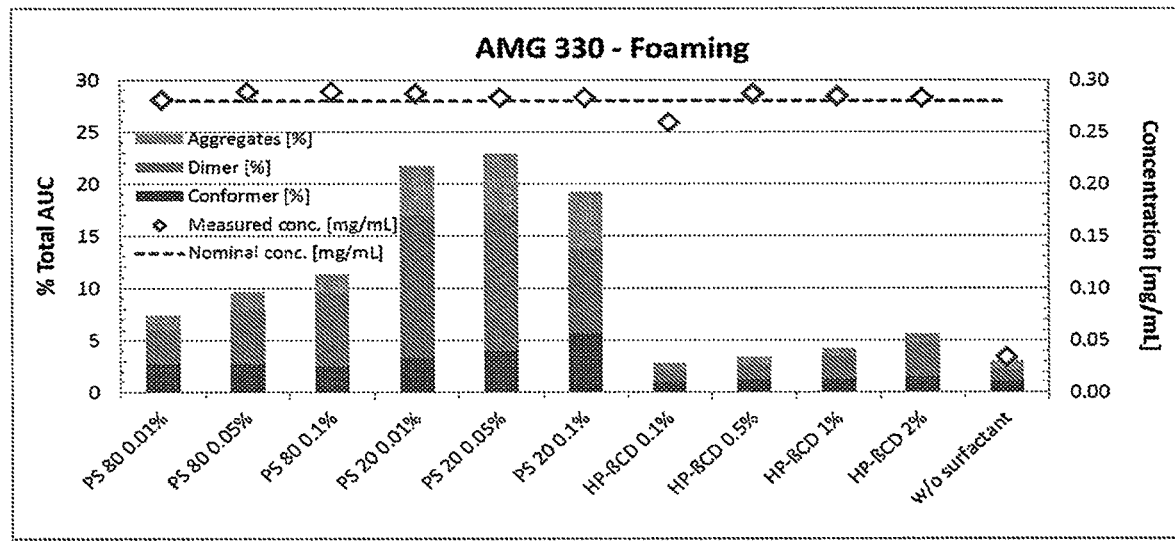
Figure 2C:
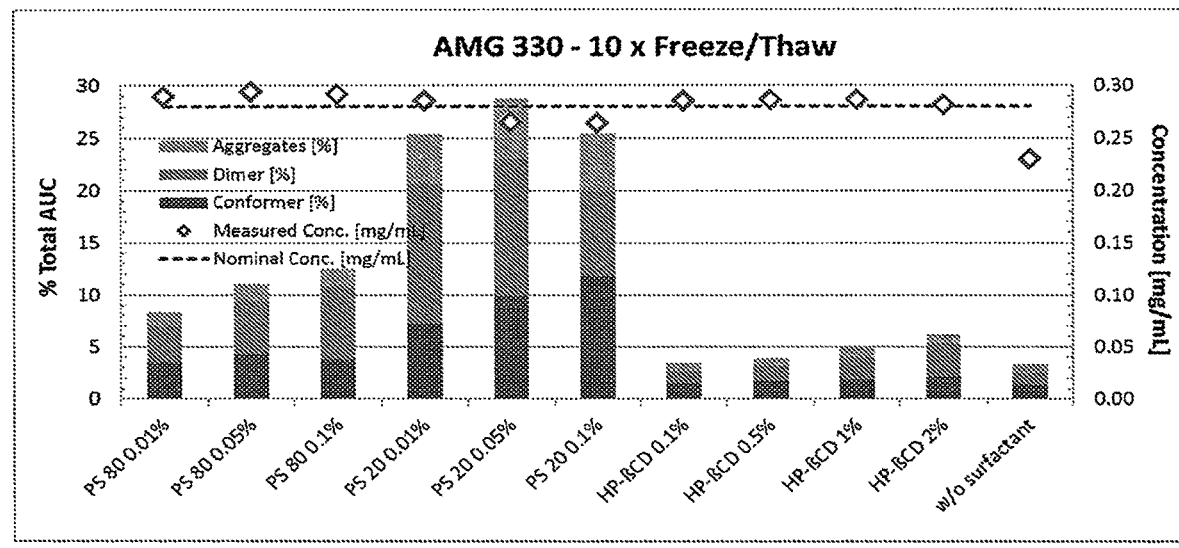

A further experiment was performed in order to assess whether HP-β-CD stabilizes AMG 330 against surface induced stress conditions. AMG 330 drug substance formulated in 35 mM tris hydrochloride, 17.5 mM sodium phosphate hydrogen phosphate, 100 mM L-arginine hydrochloride and 1.4% (w/V) trehalose dihydrate, pH 6.0 was supplemented with either polysorbate 20, 80 or HP-β-CD at different concentrations depicted in FIGS. 2A-2C (x-axis). All excipients were applied in compendial grade. Formulations were filled to 1.0 mL in prewashed and presterilized type I glass vials. Vials were stoppered with sterilized butyl rubber stoppers and were sealed with aluminum caps. Formulations were stressed by (1) ten consecutive freeze/thaw cycles and (2) foaming. Freezing and thawing was performed in an Epsilon 2-6D pilot scale lyophilizer (Christ, Germany). Target temperatures for freezing and thawing were set to −50° C. and 20° C. respectively. Freezing and thawing rates of 0.3 K/min. were used. Each temperature was followed by a 1 hour isothermal plateau. Foaming was achieved by injecting nitrogen into the respective solution over 1 hour at 80 mL per minute using a 21G injection needle. The vial was vented using a second injection needle equipped with sterile filter. Samples stored at −70° C. were used as non-stressed controls. Samples were analyzed by SE-UPLC and visible inspection according Deutscher Arzneimittel Codex (DAC) test 5. SE-UPLC was performed as described under Example 1. For the assessment of protein concentration detection was additionally performed via absorption at 280 nm. In the unstressed control samples it became evident that non-monomeric species including conformer, dimers and aggregates are more abundant in formulations containing polysorbate 20 or 80 if compared to formulations with HP-β-CD. When stressed by foaming and freeze/thaw, non-monomeric species increased in formulations containing polysorbates (FIGS. 2A-2C). The use of HP-β-CD reduced the formation of non-monomeric species. In absence of any surfactant, protein losses greater than 80% were observed whereas the use of polysorbate and HP-β-CD resulted in quantitative protein recovery. In contrast to surfactant free formulations, HP-β-CD containing formulations were practically free of protein aggregates in the visible size range (Table 1).

TABLE 1

Assessment of visible particles according to PhEur 2.9.20. Inspection result ratings assigned according to Deutscher Arzneimittel Codex (DAC) test 5.

| Treatment | % HP-β-CD | Inspection Result | Fulfillment of compendial requirement (DAC test 5)[1] |
|---|---|---|---|
| unstressed | 0.1 | 4 | yes |
| unstressed | 0.5 | 0 | yes |
| unstressed | 1 | 1 | yes |
| unstressed | 2 | 3 | yes |
| unstressed | without | 22 | no |
| 10 × F/T | 0.1 | 4 | yes |
| 10 × F/T | 0.5 | 2 | yes |
| 10 × F/T | 1 | 2 | yes |
| 10 × F/T | 2 | 4 | yes |
| 10 × F/T | without | 30 | no |
| Foaming | 0.1 | 6 | no |
| Foaming | 0.5 | 2 | yes |
| Foaming | 1 | 4 | yes |
| Foaming | 2 | 3 | yes |
| Foaming | without | 30 | no |

[1]Compendial requirement according to Deutscher Arzneimittel Codex (DAC) test 5: inspection result <4.5

Example 3

Effect of Benzyl Alcohol on Formulations Comprising AMG103 and HP-β-CD or SBE-β-CD The impact of HP-β-CD and SBE-β-CD on the stability of BITE® antibody constructs in presence of benzyl alcohol was investigated in formulations containing 0.6 mg/mL AMG 103 (blinatumomab). Therefore AMG 103 was formulated in 20 mM histidine, 2% (w/v) trehalose dihydrate, 0.9% (w/v) sodium chloride at pH 7.0. This formulation was supplemented with different concentrations of either HP-β-CD (0.5 and 1.0% w/V) or SBE-β-CD (0.5, 1.0 and 2.0% w/V). A cyclodextrin free formulation served as control. The AMG 103 concentration in all formulations was adjusted to 0.6 mg/mL. All excipients were applied in compendial grade. All formulations were spiked with 0.9% (V/V) benzyl alcohol and filled to 0.5 mL in polypropylene reaction tubes.

Incubation was performed at 37° C. for 24 hours. Samples were analyzed by UV absorption to determine the optical density at 350 nm as a measure for protein aggregation and by intrinsic fluorescence emission intensity measurement in order to detect potential conformational changes. UV absorption was performed on an Infinite M1000 plate reader (Tecan) using transparent half area 96 well plates (Corning). Each well was filled with 100 µL of sample solution. Sample measurements were performed in triplicates. UV absorption was recorded at 350 nm. Intrinsic fluorescence emission intensities were analyzed in the same plate from the bottom. Excitation was realized at 278 nm. Emission intensity was recorded from 300 to 500 nm using 1 nm increments. Excitation and emission slits were set to 10 and 5 nm respectively. During both UV and fluorescence measurements the plate was temperature controlled (25° C.).

Figure 3:
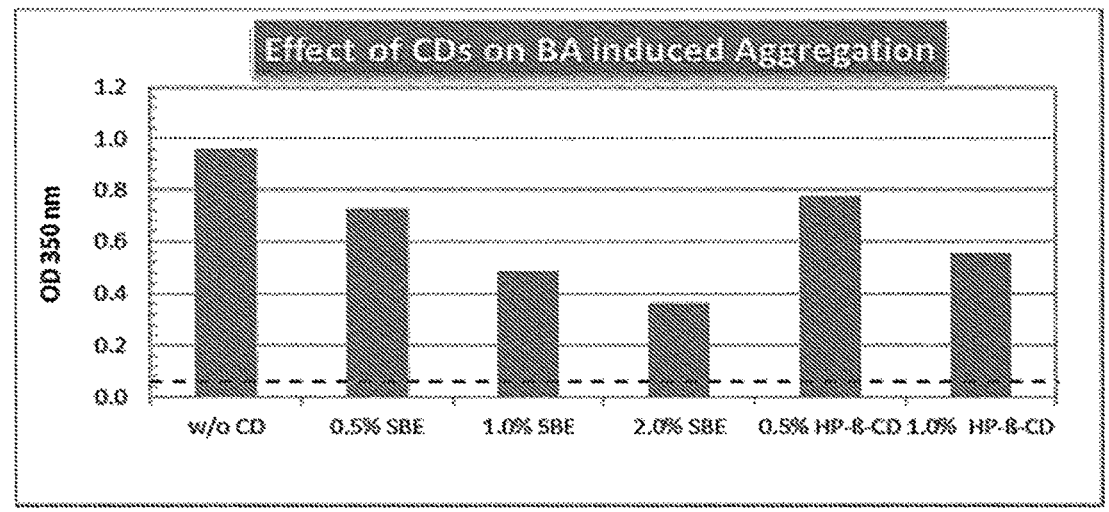
FIG. 3: Concentration dependent effect of HP-β-CD and SBE-β-CD on the aggregation propensity (measured by optical density at 350 nm; optical densities refer to a pathlength of 10 mm) of AMG 103 in presence of 0.9% (V/V) of benzyl alcohol.
Figure 4A:
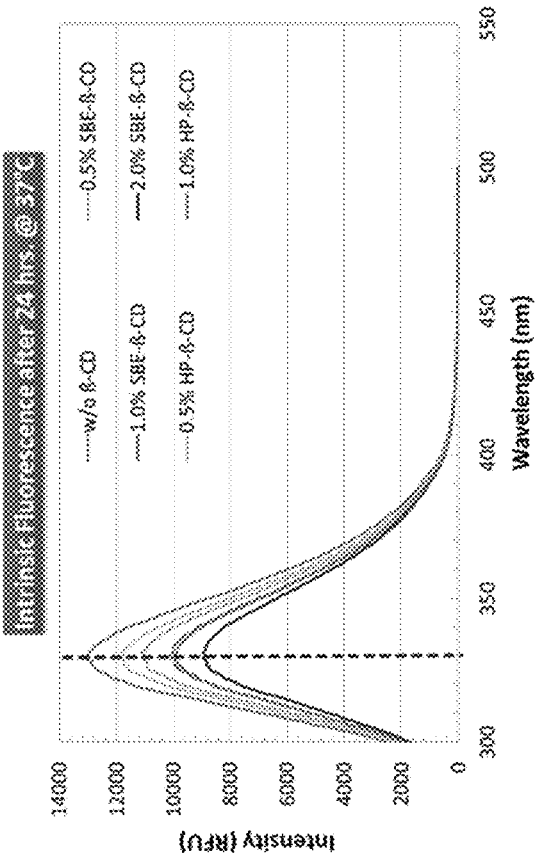
FIGS. 4A-4B: Intrinsic fluorescence emission intensity measurements of AMG 103 before (FIG. 4A) and after (FIG. 4B) incubation at 37° C. for 24 hours in presence of 0.9% (V/V) benzyl alcohol.
Figure 4B:
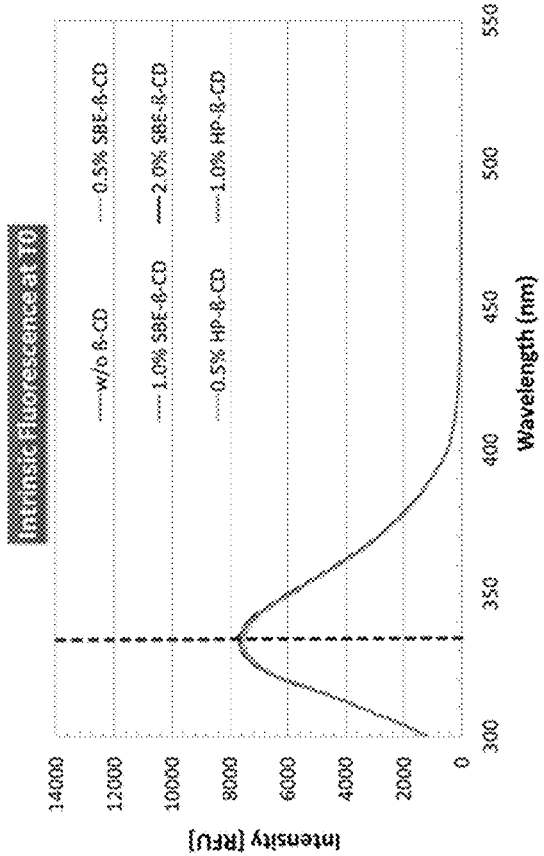

Optical densities (OD) at 350 nm indicated a reduced aggregation propensity of AMG 103 in presence of HP-β-CD or SBE-β-CD. The effect was more pronounced with increasing cyclodextrin concentrations (FIG. 3). The aggregation of AMG 103 in presence of benzyl alcohol translates into a change of the local environment tryptophan residues demonstrated by intrinsic fluorescence. These changes were minimized with increasing concentrations of the different β-CDs (FIG. 4).

Example 4

Effect of Benzyl Alcohol on Formulations Comprising Different Concentrations of AMG103 and β-CD The effect of increased concentrations of HP-β-CD and SBE-β-CD on the aggregation propensity of AMG 103 (blinatumomab) was addressed by a 2-level 4-factor full factorial experimental design. AMG 103 was formulated as described under Example 2. However its concentration was varied between 0.2 and 0.6 mg/mL (Table 2).

TABLE 2

2-level, 4-factor full factorial experimental design to assess the effect of SBE-β-CD and HP-β-CD on the aggregation propensity of AMG 103 in presence of benzyl alcohol

| β-CD type | β-CD concentration % w/V | AMG 103 concentration mg/mL | Benzyl alcohol concentration % V/V |
|---|---|---|---|
| HP-β-CD | 0.2 | 0.2 | 0.5 |
|  |  |  | 0.9 |
|  |  | 0.6 | 0.5 |
|  |  |  | 0.9 |
|  | 0.6 | 0.2 | 0.5 |
|  |  |  | 0.9 |
|  |  | 0.6 | 0.5 |
|  |  |  | 0.9 |
| SBE-β-CD | 0.2 | 0.2 | 0.5 |
|  |  |  | 0.9 |
|  |  | 0.6 | 0.5 |
|  |  |  | 0.9 |
|  | 0.6 | 0.2 | 0.5 |
|  |  |  | 0.9 |
|  |  | 0.6 | 0.5 |
|  |  |  | 0.9 |

All samples were incubated directly in a transparent half area 96 well plates (Corning) at 37° C. for 96 hours. The plate was covered with an adhesive foil to avoid evaporation losses. Again optical densities at 350 nm were taken as a measure for aggregation of AMG 103 (see Example 3).

Figure 5A:
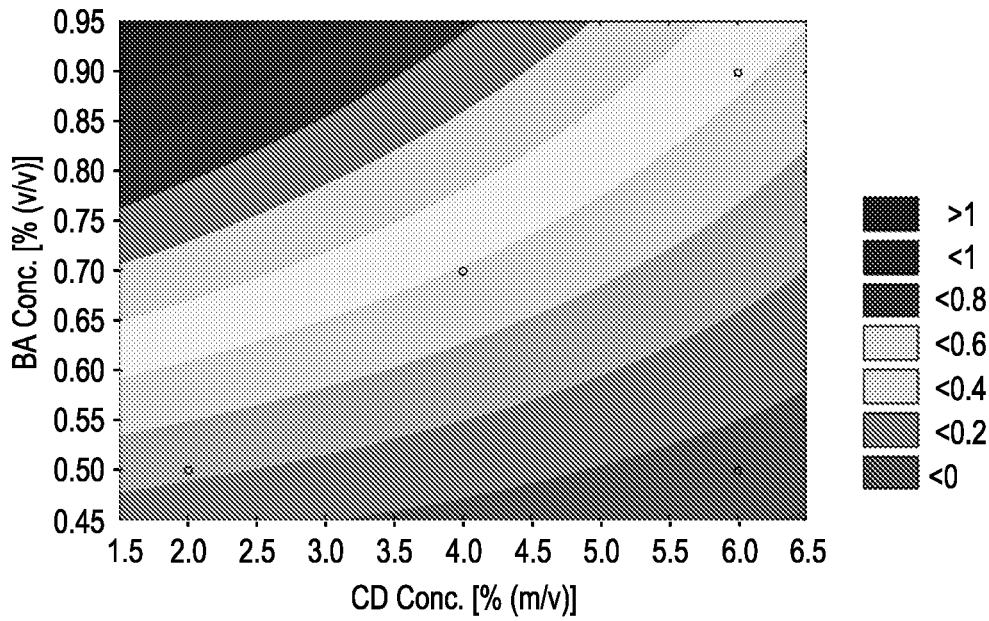
FIGS. 5A-5B: Predictive models derived from experimental design studies (2-level 4-factor full factorial) describing the effect of increasing concentrations of HP-β-CD (FIG. 5A) and SBE-β-CD (FIG. 5B) on the optical density at 350 nm of AMG 103 (SEQ ID NO: 174) preparations.
Figure 5B:
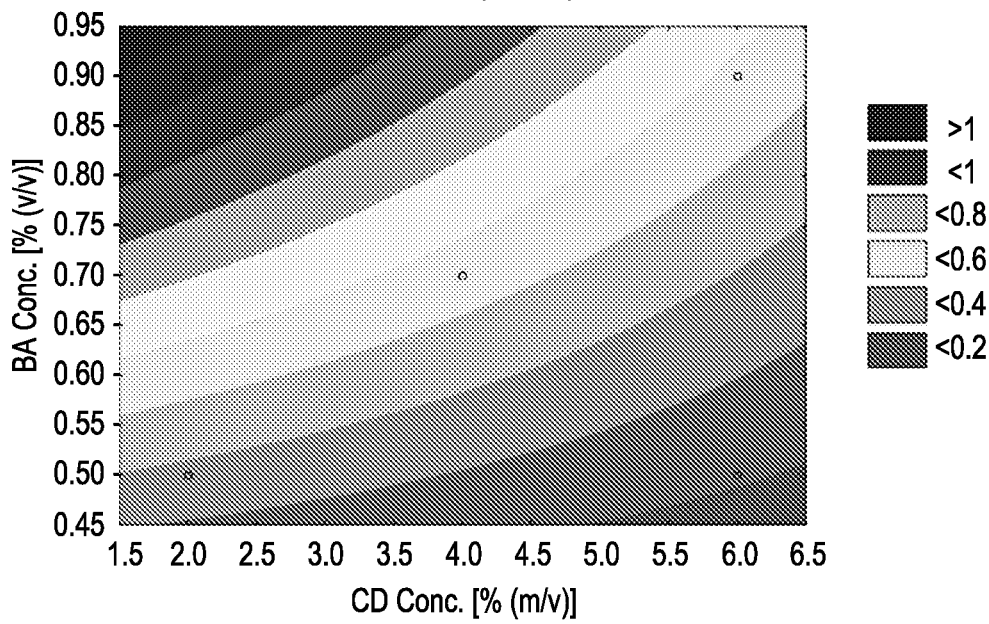

Analytical data were evaluated via analysis of variance (ANOVA) using Statistica® software. The normal distribution of measured values was graphically verified by plotting expected normal values against raw residuals. Predictive models (FIGS. 5A-5B) were generated by Statistica® based on regression of analytical data. Thereby, pure factor effects as well as linear interactions between factors were taken into account. At given concentrations of AMG 103 and benzyl alcohol, aggregation of AMG 103 could be reduced with increasing contents of either HP-β-CD or SBE-β-CD (FIGS. 5A-5B).

Example 5

Effect of Storage-Induced Stress on Formulations Comprising Bispecific Antibody Constructs and β-CD Preformulated drug substance containing approximately 1 mg/mL CD33_2-hALB in 20 mM potassium phosphate, 150 mM L-arginine hydrochloride and 6% (w/V) trehalose dihydrate at pH 6.0 was dialyzed in 20 mM citric acid, 6% (w/V) sucrose at pH 5.0 and in 20 mM potassium phosphate, 6% (w/V) sucrose at pH 6.0 respectively. The dialysis endpoint was determined via osmolality measurements. Dialysis was performed using Slide A Lyzer® devices. After dialysis the citrate buffered material was directly concentrated above 7 mg/mL with VivaSpin® units. Centrifugation was performed at approximately 2000 g for 5 min. at 2 to 8° C. The potassium phosphate buffered material was treated likewise. However the material was divided into two equally sized volume fractions prior to the centrifugation step. One fraction was adjusted to pH 7.0. The pH of the second fraction was maintained at pH 6.0. After sterile filtration through a 0.2 µm PVDF filter, the concentrates were finally formulated by adding stock solutions of polysorbate 80 and SBE-β-CD where applicable. The CD33_2-hALB target concentration was 5.0 mg/mL. The finally formulated bulks were filled into prewashed and presterilized type I glass vials. Vials were stoppered with sterilized butyl rubber stoppers and were sealed with aluminum caps. The fill volume totaled 1.0 mL. An overview on formulations is provided by Table 3. The vials were stored for six days in a temperature controlled cabinet at 37° C. High molecular weight species were quantified by SE-UPLC using the method described under Example 1. The injected amount of protein totaled 3 µg.

TABLE 3

Overview on CD33_2-hALB formulations

| ID | Citric acid | Potassium phosphate | Sucrose | SBE-β-CD | Poly-sorbate 80 | pH |
|---|---|---|---|---|---|---|
| C50SuT | 20 mM |  | 6% w/V |  | 0.01% w/V | 5.0 |
| C50SBESuT | 20 mM |  | 6% w/V | 1% w/V | 0.01% w/V | 5.0 |
| K60SuT |  | 20 mM | 6% w/V |  | 0.01% w/V | 6.0 |
| K60SBESuT |  | 20 mM | 6% w/V | 1% w/V | 0.01% w/V | 6.0 |
| K70SuT |  | 20 mM | 6% w/V |  | 0.01% w/V | 7.0 |
| K70SBESuT |  | 20 mM | 6% w/V | 1% w/V | 0.01% w/V | 7.0 |

Figure 6:
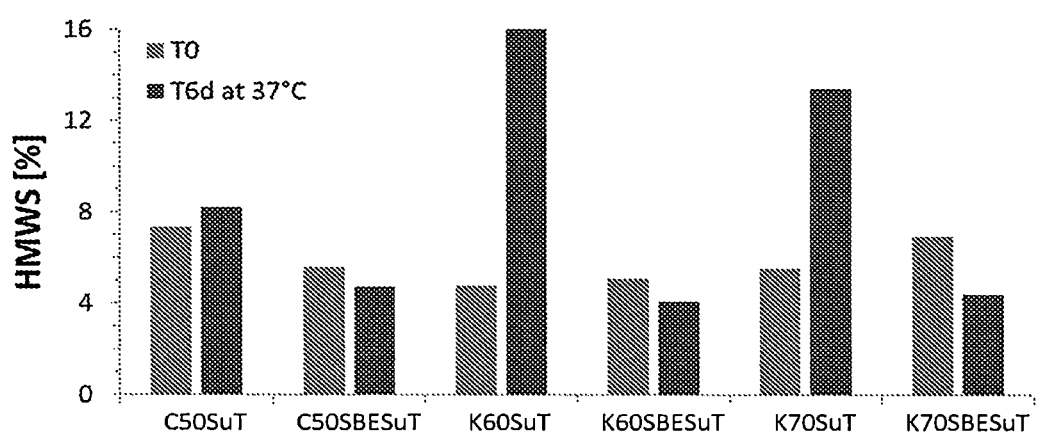
FIG. 6: Assessment of high molecular weight species (HMWS) by size exclusion chromatography in different formulations containing 5 mg/mL CD33_2-hALB (SEQ ID NO: 175).

Formulations containing SBE-β-CD (F2, F4, F6) showed lower amounts of high molecular weight species (HMWS) after incubation if compared to cyclodextrin free preparations. The effect was more pronounced at pH 6 and 7 than at pH 5 (FIG. 6).

Example 6

Effect of Ultrafiltration and Diafiltration on Formulations Comprising Bispecific Antibody Constructs and β-CD Purified MSLN-hALB (i.e., SEQ ID NO: 176) was concentrated stepwise by ultrafiltration (UF). First a seven fold concentration was performed using a cassette equipped with a regenerated cellulose membrane and surface of 0.11 m². A further seven fold concentration was carried out with a smaller membrane with a surface of 50 cm². Both membranes had a molecular weight cut-off (MWCO) of 10 kDa. For ultrafiltration and diafiltration steps the transmembrane pressure was limited to 1.4 bar. The concentrated pool was divided into two parts. The first part was dialfiltrated into a buffer composed of 20 mM potassium phosphate, 150 mM L-arginine hydrochloride, 6% (w/V) trehalose dihydrate at pH 6.0. The second part was diafiltrated into a buffer composed of 20 mM potassium phosphate, 2% (w/V) Sucrose at pH 6.0. The final formulations listed in Table 4 were adjusted by adding concentrated stock solutions to the diafiltrated materials. All excipients were applied in compendial grade. The target MSLN-hALB concentration was 1.0 mg/mL.

TABLE 4

Overview on MSLN-hALB formulations

| ID | Formulation composition |
| --- | --- |
| K60RTrT-low | 20 mM potassium phosphate, 150 mM L-arginine HCl, 6% (w/V) trehalose dihydrate, 0.01.% (w/V) polysorbate 80, pH 6.0 |
| K60SBESuT-low | 20 mM potassium phosphate, 1% (w/V) SBE-β-CD, 8% (w/V) Sucrose, 0.01% (w/V) polysorbate 80, pH 6.0 |
| K60RMSuT-low | 20 mM potassium phosphate, 150 mM L-arginine HCl, 4% (w/V) mannitol, 2% (w/V) sucrose, 0.01.% (w/V) polysorbate 80, pH 6.0 |

Finally MSLN-hALB drug substance was sterile filtered through a 0.2 μm PVDF filter and filled into prewashed and presterilized type I glass vials. Vials were stoppered with sterilized butyl rubber stoppers and were sealed with aluminum caps. The fill volume totaled 1.0 mL. The vials were stored for up to two weeks in temperature controlled cabinets at 25° C. and 37° C. respectively. High molecular weight species were quantified by SE-UPLC using the method described under Example 1. The injected amount of protein totaled 3 μg. Acidic charge variants were determined using weak cation exchange ultra high performance liquid chromatography (WCX-UPLC). WCX-UPLC was performed on a UPLC H class Aquity (Waters) using a Protein-Pak Hi Res CM 7 μm 4.6×100 mm column. The column temperature was set to 30° C. In order to achieve chromatographic separation the following gradient (Table 5) was applied:

TABLE 5

Overview on WCX-UPLC gradient

| Time [min:sec] | % Eluent A | % Eluent B |
| --- | --- | --- |
| 0:00 | 100 | 0 |
| 4:00 | 100 | 0 |
| 25:00 | 50 | 50 |
| 25.01 | 0 | 100 |
| 29:00 | 0 | 100 |
| 29:01 | 100 | 0 |
| 33:00 | 100 | 0 |

Eluent A was composed of 20 mM sodium phosphate at pH 6.5. Eluent B was composed of 20 mM sodium phosphate, 250 mM sodium chloride, pH 6.5. The injected amount of protein totaled 3 μg. The flow rate was 0.65 mL/min. Prior to injection, samples were held in the autosampler at 8° C. Protein detection relied on the measurement of intrinsic fluorescence intensity. Excitation was performed at 280 nm and emission was taken at 330 nm. Acidic charge variants were quantified based on the relative area under the curve (AUC). Integration was performed using Empower® software.

Figure 7A:
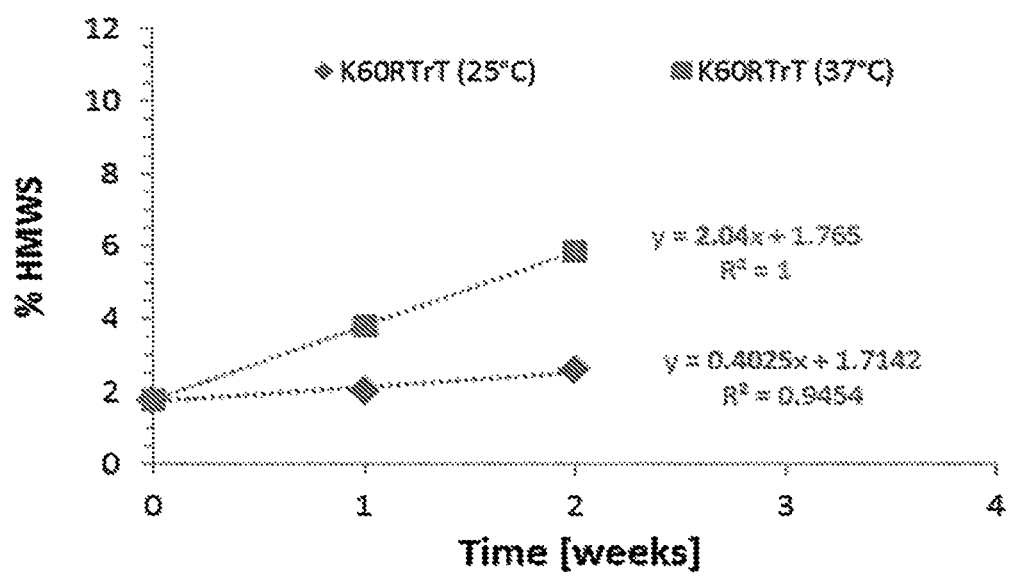
FIGS. 7A-7C: High molecular weight species formation rate at 25° C. and 37° C. for three different MSLN-hALB (SEQ ID NO: 176) formulations (K60RTrT (FIG. 7A), K60SBESuT (FIG. 7B), and K60RMSuT (FIG. 7C)) determined by the size exclusion chromatography (SEC)
Figure 7B:
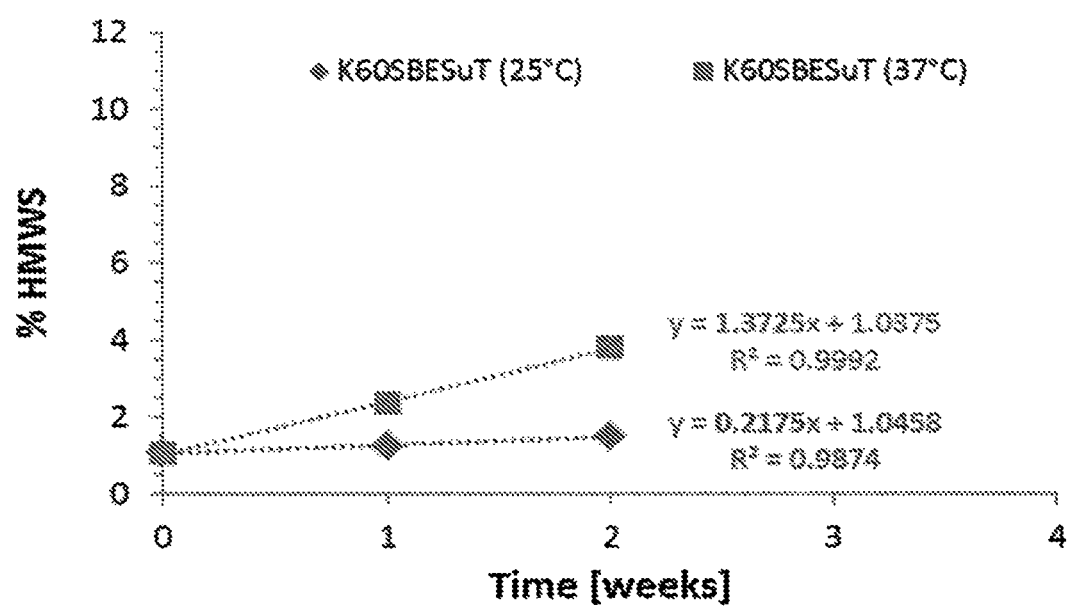
Figure 7C:
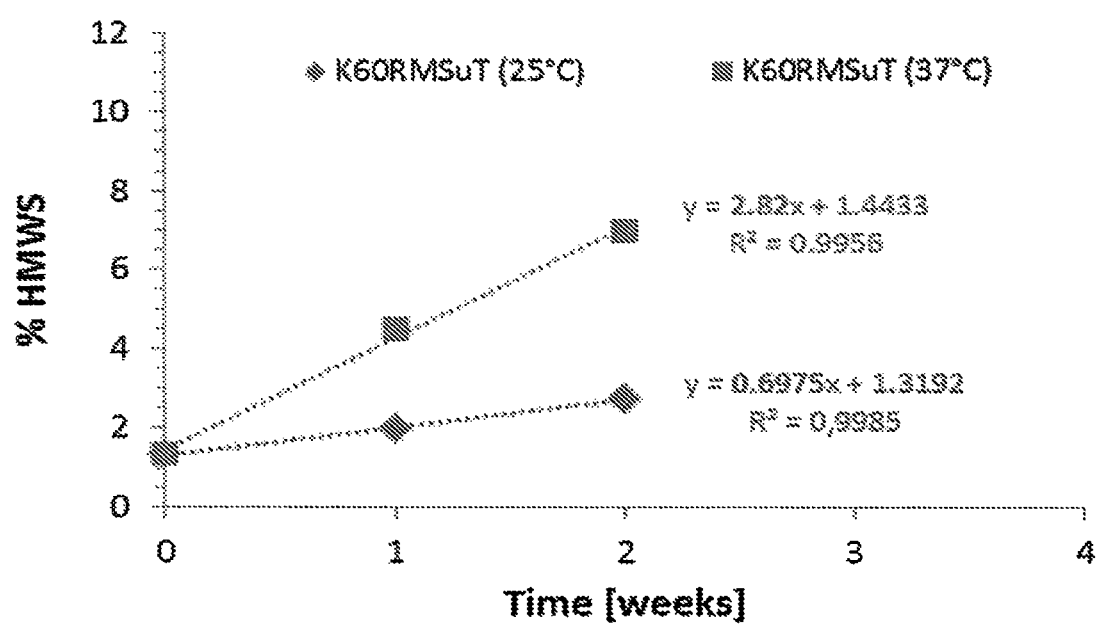
Figure 8:
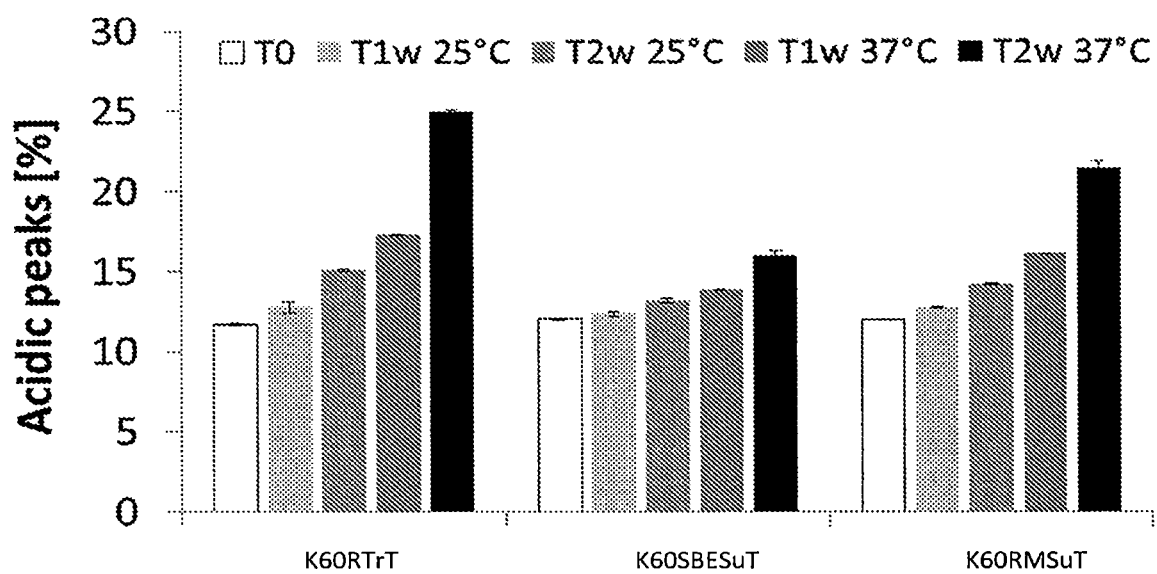
FIG. 8: Formation of acidic charge variants at 25° C. and 37° C. for three different MSLN-hALB formulations determined by weak cation exchange ultra high performance liquid chromatography (WCX-U PLC)

The lowest high molecular weight species (HMWS) formation rates were observed for the formulation with SBE-β-CD (FIG. 7B). The chemical stability was also most pronounced for the SBE-β-CD containing formulation indicated by the lowest fraction of acidic charge variants (FIG. 8).

Example 7

LLPS of AMG 330 with SBE-β-CD and Alginate

LLPS: Liquid-Liquid Phase Separation (LLPS) is caused by net attraction between the colloidal particles (e.g. proteins) and thus is measure of strength of this attraction. When there is attraction between proteins, a LLPS occurs into coexisting protein-rich and protein-poor phases, provided the temperature is sufficiently low. In LLPS, the co-existing phases are in true thermodynamic equilibrium and are fully reversible and the concentrations of the coexisting phases depend only on temperature and not on the initial protein concentration.

LLPS can be induced by addition of PEG. If there is a stronger the attraction between proteins, the lower the PEG concentration that is necessary for LLPS to occur, which in turn indicates that these proteins will easily aggregate. At a given temperature and PEG concentration, excipients that increase colloidal stability of a protein result in a higher protein concentration in protein-poor phase. This increase in protein concentration can be measured chromatographically relative to a control without an excipient. In formulation development it is desirable to observe LLPS and evaluate the attraction between protein molecules.

The purpose of this experiment is to use LLPS to evaluate the effect of SBE-β-CD and Alginate on the colloidal stability of AMG 330.

TABLE 6

Solution composition and preparation:

| Solution ID | Solution Composition | Solution Preparation | Volume |
| --- | --- | --- | --- |
| A | AMG 330 (1.2 mg/ml) | n/a | 180 uL needed |
| B | 1X PBS | 5 mL 10X PBS + 45 mL milli Q water | 50 mL |

TABLE 6-continued

Solution composition and preparation:

| Solution ID | Solution Composition | Solution Preparation | Volume |
|---|---|---|---|
| C | 50% SBE-β-CD in 1X PBS (pH to match 1x PBS) | 5 g in 10 g | |
| D | 1% SBE-β-CD in 1X PBS | 100 uL C + 4.9 mL B | 5 mL |
| E | 0.1% SBE-β-CD in 1X PBS | 10 uL + 4.99 mL B | 5 mL |
| F | 1% Alginate in 1x PBS (pH to match 1X PBS) | 0.2 g in 20 g | |
| G | 0.1% Alginate in 1x PBS | 500 uL F + 4.5 mL B | 5 mL |
| H | 24% PEG 3350 IN 1X PBS | 4.8 g in 20 g | |

TABLE 7

Sample composition and preparation:

| Sample ID | Sample Composition | Sample preparation | Final volume (uL) |
|---|---|---|---|
| 1-1 | AMG 330 + 1x PBS, 0% PEG | (10 uL A + 40 uL B) + 50 uL B | 100 |
| 1-2 | AMG 330 + 1x PBS, 0% PEG | (10 uL A + 40 uL B) + 50 uL B | 100 |
| 2-1 | AMG 330 + 1x PBS, 12% PEG | (10 uL A + 40 uL B) + 50 uL H | 100 |
| 2-2 | AMG 330 + 1x PBS, 12% PEG | (10 uL A + 40 uL B) + 50 uL H | 100 |
| 3-1 | AMG 330 + 0.001% SBE-β-CD, 12% PEG | (10 uL A + 1 uL E + 39 uL B) + 50 uL H | 100 |
| 3-2 | AMG 330 + 0.001% SBE-β-CD, 12% PEG | (10 uL A + 1 uL E + 39 uL B) + 50 uL H | 100 |
| 4-1 | AMG 330 + 0.01% SBE-β-CD, 12% PEG | (10 uL A + 1 uL D + 39 uL B) + 50 uL H | 100 |
| 4-2 | AMG 330 + 0.01% SBE-β-CD, 12% PEG | (10 uL A + 1 uL D + 39 uL B) + 50 uL H | 100 |
| 5-1 | AMG 330 + 0.1% SBE-β-CD, 12% PEG | (10 uL A + 10 uL D + 30 uL B) + 50 uL H | 100 |
| 5-2 | AMG 330 + 0.1% SBE-β-CD, 12% PEG | (10 uL A + 10 uL D + 30 uL B) + 50 uL H | 100 |
| 6-1 | AMG 330 + 1% SBE-β-CD, 12% PEG | (10 uL A + 2 uL C + 38 uL B) + 50 uL H | 100 |
| 6-2 | AMG 330 + 1% SBE-β-CD, 12% PEG | (10 uL A + 2 uL C + 38 uL B) + 50 uL H | 100 |
| 7-1 | AMG 330 + 0.001% Alginate, 12% PEG | (10 uL A + 1 uL G + 39 uL B) + 50 uL H | 100 |
| 7-2 | AMG 330 + 0.001% Alginate, 12% PEG | (10 uL A + 1 uL G + 39 uL B) + 50 uL H | 100 |
| 8-1 | AMG 330 + 0.01% Alginate, 12% PEG | (10 uL A + 1 uL F + 39 uL B) + 50 uL H | 100 |
| 8-2 | AMG 330 + 0.01% Alginate, 12% PEG | (10 uL A + 1 uL F + 39 uL B) + 50 uL H | 100 |
| 9-1 | AMG 330 + 0.1% Alginate, 12% PEG | (10 uL A + 10 uL F + 30 uL B) + 50 uL H | 100 |
| 9-2 | AMG 330 + 0.1% Alginate, 12% PEG | (10 uL A + 10 uL F + 30 uL B) + 50 uL H | 100 |

Different solution/sample composition and preparation was prepared as mentioned in the table 6 and 7 above. Samples were prepared (final AMG 330 concentration of 0.12 mg/ml) and incubated at 40° C. for three days. Samples were then micro centrifuged (Eppendorf Centrifuge 5418, St. Louis, Mo., USA) for 20 sec and 80 uL supernatant was removed and analyzed by analytical CEX (ProPac WCX-10 column, 2 mm ID) in Agilent chromatography system (Agilent 1200, Santa Clara, Calif., USA).

Figure 9:
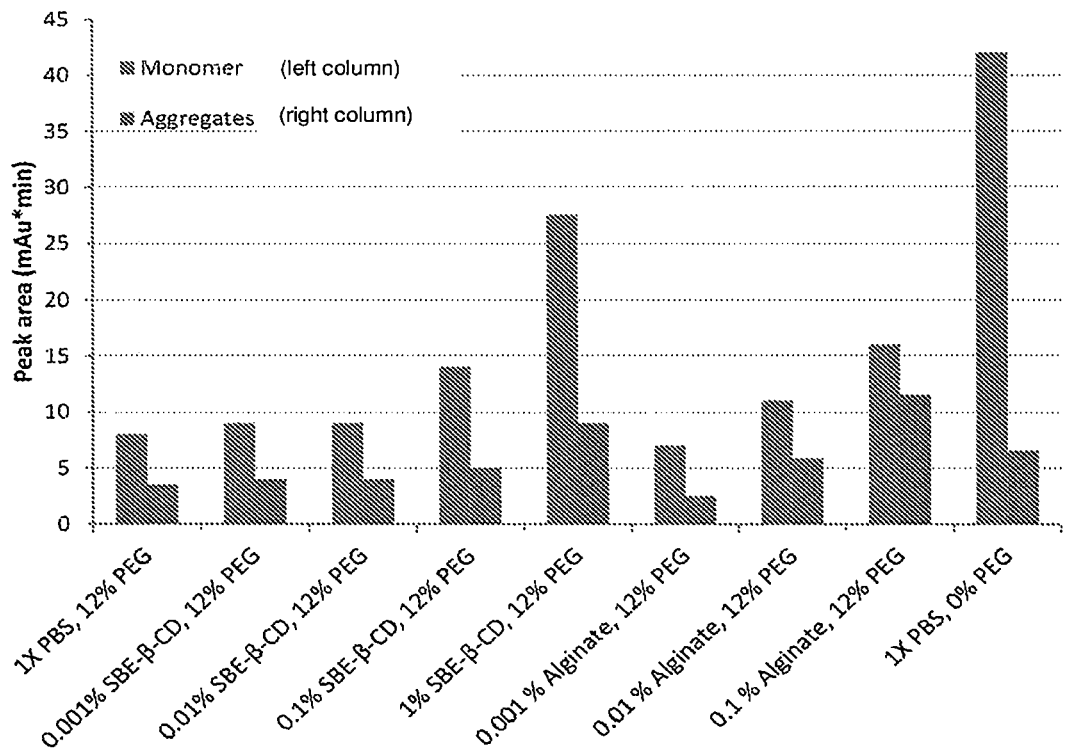
FIG. 9. AMG 330 solubility at 40 C in the presence of 12% PEG-3350. Both SBE-β-CD (Captisol) and Alginate (Protanal) increase solubility of aggregated and monomeric AMG 330 when used at higher concentrations. However, SBE-β-CD preferentially solubilizes monomer. The control on the left (1×PBS) was incubated without SBE-β-CD, whereas the control on the right (1×PBS) was incubated without PEG and SBE-β-CD.
Figure 10:
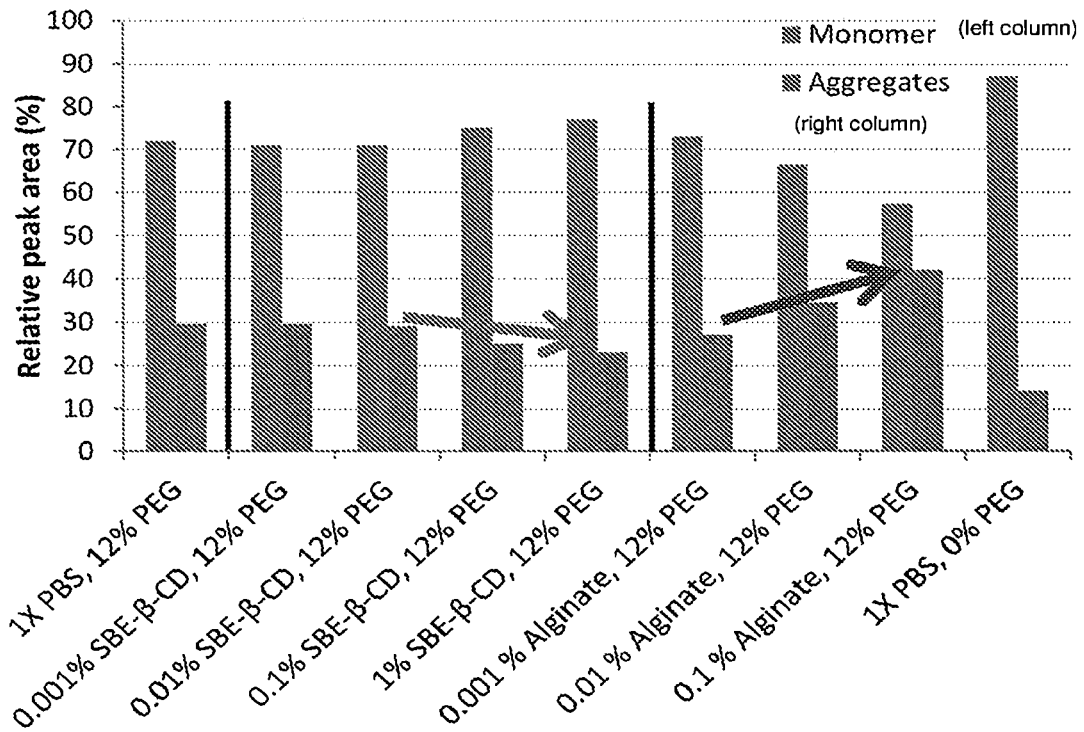
FIG. 10: Data from the same experiment as shown in FIG. 9 that demonstrates the effect of different concentrations of SBE-β-CD and Alginate on % monomer and % aggregate in AMG 330. SBE-β-CD at ~0.1-1% is effective at increasing monomer content at the expense of aggregates (shown by green arrows). In contrast, Alginate data shows opposite trend of increasing aggregates (shown by red arrow). SBE-β-CD was also shown to reduce the negative impact of overconcentration in this case.

Analytical CEX: 70 μL of the sample were injected into the CEX column which was equilibrated with 20 mM Citric acid, 0.005% Sodium Azide, pH 6.0 and eluted with 20 mM Citric acid, 1M Sodium Chloride, 0.005% Sodium Azide pH 6.0, with a gradient time of 30 min (total run time: 45 min/injection) with a maximum concentration of 500 mM Sodium chloride at a flow rate of 0.2 mL/min. Autosampler temperature were maintained at 40 C during the run. From the chromatograms, peak areas of the samples were calculated (FIGS. 9 and 10).

Example 8

Buffer Exchange and Protein Concentration of AMG 330 by Ultrafiltration Centrifugation in the Presence of 4 Different Formulations (Including SBE-β-CD)

TABLE 8

Solution composition and preparation (Volume in mL):

| Solution ID: | Solution composition | Solution preparation | Vol to prepare |
|---|---|---|---|
| A | 0.4 mg/mL, AMG 330 | N/A | 17 mL |
| B | 10 mM Citrate, pH 6.0 | N/A | N/A |
| C | 40% Captisol in 1X PBS | N/A | N/A |
| D | 500 mM Arg, 500 mM Glu in B, pH 6.0 | N/A | N/A |
| E | 35 mM Tris, 17.5 mM Na phosphate, 50 mM Arg, 1.4% Trehalose, pH 6.0 | N/A | N/A |
| F | 65% Sucrose (w/v) in B | N/A | N/A |
| G | 18% Mannitol (w/w) in B | N/A | N/A |
| H | 1% Polysorbate 80 (w/w) in B | N/A | N/A |
| I | 1% PEG 4000 (w/w) in E, pH 6.0 | N/A | N/A |
| J | 10 mM Citrate pH 6.0, 1% Captisol | 97.5 mL B + 2.5 mL C | 100 mL |

TABLE 8-continued

Solution composition and preparation (Volume in mL):

| Solution ID: | Solution composition | Solution preparation | Vol to prepare |
|---|---|---|---|
| K | 35 mM Tris, 17.5 mM Na phosphate, 50 mM Arg, 1.4% Trehalose, 0.05% PEG 4000, pH 6.0 | 95 mL E + 5 mL I | 100 mL |
| L | 10 mM Citrate, 50 mM Arg, 50 mM Glu, 2% Sucrose, 4% Mannitol, 0.01% PS-80, pH 6.0 | 63.8 mL B + 10 mL D + 3.1 mL F + 22.2 mL G + 1 mL H | 100 mL |

TABLE 9

Sample Composition and preparation:

| Sample ID | Sample Composition | Sample preparation |
|---|---|---|
| 1-1 | AMG 330 in 10 mM Citrate, pH 6.0 | 2 mL A, buffer exchange in B by centrifugation/filtration |
| 1-2 | AMG 330 in 10 mM Citrate, pH 6.0 | 2 mL A, buffer exchange in B by centrifugation/filtration |
| 2-1 | AMG 330 in 10 mM Citrate, pH 6.0%, 1% Captisol | 2 mL A, buffer exchange in J by contrifugation/filtration |
| 2-2 | AMG 330 in 10 mM Citrate, pH 6.0%, 1% Captisol | 2 mL A, buffer exchange in J by contrifugation/filtration |
| 3-1 | AMG 330 in 35 mM Tris, 17.5 mM Na phosphate, 50 mM Arg, 1.4% Trehalose, 0.05% PEG 4000 pH 6.0 | 2 mL A, buffer exchange in K by contrifugation/filtration |
| 3-2 | AMG 330 in 35 mM Tris, 17.5 mM Na phosphate, 50 mM Arg, 1.4% Trehalose, 0.05% PEG 4000 pH 6.0 | 2 mL A, buffer exchange in K by contrifugation/filtration |
| 4-1 | AMG 300 in 10 mM Citrate, 50 mM Arg, 50 mM Glu, 2% Sucrose, 4% Mannitol, 0.01% PS-80, pH 6.0 | 2 mL A, buffer exchange in L by contrifugation/filtration |
| 4-2 | AMG 300 in 10 mM Citrate, 50 mM Arg, 50 mM Glu, 2% Sucrose, 4% Mannitol, 0.01% PS-80, pH 6.0 | 2 mL A, buffer exchange in L by contrifugation/filtration |
| 5-1 | AMG 330, no buffer exchange | 110 uL A into HPLC vials |
| 5-2 | AMG 330, no buffer exchange | 110 uL A into HPLC vials |

Initial protein concentration was 0.4 mg/ml. 2 mL of 0.4 mg/ml AMG 330 were placed into an Amicon ultra 15 ml centrifugal filter, MWCO 10,000. 10 mL of the appropriate buffer were added to each tube and gently mixed with protein and centrifuged (Allegra 6R Centrifuge, Beckman Coulter, Brea, Calif., USA) for 3 hrs at 2000 rpm at 4° C. The retentate was then gently mixed and the tubes were centrifuged for 1.5 hrs at 2500 rpm at 25° C. Following a retentate volume of 200-250 μL, 10 mL of appropriate buffer was added to each and gently mixed with the retentate and then centrifuged for 30 min at 2500 rpm at 25° C. to a final volume of 200-250 μL. Final protein concentration in 4 different formulations ranged from 2.9 to 3.7 mg/ml.

Analytical SEC: Samples were analyzed by analytical SEC (TSKgel G3000SWXL, 7.8 mm ID, PA, USA) in an Agilent chromatography system (Agilent 1200, Santa Clara, Calif., USA) with a running buffer of 100 mM sodium phosphate, 250 mM Sodium chloride, pH 6.8 with a flow rate of 0.5 mL/min (total run time: 35 min/injection). Autosampler temperature was maintained at 4° C. during the run.

Figure 11:
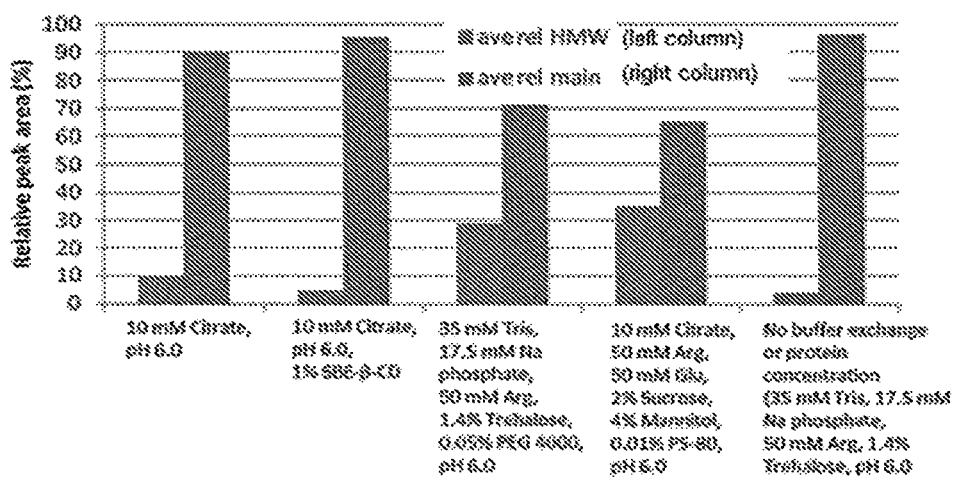
FIG. 11: Average SEC relative peak area of AMG 330 after buffer exchange and protein concentration by ultrafiltration/centrifugation.

The presence of SBE-β-CD appears to provide significant protection to AMG 330 against the formation of HMW during protein concentration by ultrafiltration with the lowest relative amount of aggregates in formulation containing SBE-β-CD. The formulation containing Arginine, Glutamate, Sucrose, Mannitol and PS-80 had the highest amount of HMW followed by the formulation containing Tris, phosphate, Arginine, Trehalose and PEG 4000 (FIG. 11). CEX analysis showed similar effect (data not shown).

Example 9

Small Scale Formulation Study of AMG 330 Including SBE-β-CD (LLPS, FT, UFC)

Figure 12A:
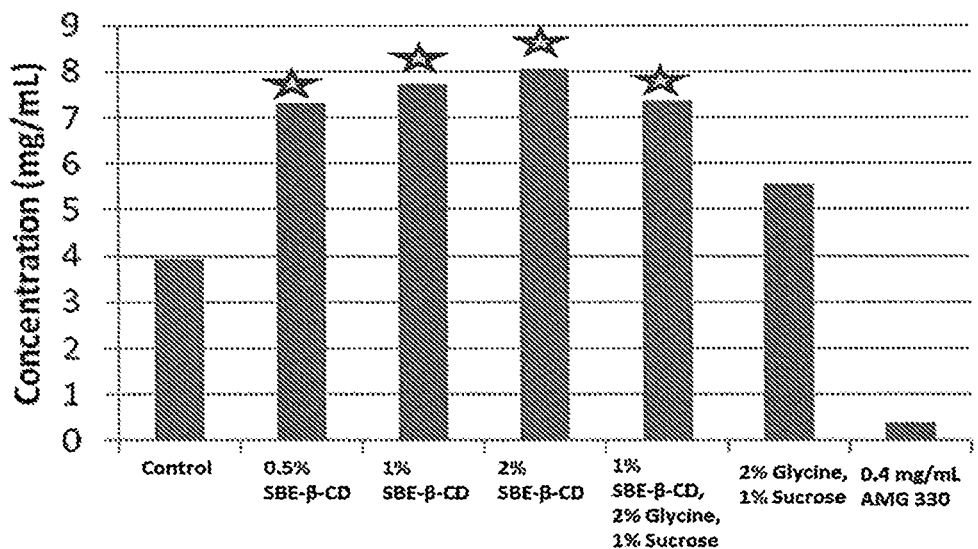
FIGS. 12A-12D.
Figure 12B:
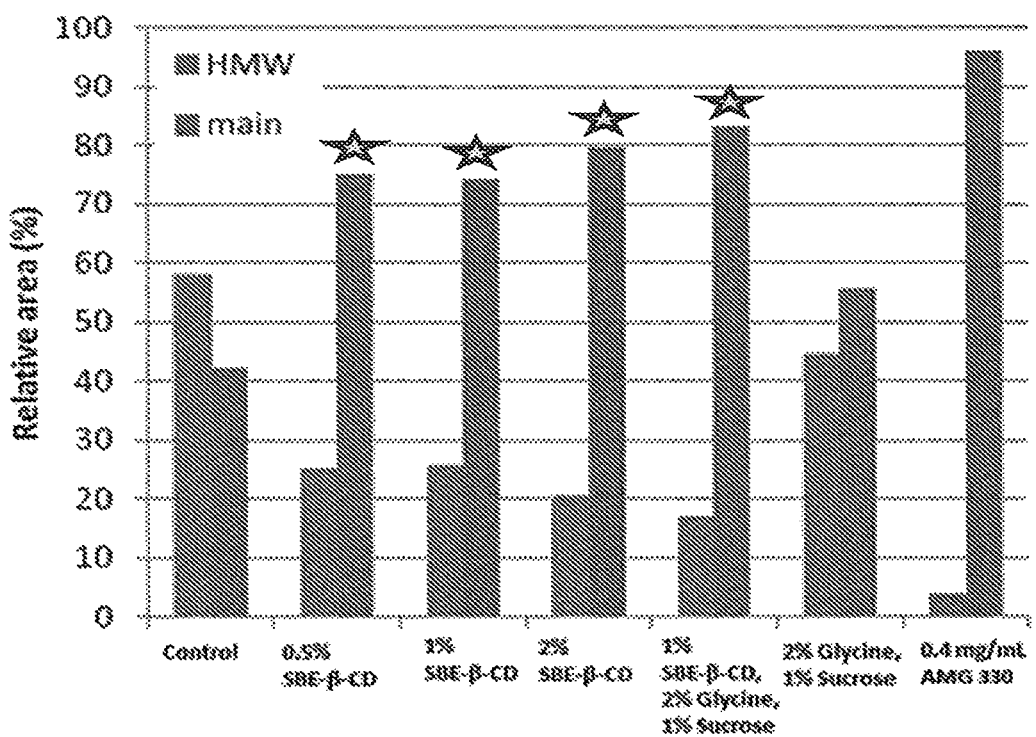
Figure 12C:
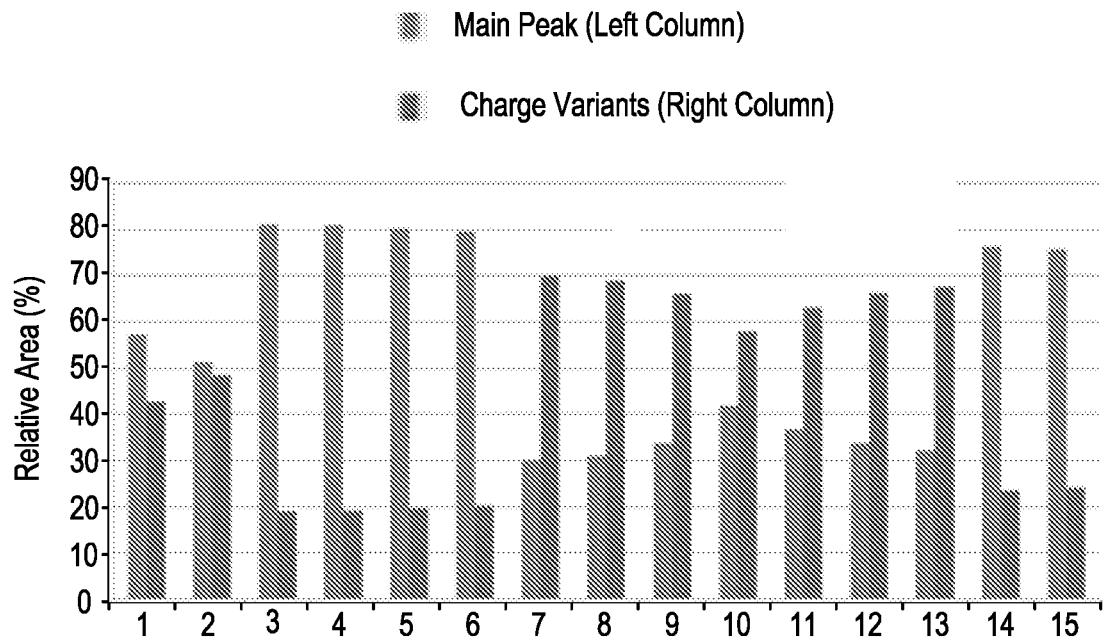
Figure 12D:
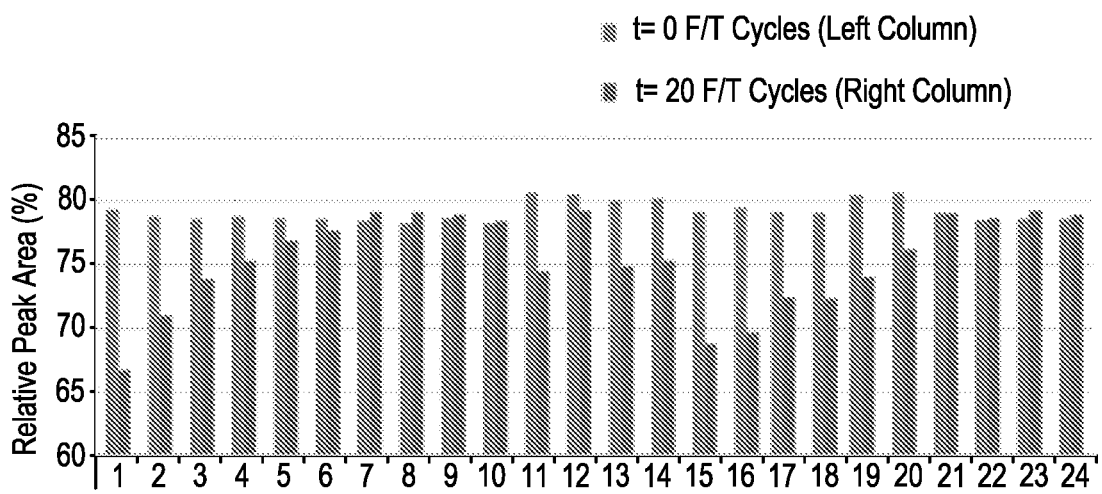

The purpose of this experiment is to evaluate the stability of AMG 330 after various stresses in 14 different formulations. Specifically, AMG 330 was evaluated after LLPS, 20 freeze/thaw (F/T) cycles and concentration by ultrafiltration/centrifugation (UFC). As shown in Example 8, SBE-β-CD provides protection against AMG 330 aggregation and is further evaluated in this experiment. For UFC (FIG. 12A, FIG. 12B), only 5 formulations were investigated. For LLPS and F/T studies (FIG. 12C, FIG. 12D), 14 formulations were investigated. LLPS samples were analyzed by analytical CEX, whereas UFC and F/T samples were analyzed by both analytical SEC and CEX.

Materials and Methods:

TABLE 10

Stock solution preparation:

| Solution ID | Solution composition | Solution preparation | volume |
|---|---|---|---|
| A | 20 mM Citrate pH 6.0 | by media prep | 20 L |
| B | ~2 mg/mL AMG 330, buffer exchange in A | dialysis of 0.4 mg/mL AMG 330, then concentration by ultrafiltration/centrifugation | 20 mL, concentrate to 4 mL |
| C | 1% Polysorbate 80 (w/w) in A | 1 g, bring to 100 g in A | 100 mL |
| D | 10% SBE-β-CD (w/w) in A, pH 6.0 | 5 g, bring to 50 g in A, pH adjust to 6.0 | 50 mL |
| E | 15% Glycine in (w/w) in A, pH 6.0 | 7.5 g, bring to 50 g in A, pH adjust in 6.0 | 50 mL |
| F | 40% Sucrose (w/w) in A | 10 g, bring to 25 g in A | 25 mL |
| G | 14% Mannitol (w/w) in A | 3.5 g, bring 25 g in A | 25 mL |
| H | 400 mM Arg in A, pH 6.0 | 3.484 g Arg, bring to 50 mL in A, pH adjust to 6.0 | 50 mL |
| I | 200 Mm Arg, 200 mM Glu in A, pH 6.0 | 1.742 g Arg, + 1.471 g Glu bring to 50 mL in A, pH adjust to 6.0 | 50 mL |
| J | 15% Trehalose dihydrate (w/w) in A | 3.75 g, bring 25 g in A | 25 mL |
| K | 26% PEG 3350 (w/w) in A, pH 6.0 | 10.4 g, bring to 40 g in A, pH adjust to 6.0 | 40 mL |
| L | 1.93 mg/mL AMG 330 + 0.074% PS80 | 2100 uL B + 168 uL C | 2268 uL |
| M | 40% SBE-β-CD (w/w) in A, pH 6.0 | 6 g, bring to 15 g in A, pH adjust to 6.0 | 15 mL |
| N | 55% Sucrose (w/w) in A | 13.75 g, bring to 25 g in A | 25 mL |

Ultrafiltration/Centrifugation (UFC):

TABLE 11

Sample composition preparation for UFC (Volume in μL).

| Sample ID | Sample composition | 20 mM Cit A | PS-80 C | Capitsol D | Glysine E | Sucrose F |
|---|---|---|---|---|---|---|
| 2-1_UFC | control | 79.2 | 0.8 | | | |
| 3-1_UFC | 0.5% SBE-β-CD | 75.2 | 0.8 | 4 | | |
| 4-1_UFC | 1% SBE-β-CD | 71.2 | 0.8 | 8 | | |
| 5-1_UFC | 2% SBE-β-CD | 63.2 | 0.8 | 16 | | |
| 6-1_UFC | 2% SBE-β-CD, 2% Glysine, 1% Sucrose | 58.5 | 0.8 | 8 | 10.7 | 2 |
| 8-1_UFC | 2% Glycine, 1% Sucrose | 66.5 | 0.8 | | 10.7 | 2 |

For each sample, 4 mL of 0.4 mg/mL AMG 330 were placed into an Amicon Ultra 15 ml centrifugal filter tube of MWCO 10,000. 8 mL of the appropriate buffer were added to each tube and gently mixed with protein and centrifuged (Allegra 6R Centrifuge, Beckman Coulter, Brea, Calif., USA) at 2000 rpm (4000 rcf) at 20° C. until the retentate volume was 200-250 uL. This process were repeated twice more for a total of 3 concentration steps. The retentate was then gently mixed with a pipettor removed from the filter tube, placed in an Eppendorf tube and micro-centrifuged (Eppendorf Centrifuge 5418, St. Louis, Mo., USA) at maximum speed for 2 min. Following this, protein concentration was measured for the supernatant, and analyzed by analytical SEC (same details as in Example 8) by injecting 20 μL. Each sample was prepared in duplicate.

LLPS:

Samples were prepared as outlined in table below and incubated for 5 days at 4° C. The final volume of all the samples was 240 μL. After incubation, samples were micro centrifuged (Eppendorf Centrifuge 5418, St. Louis, Mo., USA) for 20 s, then 200 μL supernatant was removed for analytical CEX (same details as in Example 7), except the autosampler temperature was maintained at 25° C.

TABLE 12

Sample composition preparation for LLPS:

| ID | Sample composition | 20 mM Citrate, pH 6.0 A | AMG 330 + PS80 L | 40% SBE-β-CD M | Glycine E | 55% Sucrose N | Mannitol G | Arginine H | Arginine + Glutamate I | Trehalose J | PEG K |
|---|---|---|---|---|---|---|---|---|---|---|---|
| 1 | Control, 0% PEG | 207.6 | 32.4 | | | | | | | | 0 |
| 2 | Control, 13% PEG | 87.6 | 32.4 | | | | | | | | 0 |
| 3 | 0.5% SBE-β-CD, PEG 13% | 84.6 | 32.4 | 3 | | | | | | | 120 |
| 4 | 1% SBE-β-CD, 13% PEG | 81.6 | 32.4 | 6 | | | | | | | 120 |
| 5 | 2% SBE-β-CD, 13% PEG | 75.6 | 32.4 | 12 | | | | | | | 120 |
| 6 | 1% SBE-β-CD, 1% Glycine, 1% Sucrose, 13% PEG | 45.2 | 32.4 | 6 | 32 | 4.4 | | | | | 120 |
| 7 | 4% Glycine, 13% PEG | 23.6 | 32.4 | | 64 | | | | | | 120 |
| 8 | 2% Glycine, 1% Sucrose, 13% PEG | 51.2 | 32.4 | | 32 | 4.4 | | | | | 120 |
| 9 | 4% Mannitol, 13% PEG | 19 | 32.4 | | | | 68.6 | | | | 120 |
| 10 | 100 mM Arginine, 13% PEG | 27.6 | 32.4 | | | | | 60 | | | 120 |
| 11 | 50 mM Arginine, 50 mM Glutamate, 13% PEG | 27.6 | 32.4 | | | | | | 60 | | 120 |
| 12 | 4% Sucrose, 13% PEG | 70.1 | 32.4 | | | 17.5 | | | | | 120 |
| 13 | 4% Trehalose dehydrate, 13% PEG | 23.6 | 32.4 | | | | | | | 64 | 120 |
| 14 | 1% SBE-β-CD, 4% Sucrose, 13% PEG | 64.1 | 32.4 | 6 | | 17.5 | | | | | 120 |
| 15 | 1% SBE-β-CD, 4% Mannitol, 2% Sucrose, 13% PEG | 4.3 | 32.4 | 6 | | 8.7 | 68.6 | | | | 120 |

Increasing concentrations of SBE-β-CD resulted in increased monomer recovery while maintaining relatively low level of aggregates. SBE-β-CD performed even better when in combination with sucrose, mannitol and sucrose, and especially with glycine and sucrose. This is especially striking because Glycine alone performed quite poorly and it didn't do much better in combination with sucrose.
Freeze/Thaw (F/T):

TABLE 13

Sample composition preparation for F/T:

| | Volume in uL | 20 mM Citrate, pH 6.0 | AMG 330 + PS80 | 40% SBE-β-CD | Glycine | 55% Sucrose | Mannitol | Arginine + Glutamate | Trehalose |
|---|---|---|---|---|---|---|---|---|---|
| ID | Sample composition | A | L | M | E | N | G | I | J |
| 1 | Control, −70 C. | 207.6 | 32.4 | | | | | | |
| 2 | Control, −30 C. | 207.6 | 32.4 | | | | | | |
| 3 | 0.5% SBE-β-CD, −70 C. | 204.6 | 32.4 | 3 | | | | | |
| 4 | 0.5% SBE-β-CD, −30 C. | 204.6 | 32.4 | 3 | | | | | |
| 5 | 1% SBE-β-CD, −70 C. | 201.6 | 32.4 | 6 | | | | | |
| 6 | 1% SBE-β-CD, −30 C. | 201.6 | 32.4 | 6 | | | | | |
| 7 | 2% SBE-β-CD, −70 C. | 195.6 | 32.4 | 12 | | | | | |
| 8 | 2% SBE-β-CD, −30 C. | 195.6 | 32.4 | 12 | | | | | |
| 9 | 1% SBE-β-CD, 2% Glycine, 1% Sucrose, −70° C. | 165.2 | 32.4 | 6 | 32 | 4.4 | | | |
| 10 | 1% SBE-β-CD, 2% Glycine, 1% Sucrose, −30 C. | 165.2 | 32.4 | 6 | 32 | 4.4 | | | |
| 11 | 4% Glycine, −70 C. | 143.6 | 32.4 | | 64 | | | | |
| 12 | 4% Glycine, −30 C. | 143.6 | 32.4 | | 64 | | | | |
| 13 | 2% Glycine, 1% Sucrose, −70 C. | 171.2 | 32.4 | | 32 | 4.4 | | | |
| 14 | 2% Glycine, 1% Sucrose, −30 C. | 171.2 | 32.4 | | 32 | 4.4 | | | |
| 15 | 4% Mannitol, −70 C. | 139 | 32.4 | | | | 68.6 | | |
| 16 | 4% Mannitol, −30 C. | 139 | 32.4 | | | | 68.6 | | |
| 17 | 50 mM Arginine, 50 mM Glutamate, −70 C. | 147.6 | 32.4 | | | | | 60 | |
| 18 | 50 mM Arginine, 50 mM Glutamate, −30 C. | 147.6 | 32.4 | | | | | 60 | |
| 19 | 4% Trehalose dehydrate, −70 C. | 143.6 | 32.4 | | | | | | 64 |
| 20 | 4% Trehalose dehydrate, −30 C. | 143.6 | 32.4 | | | | | | 64 |
| 21 | 1% SBE-β-CD, 4% Sucrose, −70 C. | 184.1 | 32.4 | 6 | | 17.5 | | | |
| 22 | 1% SBE-β-CD, 4% Sucrose, −30 C. | 184.1 | 32.4 | 6 | | 17.5 | | | |
| 23 | 1% SBE-β-CD, 4% Mannitol, 2% Sucrose, −70 C. | 124.3 | 32.4 | 6 | | 8.7 | 68.6 | | |
| 24 | 1% SBE-β-CD, 4% Mannitol, 2% Sucrose, −30 C. | 124.3 | 32.4 | 6 | | 8.7 | 68.6 | | |

Samples were prepared as tabulated above. 20 F/T cycles were performed, with samples stored for at least on hour at −70° C. or −30° C. during each freeze, and at room temperature for no more than one hour during thaw. Final volume of each sample was 240 µL. Aliquots were removed for analytical SEC (same as Example 8) analysis after 0 and 20 cycles.

The presence of SBE-β-CD appears to provide benefit toward reducing aggregation and increasing relative monomer levels during F/T in comparison to other formulations. The formulations in which SBE-β-CD was used in combination with other excipients also performed well, particularly with Glycine and Sucrose.

Example 10

Comparing the Effects of SBE-β-CD and 2-hydroxypropyl beta-cyclodextrin

SBE-β-CD has been shown in previous UFC experiment to provide significant protection to AMG 330 against aggregation during protein concentration. In the present experiment, the effects on AMG 330 during protein concentration by UFC are compared in the presence of either SBE-β-CD or another cyclodextrin, 2-Hydroxypropyl beta-cyclodextrin (2-HP-β-CD).

Materials and Methods:

20 mL of 0.4 mg/mL AMG 330 were concentrated to ~10 mL in Amicon Ultra 15 mL centrifugal filter tubes of MWCO 10,000. The retentate of the tubes were combined, and the concentration of the protein was then measured by SoloVPE (using extinction coefficient of 2.319 mL/(mg*cm)) and found to be 0.83 mg/mL. This protein was then used to prepare the UFC samples.

All samples contained 10 mM Potassium phosphate, 8% sucrose, 0.01% Polysorbate-80, pH 6.0.

Five formulation conditions were tested: 1) control with buffer only, 2) 1% SBE-β-CD added, 3) 2% SBE-β-CD added, 4) 1% 2-HP-β-CD added, and 5) 2% 2-HP-β-CD added. 50 mL of each of the 5 buffer solutions were prepared. Two replicate samples of each formulation were tested.

For each sample, 0.875 mL of AMG 330 was placed into an Amicon Ultra 4 mL centrifugal filter tube of MWCO 10,000. 3.125 mL of the appropriate buffer were added to each tube and mixed gently with the protein, and the tubes were centrifuged (Allegra 6R Centrifuge, Beckman Coulter, Brea, Calif., USA) at 4000 rcf at 25 C until retentate volume was ~100 uL. 4 mL additional buffer was added, and the samples were again concentrated to ~100 uL. The retentate was then gently mixed with a pipettor, and 45 uL were removed from the filter tube, placed in an Eppendorf tube, and micro-centrifuged (Eppendorf Centrifuge 5418, St. Louis, Mo., USA) at maximum speed for 2 min. The supernatant was analyzed by analytical SEC (same as Example 8). Non-concentrated AMG 330 (0.4 mg/mL) was also analyzed for comparison purposes.

Figure 13:
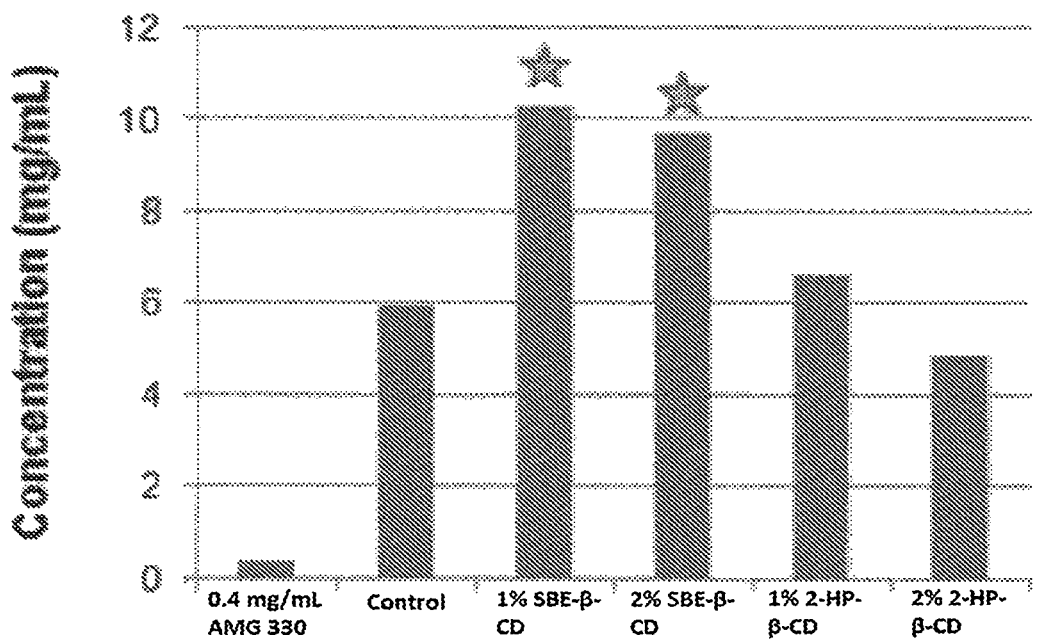
FIG. 13: AMG 330 concentration calculated from SEC main peak+HMW.
Figure 14:
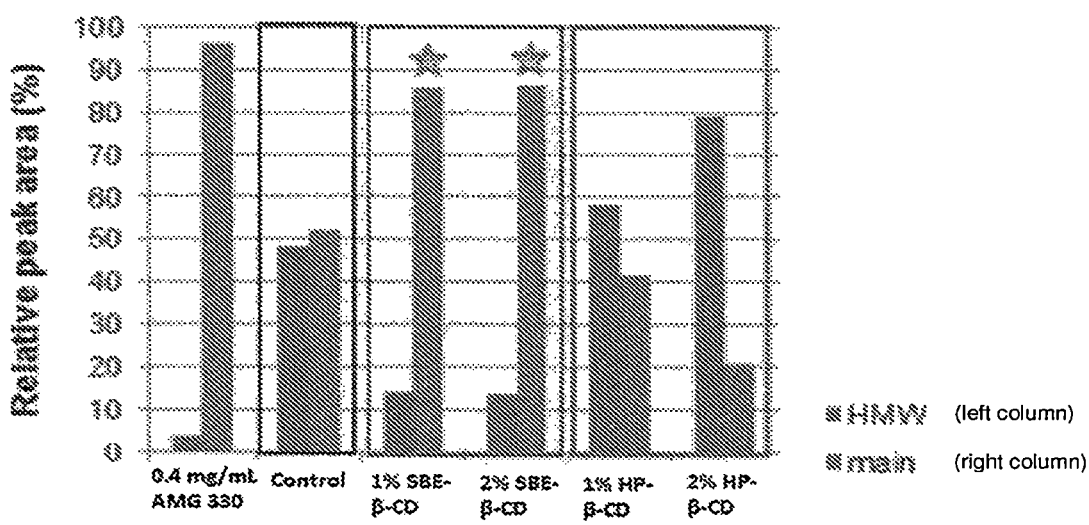
FIG. 14: AMG 330 relative peak area from SEC after buffer exchange and concentration.

In this experiment, AMG 330 was concentrated up to ~10 mg/mL in the presence of 1 and 2% SBE-β-CD or 2-HP-β-CD. The SBE-β-CD containing formulations are indicated by asterisks. The control on the left (labeled as 0.4 mg/mL) was not concentrated beyond it starting concentration of 0.4 mg/mL. Second from the left (labeled as Control in FIG. 4A and FIG. 4B) is sample that was concentrated without any cyclodextrin. The comparison between SBE-β-CD and 2-HP-β-CD formulations demonstrated the advantage of using SBE-β-CD. FIG. 13 shows the highest concentration reached; FIG. 14 reveals the composition of these concentrated solutions in terms of % aggregate and % monomer.

prepared and stored in Eppendorf tubes (table 14). The tubes were wrapped in plastic and protected from light during incubation. Aliquots were taken after 1 and 4 days incubation at 4° C. and 25° C. (Thermofisher Scientific, (Newington, N.H.) Haake A28). The aliquots were briefly micro centrifuged (Eppendorf Centrifuge 5418, St. Louis, Mo., USA) and the supernatants were analyzed by analytical SEC.

TABLE 14

Solution composition and preparation:

| Solution ID | Solution composition | Solution preparation | Volume |
|---|---|---|---|
| A | 2 mg/mL AMG 330 | N/A | 500 uL |
| B | 20 mM Citrate, pH 6.0 | N/A | |
| C | 10% SBE-β-CD in B | 1.0 g, bring to 10 g in B | |
| D | 10% alpha-cyclodextrin (α-CD) in B | 1.0 g, bring to 10 g in B | 10 mL |
| E | 10% gamma-cyclodextrin (γ-CD) in B | 1.0 g, bring to 10 g in B | 10 mL |
| F | 10% 2-hydroxypropyl-beta-cyclodextrin (2-HP-β-CD) in B | 1.0 g, bring to 10g in B | 10 mL |
| G | 1% PS-80 in B | N/A | |
| H | 2 mg/mL AMG 330 + 0.01% PS-80 | 495 uL A + 5 uL G | 500 uL |

TABLE 15

Sample composition and preparation:

| Sample ID | Sample composition | Sample preparation | Volume | Aliquot Volume | Storage temperature (C.) |
|---|---|---|---|---|---|
| Control at 4° C. | Control | 95 uL H + 5 uL B | 100 uL | 50 uL | 4 C. (Fridge) |
| Control at 25° C. | Control | 95 uL H + 5 uL B | 100 uL | 50 uL | 25 C. (Incubator) |
| 0.5% SBE-β-CD at 4° C. | 0.5% SBE-β-CD | 95 uL H + 5 uL C | 100 uL | 50 uL | 4 C. (Fridge) |
| 0.5% SBE-β-CD at 25° C. | 0.5% SBE-β-CD | 95 uL H + 5 uL C | 100 uL | 50 uL | 25 C. (Incubator) |
| 0.5% α-CD at 4° C. | 0.5% α-CD | 95 uL H + 5 uL D | 100 uL | 50 uL | 4 C. (Fridge) |
| 0.5% α-CD at 25° C. | 0.5% α-CD | 95 uL H + 5 uL D | 100 uL | 50 uL | 25 C. (Incubator) |
| 0.5% γ-CD at 4° C. | 0.5% γ-CD | 95 uL H + 5 uL E | 100 uL | 50 uL | 4 C. (Fridge) |
| 0.5% γ-CD at 25° C. | 0.5% γ-CD | 95 uL H + 5 uL E | 100 uL | 50 uL | 25 C. (Incubator) |
| 0.5% 2-HP-β-CD at 4° C. | 0.5% 2-HP-β-CD | 95 uL H + 5 uL F | 100 uL | 50 uL | 4 C. (Fridge) |
| 0.5% 2-HP-β-CD at 25° C. | 0.5% 2-HP-β-CD | 95 uL H + 5 uL F | 100 uL | 50 uL | 25 C. (Incubator) |

Example 11

Comparing the Effects of Four Different Cyclodextrins for Their Ability to Maintain AMG 330 in a Soluble Non-Aggregated Form SBE-β-CD has been shown to reduce aggregation in AMG 330 in previous experiments. The purpose of this experiment is to evaluate other cyclodextrins in comparison to SBE-β-CD. The levels of aggregation in AMG 330 were measured after 1-4 days incubation at 4° C. and 25° C. with 4 different cyclodextrins.
Materials and Methods:
All samples also contained ~2 mg/mL AMG 330, 20 mM Citrate, and 0.01% Polysorbate-80, pH 6.0. Samples were Four different cyclodextrins, including SBE-β-CD, were tested for ability to maintain AMG 330 in a soluble non-aggregated form. Protein at ~2 mg/ml was incubated for 4 days at 4° and 25° C. without further concentration. All samples also contained 20 mM Citrate and 0.01% Polysorbate-80, pH 6.0.

Figure 15:
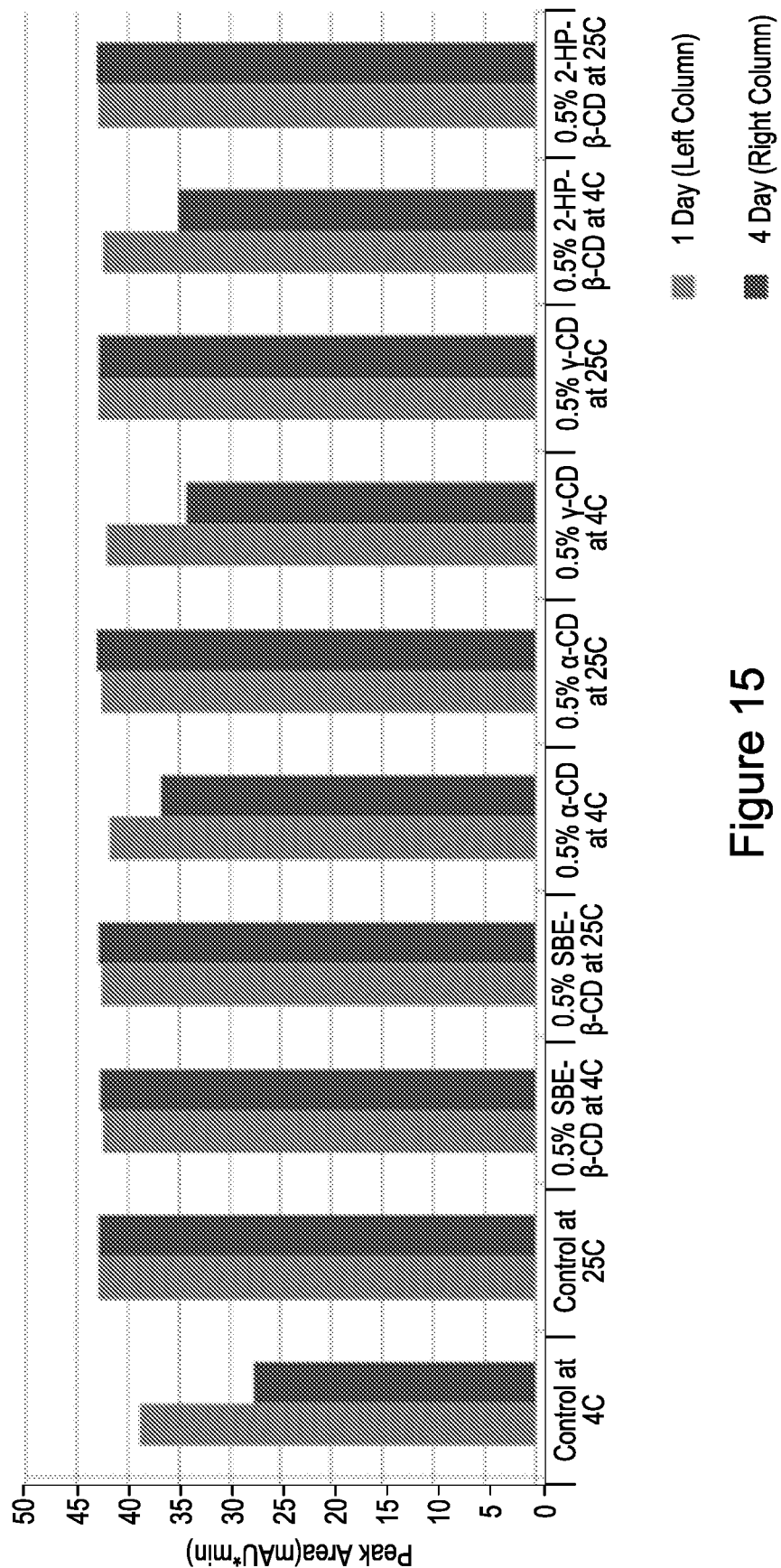
FIG. 15: AMG 330 SEC total peak areas (main peak+HMW) peak after incubation with various cyclodextrins

At end of 4 days at 4° C., 0.5% SBE-β-CD formulation had a larger total peak area by SEC indicating higher soluble protein concentrations. Other formulations precipitated and aggregated to various degrees. This result demonstrate that SBE-β-CD was a more effective stabilizer and solubilizer of AMG 330 at both temperatures (4° and 25° C.) compared to α-cyclodextrin, γ-cyclodextrin or hydroxypropyl β-cyclodextrins seemed to fare better only at 25° C. (FIG. 15).

Example 12

AMG 330 in 13 Different Formulations at 1 mg/mL and Stored at −20, −30 and −70° C. for Up to 6 Weeks The purpose of this experiment is to develop a stable frozen and lyophilized formulation for AMG 330 SBE-β-CD and Triton X-100 was evaluated s formulation excipients. Polycarbonate carboys will be used to simulate drug substance (DS) frozen storage.

Materials and Methods:

With a starting concentration of 0.4 mg/mL for AMG 330, UF/DF buffer exchange (buffers listed in table 16) was carried out using two cogent μScale TFF systems with a delta pressure set at ~23 psi. Four Millipore Pellicon 3 Ultracel 10 kD 0.11 m2 cassettes and two cogent tubing assemblies were used. Post exchange, the material was over-concentrated to 1.2 mg/mL and collected in sterile Nalgene containers.

TABLE 16

Formulation composition:

| Sample ID | Formulation Abbreviation | Formulation composition |
|---|---|---|
| FRM 1 | C60CpGSuP | 10 mM Citrate, 1% SBE-β-CD, 2% Glycine, 1% Sucrose, 0.01% PS80, pH 6.0 |
| FRM 2 | C60CpMSuP | 10 mM Citrate, 1% SBE-β-CD, 4% Mannitol, 2% Sucrose, 0.01% PS80, pH 6.0 |
| FRM 3 | C60CpSuP | 10 mM Citrate, 1% SBE-β-CD, 8% Sucrose, 0.01% PS80, pH 6.0 |
| FRM 4 | H60CpGSuP | 10 mM Histidine, 1% SBE-β-CD, 2% Glycine, 1% Sucrose, 0.01% PS80, pH 6.0 |
| FRM 5 | H60CpMSuP | 10 mM Histidine, 1% SBE-β-CD, 4% Mannitol, 2% Sucrose, 0.01% PS80, pH 6.0 |
| FRM 6 | H60CpSuP | 10 mM Histidine, 1% SBE-β-CD, 8% Sucrose, 0.01% PS80, pH 6.0 |
| FRM 7 | KP60CpGSuP | 10 mM Potassium phosphate, 1% SBE-β-CD, 2% Glycine, 1% Sucrose, 0.01% PS80, pH 6.0 |
| FRM 8 | KP60CpMSuP | 10 mM Potassium phosphate, 1% SBE-β-CD, 4% Mannitol, 2% Sucrose, 0.01% PS80, pH 6.0 |
| FRM 9 | KP60CpSuP | 10 mM Potassium phosphate, 1% SBE-β-CD, 8% Sucrose, 0.01% PS80, pH 6.0 |
| FRM 10 | KP60CpGSuT | 10 mM Potassium phosphate, 1% SBE-β-CD, 2% Glycine, 1% Sucrose, 0.004% Triton X-100, pH 6.0 |
| FRM 11 | KP60CpMSuT | 10 mM Potassium phosphate, 1% SBE-β-CD, 4% Mannitol, 2% Sucrose, 0.004% Triton X-100, pH 6.0 |
| FRM 12 | KP60CpSuT | 10 mM Potassium phosphate, 1% SBE-β-CD, 8% Sucrose, 0.004% Triton X-100, pH 6.0 |
| FRM 13 | PEG 4000 | 35 mM Tris, 17.5 mM Sodium phosphate, 50 mM Arginine, 1.4% Trehalose, 0.05% PEG 4000 at pH 6.0 |

Formulation buffer, PEG and surfactant stocks were freshly prepared and added to produce the final formulated material. Samples were filled out at a volume of 15 mL in 30 mL PC carboys (Nalgene) for this experiment). All samples were filtered in a sterile hood using sterivex filter units (0.22 μm) prior to filling. Final protein concentration in PC carboys is 1 mg/mL.

For static experiments, samples were measured by analytical SEC (same as Example 8) at t=0 and t=6 weeks.

Results:

SBE-β-CD was included in AMG 330 formulations that were incubated at various temperatures. Results after 6 weeks of storage showed that all the SBE-β-CD containing formulations were stable in contrast to a formulation based on the use of PEG-4000 and without SBE-β-CD.

Figure 16:
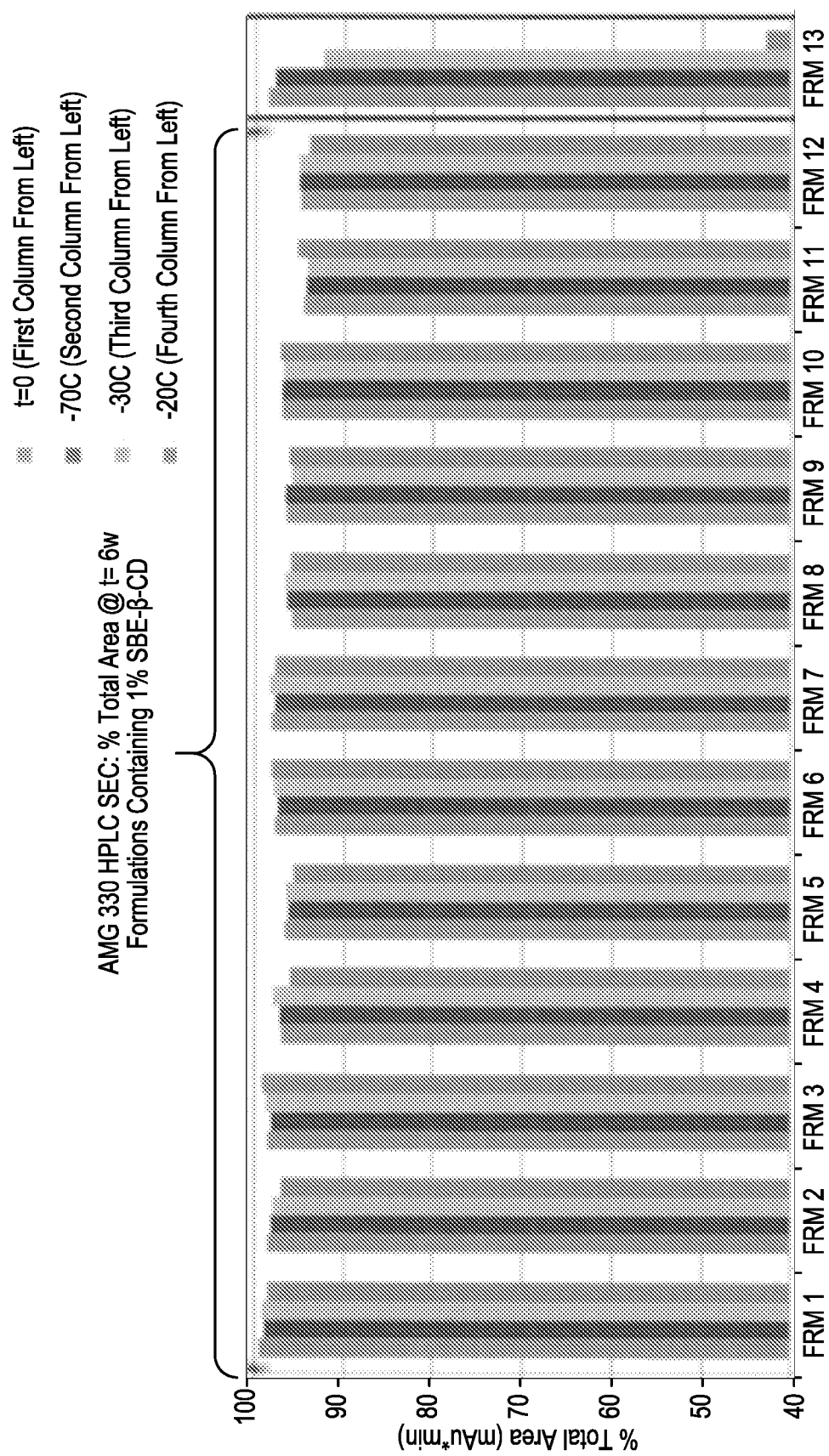
FIG. 16: AMG 330 in 13 different formulations at 1 mg/mL and stored at −20, −30 and −700° C. for up to 6 weeks.

The comparison between SBE-β-CD and PEG based formulation demonstrates the advantage of using SBE-β-CD. PEG based formulation aggregated and particulated heavily after storage at −20° C. (FIG. 16).

Example 13

Evaluation of Two Cyclodextrans (SBE-β-CD and α-cyclodextrin) as Excipients For Lyophilized Formulation For AMG 330

This experiment was conducted to determine a platform lyophilized formulation can be developed for BiTE® molecules. AMG 330 BiTE® was used as a model protein. Two cyclodextrins (SBE-β-CD and α-cyclodextran) was evaluated as formulation excipients.

Materials and Methods:

AMG 330 drug substance concentration is 0.4 mg/mL. AMG 330 was buffer exchanged into respective buffers (listed in table 17) using Millipore Centripreps (30K NMWL, 15 mL):

1. Aliquoted 30 mL of AMG 330 DS into two (2×15 mL) Centriprep sample containers per formulation
2. Added 4.4 mL of corresponding formulation buffer to each Centriprep filtrate collector (to prevent overconcentration of DS)
3. Centrifuged (Allegra 6R Centrifuge, Beckman Coulter, Brea, Calif., USA) at 1500×g for 20 min at 25° C. (centrifuged to equilibrium); ~5 mL of protein remaining in each sample container, 3-fold concentration to 1.2 mg/mL target
4. Decanted filtrate in each filtrate collector and replaced with 4.4 mL of fresh formulation buffer; added 10 mL of fresh formulation buffer to each sample container
5. Centrifuged per step 3
6. Repeated steps 4-5 four more times (five buffer exchanges total; ~243-fold total dilution)
7. Stored buffer-exchanged material O/N at 4° C.

TABLE 17

Formulation components for lyophilization:

| Sample ID | Formulation concentration (mg/mL) | Buffer | Excipient | Surfactant | pH |
|---|---|---|---|---|---|
| C60SuT | 0.85 | 20 mM Citrate | 4% (w/v) Sucrose | 0.01% (w/v) Polysorbate 80 | 6 |
| C60GSuT | 0.85 | 20 mM Citrate | 2% (w/v) Glycine, 1% (w/v) Sucrose | 0.01% (w/v) Polysorbate 80 | 6 |
| C60MSuT | 0.85 | 20 mM Citrate | 4% Mannitol, 2% (w/v) Sucrose | 0.01% (w/v) Polysorbate 80 | 6 |
| C60RSuT | 0.85 | 20 mM Citrate | 75 mM Arginine, 4% (w/v) Sucrose | 0.01% (w/v) Polysorbate 80 | 6 |
| C60CpT | 0.85 | 20 mM Citrate | 0.5% (w/v) SBE-β-CD | 0.01% (w/v) Polysorbate 80 | 6 |
| C60CpSuT | 0.85 | 20 mM Citrate | 0.5% (w/v) SBE-β-CD, 4% (w/v) Sucrose | 0.01% (w/v) Polysorbate 80 | 6 |
| C60CpGSuT | 0.85 | 20 mM Citrate | 0.5% (w/v) SBE-β-CD, 2% (w/v) Glycine, 1% (w/v) Sucrose | 0.01% (w/v) Polysorbate 80 | 6 |
| C60CpMSuT | 0.85 | 20 mM Citrate | 0.5% (w/v) SBE-β-CD, 4% (w/v) Mannitol, 2% (w/v) Sucrose | 0.01% (w/v) Polysorbate 80 | 6 |
| C60AcL | 0.85 | 20 mM Citrate | 0.5% (w/v) α-Cyclodextrin | 0.01% (w/v) Lutrol F68 | 6 |
| C60AcSuL | 0.85 | 20 mM Citrate | 0.5% (w/v) α-Cyclodextrin 4% (w/v) Sucrose | 0.01% (w/v) Lutrol F68 | 6 |
| C60AcGSuL | 0.85 | 20 mM Citrate | 0.5% (w/v) α-Cyclodextrin, 2% (w/v) Glycine, 1% (w/v) Sucrose | 0.01% (w/v) Lutrol F68 | 6 |
| C60AcMSuL | 0.85 | 20 mM Citrate | 0.5% (w/v) α-Cyclodextrin, 4% (w/v) Mannitol, 2% (w/v) Sucrose | 0.01% (w/v) Lutrol F68 | 6 |

Figure 17A:
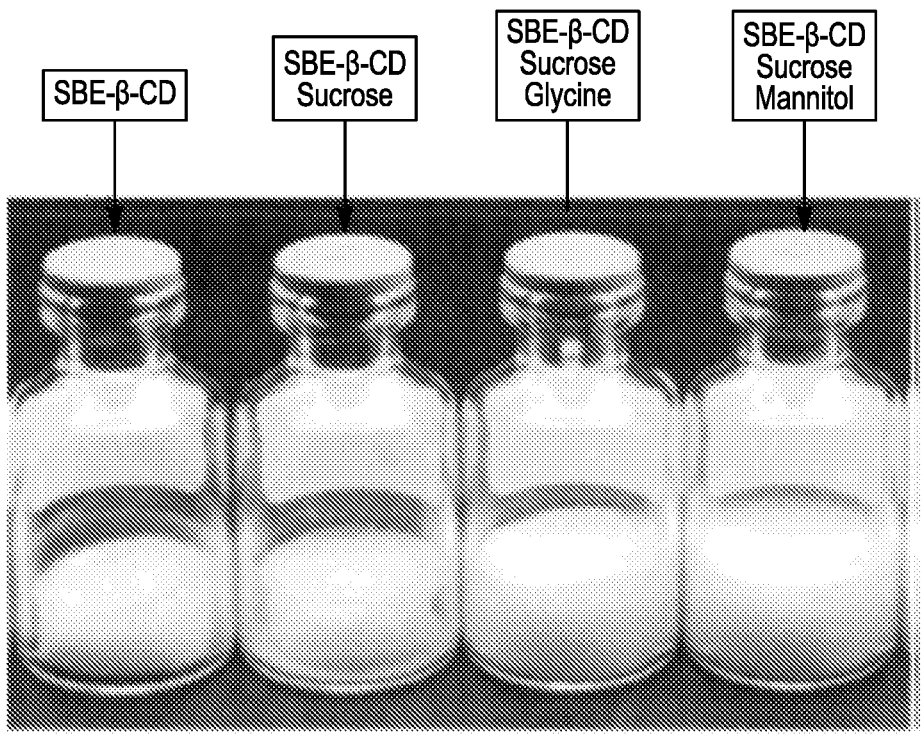
FIGS. 17A-17D.

Formulation buffer and surfactant stocks were added to produce the final formulated material. Samples were filled at a volume of 2 mL in 5 cc glass vials (Schott Type 1A) with a total of 4 vials per formulation. All samples were filtered in a sterile hood using Sterivex filter units (0.22 μm) prior to filling. After filing vials were loosely capped with rubber stoppers for lyophilization (FIG. 17A).

Three vials per formulation were lyophilized using a modified conservative lyophilization cycle (−17° C. annealing temperature, 66 hr total cycle time). The remaining one vial per formulation was reserved for t=0 (pre-lyophilization) analysis. Prior to reconstitution, the lyo cakes were visually inspected for structural integrity and elegance. Lyophilized samples were reconstituted with 1.96 mL of Milli-Q water and gently swirled until fully dissolved for further analysis. Pre-lyophilization and post-constitution samples were analyzed by analytical SEC and micro flow imaging (MFI).

Figure 17B:
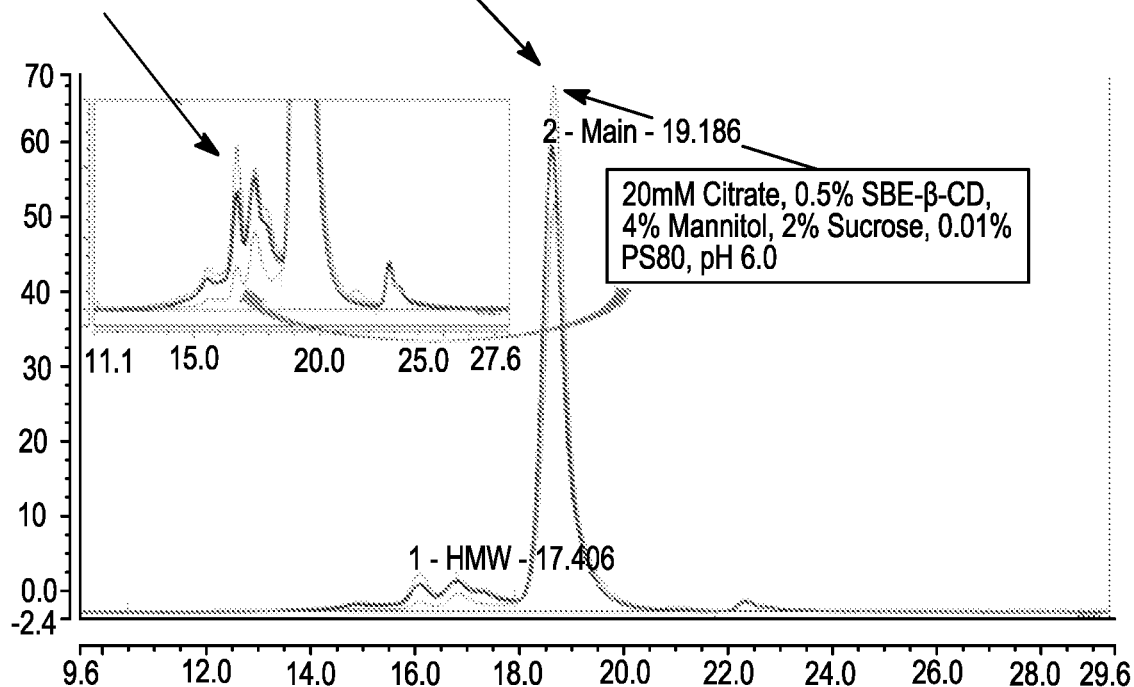
Figure 17C:
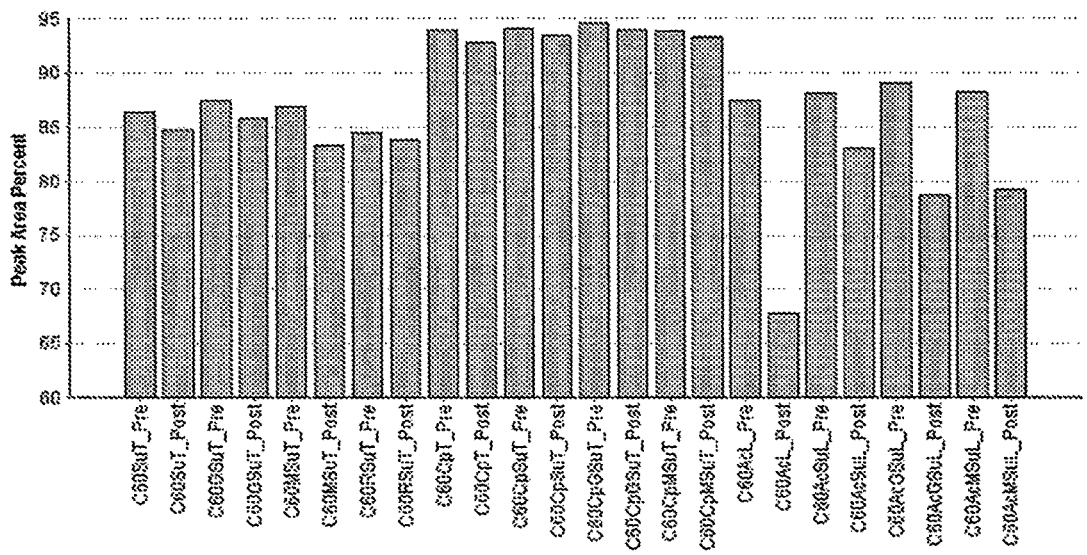

SEC results revealed that SBE-β-CD containing formulations generated lower levels of HMW species pre- and post-lyophilization compared to formulations with α-cyclodextran or no cyclodextran at all. Other formulation excipients (sucrose, glycine, mannitol) did not appear to impact levels of HMW species significantly (FIG. 17B, FIG. 17C).

Figure 17D:
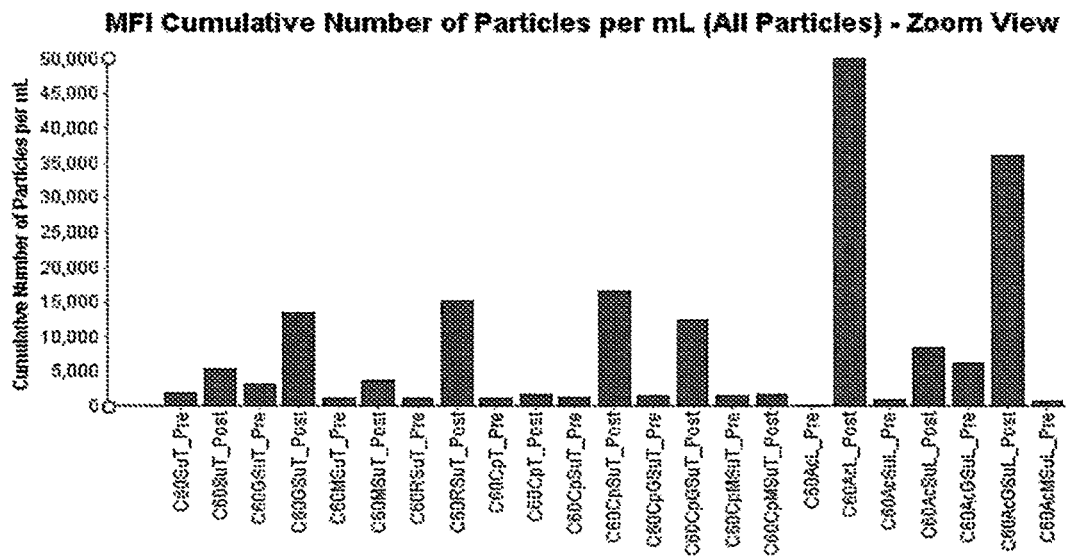

MFI revealed a moderate increase in subvisible particles (majority in the 1-2 μm range) for most formulations following lyophilization. A dramatic increase was observed for one of the α-cyclodextran formulation, C60AcL. Two SBE-β-CD (captisol) containing formulations, C60CpT and C60CpMSuT, contained the least number of subvisible particles after lyophilization (FIG. 17D).

Example 14

Small Scale Formulation Study of Fap Alpha BiTE® Including SBE-β-CD and α-cyclodextran (UFC, LLPS and F/T)

The purpose of this experiment is to evaluate the stability of Fap alpha BiTE® after various stresses in various formulations. Specifically, FAP alpha BiTE® (SEQ ID NO: 177) was evaluated after LLPS, 20 freeze/thaw (F/T) cycles, and concentration by ultrafiltration/centrifugation (UFC). Results from previous studies with similar formulations have shown that SBE-β-CD have a positive effect on AMG 330 BiTE® stability and in this study, effect on SBE-β-CD on FAP BiTE® was investigated.

Materials and Methods:

30 mL of buffer was prepared for each formulation tested.

TABLE 18

Sample composition and preparation. Control (FRM1) is formulated in 10 mM Potassium Phosphate, 161 mM Arginine pH 7.6 + 4% Trehalose at 2.65 mg/mL.

| | | Volume in mL | | | | | | | |
|---|---|---|---|---|---|---|---|---|---|
| Sample ID | Sample composition | 20 mM Citrate | 1% PS-80 | 1% F-68 | 40% SBE-β-CD | 10% α-CD | 15% Glycine | 55% Sucrose | 18% Mannitol |
| FRM1 | Control | N/A | N/A | N/A | N/A | N/A | N/A | N/A | N/A |
| FRM2 | Control, 0.01% PS-80 | 29.7 | 0.3 | | | | | | |
| FRM3 | 0.5% SBE-β-CD, 0.01% | 29.325 | 0.3 | | 0.375 | | | | |

TABLE 18-continued

Sample composition and preparation. Control (FRM1) is formulated in 10 mM Potassium Phosphate, 161 mM Arginine pH 7.6 + 4% Trehalose at 2.65 mg/mL.

Volume in mL

| Sample ID | Sample composition | 20 mM Citrate | 1% PS-80 | 1% F-68 | 40% SBE-β-CD | 10% α-CD | 15% Glycine | 55% Sucrose | 18% Mannitol |
|---|---|---|---|---|---|---|---|---|---|
| FRM4 | PS-80 0.5% SBE-β-CD, 2% Glycine, 1% Sucrose, 0.01% PS-80 | 24.78 | 0.3 |  | 0.375 |  | 4 | 0.545 |  |
| FRM5 | 0.5% SBE-β-CD, 4% Mannitol, 2% Sucrose, 0.01% PS-80 | 21.565 | 0.3 |  | 0.375 |  |  | 1.09 | 6.67 |
| FRM6 | 0.5% α-CD, 0.1% F-68 | 25.5 |  | 3 |  | 1.5 |  |  |  |
| FRM7 | 0.5% α-CD, 2% Glycine, 1% Sucrose, 0.1% F-68 | 20.955 |  | 3 |  | 1.5 | 4 | 0.545 |  |
| FRM8 | 0.5% α-CD, 4% Mannitol, 2% Sucrose, 0.1% F-68 | 17.74 |  | 3 |  | 1.5 |  | 1.09 | 6.67 |

For each sample, 375 μL of 2.65 mg/mL FAP alpha BiTE® (formulated in 10 mM Potassium Phosphate, 161 mM Arginine pH 7.6+4% Trehalose) were placed into an Amicon Ultra 4 mL centrifugal filter tube of MWCO 10,000. 3.5 mL of the appropriate buffer were added to each tube and mixed gently with the protein, and the tubes were centrifuged (Allegra 6R Centrifuge, Beckman Coulter, Brea, Calif., USA) at 4000 rcf at 25 C until retentate volume was ~50 uL. The buffer addition and centrifugation steps were repeated twice more for a total of 3 concentration steps. The retentate was then gently mixed with a pipettor, removed from the filter tube, placed in an Eppendorf tube, and microcentrifuged (Eppendorf Centrifuge 5418, St. Louis, Mo., USA) at maximum speed for 2 min. The supernatant was then analyzed by SEC. Each sample was prepared in duplicate. Non-concentrated FAP alpha BiTE® (2.65 mg/mL) was also analyzed for comparison purposes.

The presence of SBE-β-CD appeared to increase relative SEC mainpeak by suppressing the formation of HMW species during protein concentration. The presence of α-cyclodextran resulted in very low protein recovery and high relative levels of HMW species.

Figure 18:
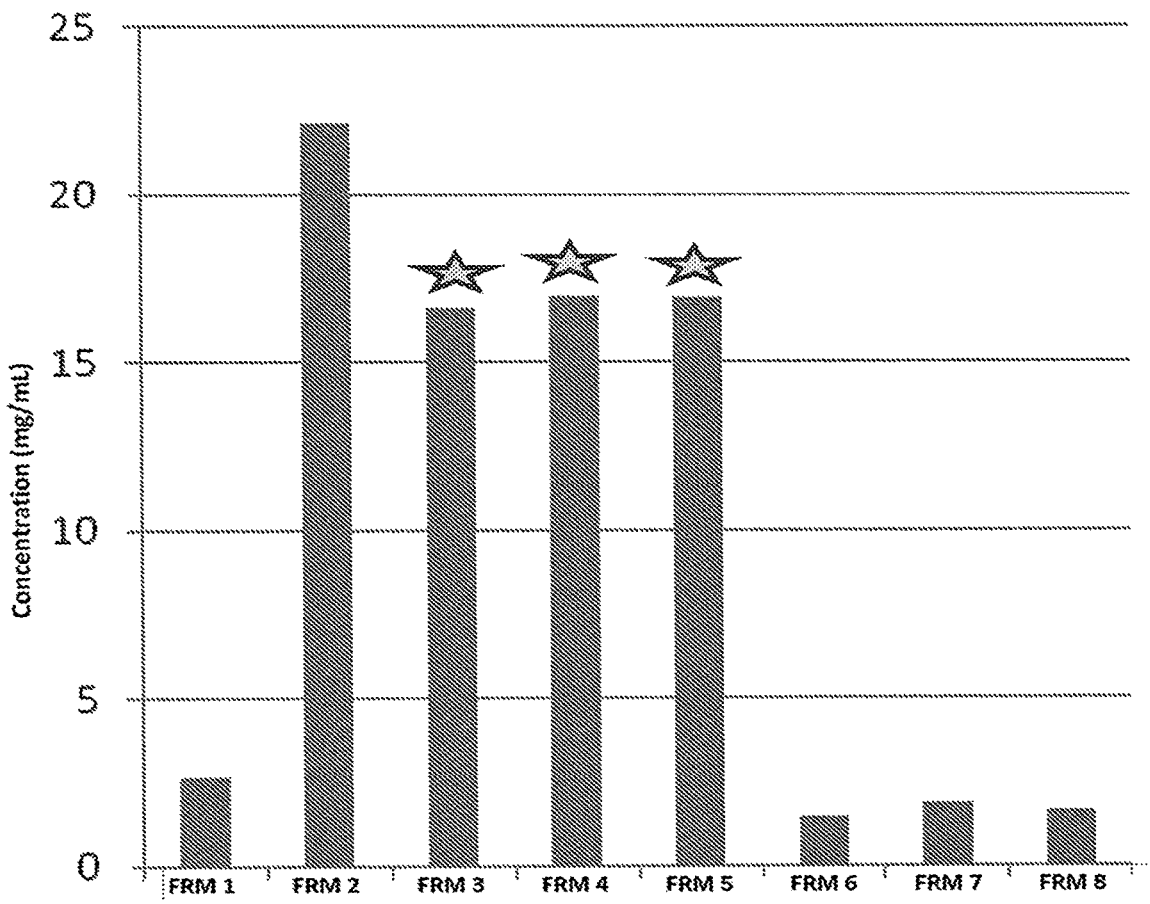
FIG. 18. Summary of maximal Fapα BiTE® (SEQ ID NO: 177) concentrations achieved by overconcentration. SBE-β-CD formulations (indicated by asterisks) reached higher protein concentrations compared to α-cyclodextran and maintained higher % monomer. The α-cyclodextran formulations lost most of their soluble protein because of precipitation.

Fap alpha LLPS results: LLPS results with Fap α BiTE® and SBE-β-CD are comparable to the LLPS results with AMG 330. α-cyclodextran did not show any positive or negative effect on the colloidal stability of this molecule (FIG. 18).

Example 15

Formulation Study for CD33-scFc BiTE Antibody Construct

CD33-scFc BiTE antibody construct was purified using Protein A and cation exchange chromatography (CEX). The CEX eluate was dialyzed into a 10 mM L-glutamic acid buffer at pH 4.2 using dialysis cassettes containing membranes with a molecular weight cut-off (MWCO) of 10 kDa. Dialysis was performed at 2-8° C. The concentration of the dialyzed pool material totaled 2.3 mg/mL. The material was further concentrated via ultrafiltration centrifugation (UFC) using concentrator tubes containing membranes with MWCO of 10 kDa. The concentrated material was filtered with through a filter with a pore size of 0.22 μm. Post filtration concentration totaled 2.7 mg/mL. The material was fully formulated into the formulations listed in Table 19. by spiking with concentrated stock solution. The final protein concentration totals 1.0 mg/mL.

TABLE 19

Overview on tested formulations; HPBCD: hydroxypropyl-beta-cyclodextrin; PS 80: polysorbate 80.

| Designation | L-Glutamic Acid [mM] | Mannitol [% (w/v)] | Sucrose [% (w/v)] | Trehalose dihydrate [% (w/v)] | HPBCD [% (w/v)] | PS 80 [% (w/v)] |
|---|---|---|---|---|---|---|
| G42MSuT | 10 | 4.0 | 2.0 | 0.0 | 0.0 | 0.01 |
| G42MTrT | 10 | 4.0 | 0.0 | 2.0 | 0.0 | 0.01 |

TABLE 19-continued

Overview on tested formulations; HPBCD: hydroxypropyl-beta-cyclodextrin; PS 80: polysorbate 80.

| Designation | L-Glutamic Acid [mM] | Mannitol [% (w/v)] | Sucrose [% (w/v)] | Trehalose dihydrate [% (w/v)] | HPBCD [% (w/v)] | PS 80 [% (w/v)] |
|---|---|---|---|---|---|---|
| G42SuT | 10 | 0.0 | 8.0 | 0.0 | 0.0 | 0.01 |
| G42TrT | 10 | 0.0 | 0.0 | 8.0 | 0.0 | 0.01 |
| G42HP12SuT | 10 | 0.0 | 4.0 | 0.0 | 12.0 | 0.01 |
| G42HP12TrT | 10 | 0.0 | 0.0 | 4.0 | 12.0 | 0.01 |
| G42HP6MT | 10 | 4.0 | 0.0 | 0.0 | 6.0 | 0.01 |
| G42HP6SuT | 10 | 0.0 | 6.0 | 0.0 | 6.0 | 0.01 |
| G42HP6TrT | 10 | 0.0 | 0.0 | 6.0 | 6.0 | 0.01 |

Formulations were filled to 1.0 mL in 2R type I glass vials which were closed with butyl rubber stoppers and aluminum flip off seals. Vials were stored at −20 and −70° C. Samples were pulled at designated time points. After sampling vials were thawed at ambient temperature and analyzed via size exclusion ultra-high performance chromatography (SE-UPLC) in order to quantify the percentaged content of high molecular weight species. SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C. within the autosampler until analysis. A total amount of 3 μg protein was injected. In order to avoid carry over an intermediate injection with 40% ACN was performed after each sample. Detection was based on fluorescence (excitation at 280 nm, emission at 325 nm). Peak integration was performed using Empower® software. Relative area under the curve of HMWS was reported (FIG. 18).

Storage of formulated CD33-scFc BiTE antibody construct at −70° C. or below inhibited the formation of HMWS. However, HMWS significantly increased during storage at −20° C. for formulations that did not contain HPBCD. In contrast, the protein was prevented from forming HMWS at −20° C. in presence of HPBCD irrespective of its concentration (6 or 12%). The presence of mannitol detrimentally affected stability at −20° C. indicated by an increase in HMWS.

Example 16

Formulation Study for FLT3-scFc BiTE Antibody Constructs

Two different FLT3-scFc BiTE antibody constructs (FL1-scFc and FL2-scFc) were purified using protein A and CEX chromatography. Post CEX all constructs were diafiltered in a buffer composed of 10 mM L-glutamic acid, 4% (w/v) sucrose at pH 4.2. The MWCO of the used membrane was 10 kDa. The diafiltered pool (protein concentration of 1.7 mg/mL) was concentrated via ultrafiltration (MWCO of 10 kDa) until a concentration of 7.6 mg/mL was achieved. The material was then filtered through a 0.2 μm filter and fully formulated through spiking with excipient stock solutions. An overview of formulations is provided by Table 20.

TABLE 20

Overview on tested formulations; pH was adjusted to 4.2 for all formulations; HPBCD: hydroxypropyl-beta-cyclodextrin; PS 80: polysorbate 80.

| Designation | Protein [mg/mL] | L-Glutamic acid [mM] | Sucrose [% (w/v)] | HPBCD [% (w/v)] | PS 80 [% (w/v)] |
|---|---|---|---|---|---|
| G42SuT | 5.0 | 10 | 9.0 | 0.0 | 0.01 |
| G42HP12SuT | 5.0 | 10 | 4.0 | 12.0 | 0.01 |

Figure 19:
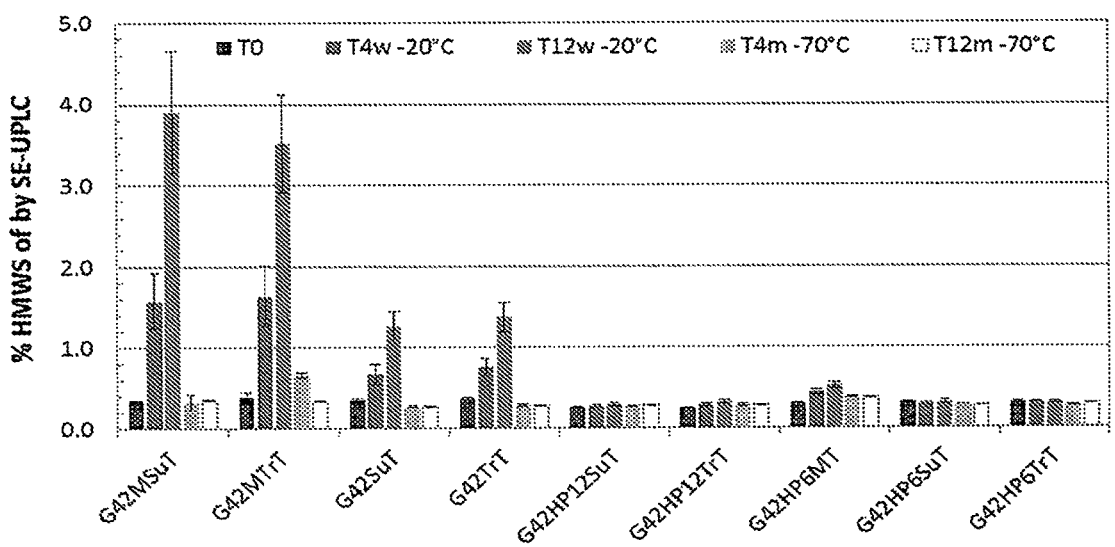
FIG. 19. Overview on percentage content of high molecular weight species (HMWS) determined by size exclusion ultra-high performance chromatography (SE-UPLC) in function of CD33-scFc BiTE antibody construct formulation.

Both formulations were filled to 1.3 mL in 2R type I glass vials which were closed with butyl rubber stoppers and aluminum flip off seals. Vials were stored at −20° C. Samples were pulled at designated time points. After sampling vials were thawed at ambient temperature and analyzed via size exclusion ultra-high performance chromatography (SE-UPLC) in order to quantify the percentaged content of high molecular weight species. SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C. within the autosampler until analysis. A total amount of 3 μg protein was injected. In order to avoid carry over an intermediate injection with 40% ACN was performed after each sample. Detection was based on fluorescence (excitation at 280 nm, emission at 325 nm). Peak integration was performed using Empower® software. Relative area under the curve of HMWS was reported (FIG. 19).

Example 17

Formulation Study for BCMA-scFc BiTE Antibody Constructs

Two BCMA-scFc BiTE antibody constructs (BC1-scFc and BC2-scFc) were purified, formulated, stored, and analyzed as described under Example 16. An overview of formulations is provided by Table 21.

TABLE 21

Overview on tested formulations; pH was adjusted to 4.2 for all formulations; HPBCD: hydroxypropyl-beta-cyclodextrin; PS 80: polysorbate 80.

| Designation | Protein [mg/mL] | L-Glutamic acid [mM] | Sucrose [% (w/v)] | HPBCD [% (w/v)] | PS 80 [% w/v] |
|---|---|---|---|---|---|
| G42SuT | 5.0 | 10 | 9.0 | 0.0 | 0.01 |
| G42HP12SuT | 5.0 | 10 | 6.0 | 6.0 | 0.01 |

Figure 20:
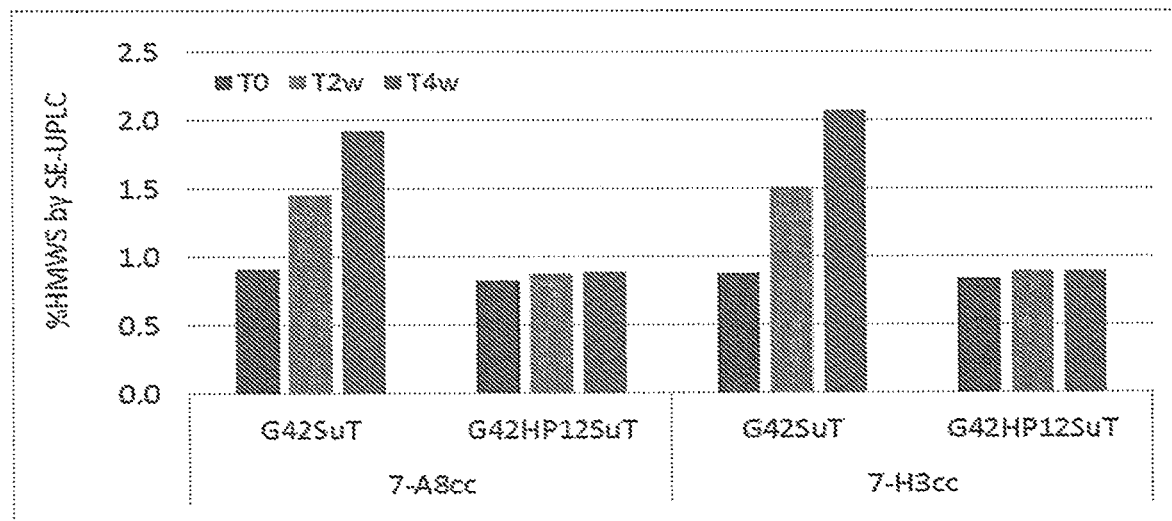
FIG. 20. Overview on percentage content of high molecular weight species (HMWS) determined by size exclusion ultra-high performance chromatography (SE-UPLC) in function of FLT3-scFc BiTE antibody construct formulation.
Figure 21:
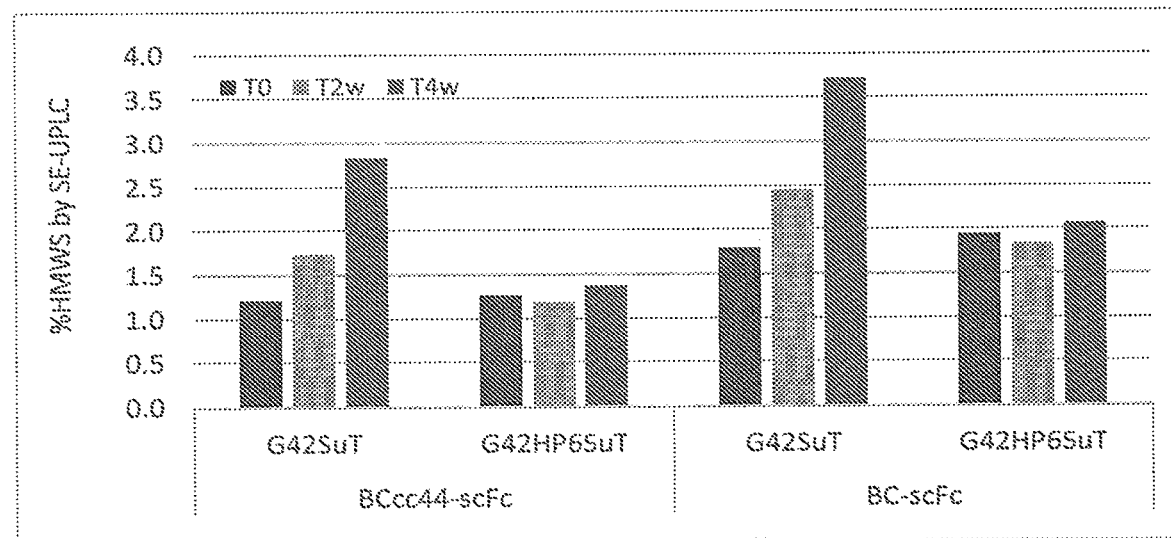
FIG. 21. Overview on percentage content of high molecular weight species (HMWS) determined by size exclusion ultra-high performance chromatography (SE-UPLC) in function of BCMA-scFc BiTE antibody construct formulation.

FIG. 20 shows the percentaged HMWS content in function of formulation for both antibody constructs. The percentaged content of HMWS increased by 1.6% (BC1-scFc) and 1.9% (BC-scFc) respectively in HPBCD free formulations after four weeks. In contrast HMWS formation was inhibited in formulations containing 6% HPBCD.

| SEQ ID NO: | Description | | SEQUENCE |
|---|---|---|---|
| 1. | CD3_1 | VL CDR1 | GSSTGAVTSGYYPN |
| 2. | CD3_1 | VL CDR2 | GTKFLAP |
| 3. | CD3_1 | VL CDR3 | ALWYSNRWV |
| 4. | CD3_1 | VH CDR1 | IYAMN |
| 5. | CD3_1 | VH CDR2 | RIRSKYNNYATYYADSVKS |
| 6. | CD3_1 | VH CDR3 | HGNFGNSYVSFFAY |
| 7. | CD3_1 | VH | EVQLVESGGGLVQPGGSLKLSCAASGFTFNIYAMNWVRQAPGKGLEWVARIRSKYNNYATYYADSVKSRFTISRDDS KNTAYLQMNNLKTEDTAVYYCVRHGNFGNSYVSFFAYWGQGTLVTVSS |
| 8. | CD3_1 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 9. | CD3_1 | scFv | EVQLVESGGGLVQPGGSLKLSCAASGFTFNIYAMNWVRQAPGKGLEWVARIRSKYNNYATYYADSVKSRFTISRDDS KNTAYLQMNNLKTEDTAVYYCVRHGNFGNSYVSFFAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 10. | CD3_2 | VL CDR1 | GSSTGAVTSGYYPN |
| 11. | CD3_2 | VL CDR2 | GTKFLAP |
| 12. | CD3_2 | VL CDR3 | ALWYSNRWV |
| 13. | CD3_2 | VH CDR1 | KYAMN |
| 14. | CD3_2 | VH CDR2 | RIRSKYNNYATYYADSVKD |
| 15. | CD3_2 | VH CDR3 | HGNFGNSYISYWAY |
| 16. | CD3_2 | VH | EVQLVESGGGLVQPGGSLKLSCAASGFTFNKYAMNWVRQAPGKGLEWVARIRSKYNNYATYYADSVKDRFTISRDDS KNTAYLQMNNLKTEDTAVYYCVRHGNFGNSYISYWAYWGQGTLVTVSS |
| 17. | CD3_2 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 18. | CD3_2 | scFv | EVQLVESGGGLVQPGGSLKLSCAASGFTFNKYAMNWVRQAPGKGLEWVARIRSKYNNYATYYADSVKDRFTISRDDS KNTAYLQMNNLKTEDTAVYYCVRHGNFGNSYISYWAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 19. | CD3_3 | VL CDR1 | GSSTGAVTSGYYPN |
| 20. | CD3_3 | VL CDR2 | GTKFLAP |
| 21. | CD3_3 | VL CDR3 | ALWYSNRWV |
| 22. | CD3_3 | VH CDR1 | SYAMN |

| SEQ ID NO: | Description | | SEQUENCE |
|---|---|---|---|
| 23. | CD3_3 | VH CDR2 | RIRSKYNNYATYYADSVKG |
| 24. | CD3_3 | VH CDR3 | HGNFGNSYLSFWAY |
| 25. | CD3_3 | VH | EVQLVESGGGLEQPGGSLKLSCAASGFTFNSYAMNWVRQAPGKGLEWVARIRSKYNNYATYYADSVKGRFTISRDDS KNTAYLQMNNLKTEDTAVYYCVRHGNFGNSYLSFWAYWGQGTLVTVSS |
| 26. | CD3_3 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 27. | CD3_3 | scFv | EVQLVESGGGLEQPGGSLKLSCAASGFTFNSYAMNWVRQAPGKGLEWVARIRSKYNNYATYYADSVKGRFTISRDDS KNTAYLQMNNLKTEDTAVYYCVRHGNFGNSYLSFWAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 28. | CD3_4 | VL CDR1 | GSSTGAVTSGYYPN |
| 29. | CD3_4 | VL CDR2 | GTKFLAP |
| 30. | CD3_4 | VL CDR3 | ALWYSNRWV |
| 31. | CD3_4 | VH CDR1 | RYAMN |
| 32. | CD3_4 | VH CDR2 | RIRSKYNNYATYYADSVKG |
| 33. | CD3_4 | VH CDR3 | HGNFGNSYLSYFAY |
| 34. | CD3_4 | VH | EVQLVESGGGLVQPGGSLKLSCAASGFTFNRYAMNWVRQAPGKGLEWVARIRSKYNNYATYYADSVKGRFTISRDDS KNTAYLQMNNLKTEDTAVYYCVRHGNFGNSYLSYFAYWGQGTLVTVSS |
| 35. | CD3_4 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 36. | CD3_4 | scFv | EVQLVESGGGLVQPGGSLKLSCAASGFTFNRYAMNWVRQAPGKGLEWVARIRSKYNNYATYYADSVKGRFTISRDDS KNTAYLQMNNLKTEDTAVYYCVRHGNFGNSYLSYFAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 37. | CD3_5 | VL CDR1 | RSSTGAVTSGYYPN |
| 38. | CD3_5 | VL CDR2 | ATDMRPS |
| 39. | CD3_5 | VL CDR3 | ALWYSNRWV |
| 40. | CD3_5 | VH CDR1 | VYAMN |
| 41. | CD3_5 | VH CDR2 | RIRSKYNNYATYYADSVKK |
| 42. | CD3_5 | VH CDR3 | HGNFGNSYLSWWAY |
| 43. | CD3_5 | VH | EVQLVESGGGLVQPGGSLKLSCAASGFTFNVYAMNWVRQAPGKGLEWVARIRSKYNNYATYYADSVKKRFTISRDDS KNTAYLQMNNLKTEDTAVYYCVRHGNFGNSYLSWWAYWGQGTLVTVSS |
| 44. | CD3_5 | VL | QTVVTQEPSLTVSPGGTVTLTCRSSTGAVTSGYYPNWVQQKPGQAPRGLIGATDMRPSGTPARFSGSLLGGKAALTL SGVQPEDEAEYYCALWYSNRWVFGGGTKLTVL |
| 45. | CD3_5 | scFv | EVQLVESGGGLVQPGGSLKLSCAASGFTFNVYAMNWVRQAPGKGLEWVARIRSKYNNYATYYADSVKKRFTISRDDS KNTAYLQMNNLKTEDTAVYYCVRHGNFGNSYLSWWAYWGQGTLVTVSSGGGGSGGGGSGGGGSQTVVTQEPSLTVSP GGTVTLTCRSSTGAVTSGYYPNWVQQKPGQAPRGLIGATDMRPSGTPARFSGSLLGGKAALTLSGVQPEDEAEYYCA LWYSNRWVFGGGTKLTVL |
| 46. | CD3_6 | VL CDR1 | GSSTGAVTSGYYPN |
| 47. | CD3_6 | VL CDR2 | GTKFLAP |
| 48. | CD3_6 | VL CDR3 | ALWYSNRWV |
| 49. | CD3_6 | VH CDR1 | KYAMN |
| 50. | CD3_6 | VH CDR2 | RIRSKYNNYATYYADSVKS |
| 51. | CD3_6 | VH CDR3 | HGNFGNSYTSYYAY |
| 52. | CD3_6 | VH | EVQLVESGGGLVQPGGSLKLSCAASGFTFNKYAMNWVRQAPGKGLEWVARIRSKYNNYATYYADSVKSRFTISRDDS KNTAYLQMNNLKTEDTAVYYCVRHGNFGNSYTSYYAYWGQGTLVTVSS |

-continued

| SEQ ID NO: | Description | | SEQUENCE |
|---|---|---|---|
| 53. | CD3_6 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 54. | CD3_6 | scFv | EVQLVESGGGLVQPGGSLKLSCAASGFTFNKYAMNWVRQAPGKGLEWVARIRSKYNNYATYYADSVKSRFTISRDDS KNTAYLQMNNLKTEDTAVYYCVRHGNFGNSYTSYYAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 55. | CD3_7 | VL CDR1 | RSSTGAVTSGYYPN |
| 56. | CD3_7 | VL CDR2 | ATDMRPS |
| 57. | CD3_7 | VL CDR3 | ALWYSNRWV |
| 58. | CD3_7 | VH CDR1 | GYAMN |
| 59. | CD3_7 | VH CDR2 | RIRSKYNNYATYYADSVKE |
| 60. | CD3_7 | VH CDR3 | HRNFGNSYLSWFAY |
| 61. | CD3_7 | VH | EVQLVESGGGLVQPGGSLKLSCAASGFTFNGYAMNWVRQAPGKGLEWVARIRSKYNNYATYYADSVKERFTISRDDS KNTAYLQMNNLKTEDTAVYYCVRHRNFGNSYLSWFAYWGQGTLVTVSS |
| 62. | CD3_7 | VL | QTVVTQEPSLTVSPGGTVTLTCRSSTGAVTSGYYPNWVQQKPGQAPRGLIGATDMRPSGTPARFSGSLLGGKAALTL SGVQPEDEAEYYCALWYSNRWVFGGGTKLTVL |
| 63. | CD3_7 | scFv | EVQLVESGGGLVQPGGSLKLSCAASGFTFNGYAMNWVRQAPGKGLEWVARIRSKYNNYATYYADSVKERFTISRDDS KNTAYLQMNNLKTEDTAVYYCVRHRNFGNSYLSWFAYWGQGTLVTVSSGGGGSGGGGSGGGGSQTVVTQEPSLTVSP GGTVTLTCRSSTGAVTSGYYPNWVQQKPGQAPRGLIGATDMRPSGTPARFSGSLLGGKAALTLSGVQPEDEAEYYCA LWYSNRWVFGGGTKLTVL |
| 64. | CD3_8 | VL CDR1 | GSSTGAVTSGYYPN |
| 65. | CD3_8 | VL CDR2 | GTKFLAP |
| 66. | CD3_8 | VL CDR3 | ALWYSNRWV |
| 67. | CD3_8 | VH CDR1 | VYAMN |
| 68. | CD3_8 | VH CDR2 | RIRSKYNNYATYYADSVKK |
| 69. | CD3_8 | VH CDR3 | HGNFGNSYISWWAY |
| 70. | CD3_8 | VH | EVQLVESGGGLVQPGGSLKLSCAASGFTFNVYAMNWVRQAPGKGLEWVARIRSKYNNYATYYADSVKKRFTISRDDS KNTAYLQMNNLKTEDTAVYYCVRHGNFGNSYISWWAYWGQGTLVTVSS |
| 71. | CD3_8 | VL | QTVVTQEPSLTVSPGGTVTLTCGSSTGAVTSGYYPNWVQQKPGQAPRGLIGGTKFLAPGTPARFSGSLLGGKAALTL SGVQPEDEAEYYCALWYSNRWVFGGGTKLTVL |
| 72. | CD3_8 | scFv | EVQLVESGGGLVQPGGSLKLSCAASGFTFNVYAMNWVRQAPGKGLEWVARIRSKYNNYATYYADSVKKRFTISRDDS KNTAYLQMNNLKTEDTAVYYCVRHGNFGNSYISWWAYWGQGTLVTVSSGGGGSGGGGSGGGGSQTVVTQEPSLTVSP GGTVTLTCGSSTGAVTSGYYPNWVQQKPGQAPRGLIGGTKFLAPGTPARFSGSLLGGKAALTLSGVQPEDEAEYYCA LWYSNRWVFGGGTKLTVL |
| 73. | CD3_9 | VL CDR1 | GSSTGAVTSGNYPN |
| 74. | CD3_9 | VL CDR2 | GTKFLAP |
| 75. | CD3_9 | VL CDR3 | VLWYSNRWV |
| 76. | CD3_9 | VH CDR1 | SYAMN |
| 77. | CD3_9 | VH CDR2 | RIRSKYNNYATYYADSVKG |
| 78. | CD3_9 | VH CDR3 | HGNFGNSYVSWWAY |
| 79. | CD3_9 | VH | EVQLVESGGGLVQPGGSLKLSCAASGFTFNSYAMNWVRQAPGKGLEWVARIRSKYNNYATYYADSVKGRFTISRDDS KNTAYLQMNNLKTEDTAVYYCVRHGNFGNSYVSWWAYWGQGTLVTVSS |
| 80. | CD3_9 | VL | QTVVTQEPSLTVSPGGTVTLTCGSSTGAVTSGNYPNWVQQKPGQAPRGLIGGTKFLAPGTPARFSGSLLGGKAALTL SGVQPEDEAEYYCVLWYSNRWVFGGGTKLTVL |

-continued

| SEQ ID NO: | Description | | SEQUENCE |
|---|---|---|---|
| 81. | CD3_9 | scFv | EVQLVESGGGLVQPGGSLKLSCAASGFTFNSYAMNWVRQAPGKGLEWVARIRSKYNNYATYYADSVKGRFTISRDDS KNTAYLQMNNLKTEDTAVYYCVRHGNFGNSYVSWWAYWGQGTLVTVSSGGGGSGGGGSGGGGSQTVVTQEPSLTVSP GGTVTLTCGSSTGAVTSGNYPNWVQQKPGQAPRGLIGGTKFLAPGTPARFSGSLLGGKAALTLSGVQPEDEAEYYCV LWYSNRWVFGGGTKLTVL |
| 82. | CD3_10 | VL CDR1 | GSSTGAVTSGNYPN |
| 83. | CD3_10 | VL CDR2 | GTKFLAP |
| 84. | CD3_10 | VL CDR3 | VLWYSNRWV |
| 85. | CD3_10 | VH CDR1 | KYAMN |
| 86. | CD3_10 | VH CDR2 | RIRSKYNNYATYYADSVKD |
| 87. | CD3_10 | VH CDR3 | HGNFGNSYISYWAY |
| 88. | CD3_10 | VH | EVQLVESGGGLVQPGGSLKLSCAASGFTFNKYAMNWVRQAPGKGLEWVARIRSKYNNYATYYADSVKDRFTISRDDS KNTAYLQMNNLKTEDTAVYYCVRHGNFGNSYISYWAYWGQGTLVTVSS |
| 89. | CD3_10 | VL | QTVVTQEPSLTVSPGGTVTLTCGSSTGAVTSGNYPNWVQQKPGQAPRGLIGGTKFLAPGTPARFSGSLLGGKAALTL SGVQPEDEAEYYCVLWYSNRWVFGGGTKLTVL |
| 90. | CD3_10 | scFv | EVQLVESGGGLVQPGGSLKLSCAASGFTFNKYAMNWVRQAPGKGLEWVARIRSKYNNYATYYADSVKDRFTISRDDS KNTAYLQMNNLKTEDTAVYYCVRHGNFGNSYISYWAYWGQGTLVTVSSGGGGSGGGGSGGGGSQTVVTQEPSLTVSP GGTVTLTCGSSTGAVTSGNYPNWVQQKPGQAPRGLIGGTKFLAPGTPARFSGSLLGGKAALTLSGVQPEDEAEYYCV LWYSNRWVFGGGTKLTVL |
| 91. | CD33_1 | VH CDR1 | NYGMN |
| 92. | CD33_1 | VH CDR2 | WINTYTGEPTYADKFQG |
| 93. | CD33_1 | VH CDR3 | WSWSDGYYVYFDY |
| 94. | CD33_1 | VL CDR1 | KSSQSVLDSSTNKNSLA |
| 95. | CD33_1 | VL CDR2 | WASTRES |
| 96. | CD33_1 | VL CDR3 | QQSAHFPIT |
| 97. | CD33_1 | VH | QVQLVQSGAEVKKPGESVKVSCKASGYTFTNYGMNWVKQAPGQGLEWMGWINTYTGEPTYADKFQGRVTMTTDTSTS TAYMEIRNLGGDDTAVYYCARWSWSDGYYVYFDYWGQGTSVTVSS |
| 98. | CD33_1 | VL | DIVMTQSPDSLTVSLGERTTINCKSSQSVLDSSTNKNSLAWYQQKPGQPPKLLLSWASTRESGIPDRFSGSGSGTDF TLTIDSPQPEDSATYYCQQSAHFPITFGQGTRLEIK |
| 99. | CD33_1 | scFv | QVQLVQSGAEVKKPGESVKVSCKASGYTFTNYGMNWVKQAPGQGLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSPQPEDSATYYC QQSAHFPITFGQGTRLEIK |
| 100. | CD33_1 | bispecific molecule | QVQLVQSGAEVKKPGESVKVSCKASGYTFTNYGMNWVKQAPGQGLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSPQPEDSATYYC QQSAHFPITFGQGTRLEIKSGGGGSEVQLVESGGGLVQPGGSLKLSCAASGFTFNKYAMNWVRQAPGKGLEWVARIR SKYNNYATYYADSVKDRFTISRDDSKNTAYLQMNNLKTEDTAVYYCVRHGNFGNSYISYWAYWGQGTLVTVSSGGGG SGGGGSGGGGSQTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 101. | CD33_2 | VH CDR1 | NYGMN |
| 102. | CD33_2 | VH CDR2 | WINTYTGEPTYADKFQG |
| 103. | CD33_2 | VH CDR3 | WSWSDGYYVYFDY |
| 104. | CD33_2 | VL CDR1 | KSSQSVLDSSTNKNSLA |
| 105. | CD33_2 | VL CDR2 | WASTRES |
| 106. | cD33_2 | VL CDR3 | QQSAHFPIT |
| 107. | CD33_2 | VH | QVQLVQSGAEVKKPGESVKVSCKASGYTFTNYGMNWVKQAPGQCLEWMGWINTYTGEPTYADKFQGRVTMTTDTSTS TAYMEIRNLGGDDTAVYYCARWSWSDGYYVYFDYWGQGTSVTVSS |

| SEQ ID NO: | Description | | SEQUENCE |
|---|---|---|---|
| 108. | CD33_2 | VL | DIVMTQSPDSLTVSLGERTTINCKSSQSVLDSSTNKNSLAWYQQKPGQPPKLLLSWASTRESGIPDRFSGSGSGTDF TLTIDSPQPEDSATYYCQQSAHFPITFGCGTRLEIK |
| 109. | CD33_2 | scFv | QVQLVQSGAEVKKPGESVKVSCKASGYTFTNYGMNWVKQAPGQCLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSPQPEDSATYYC QQSAHFPITFGCGTRLEIK |
| 110. | CD33_2 | bi-specific molecule | QVQLVQSGAEVKKPGESVKVSCKASGYTFTNYGMNWVKQAPGQCLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSPQPEDSATYYC QQSAHFPITFGCGTRLEIKSGGGGSEVQLVESGGGLVQPGGSLKLSCAASGFTFNKYAMNWVRQAPGKGLEWVARIR SKYNNYATYYADSVKDRFTISRDDSKNTAYLQMNNLKTEDTAVYYCVRHGNFGNSYISYWAYWGQGTLVTVSSGGGG SGGGGSGGGGSQTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVL |
| 111. | CD33_3 | VH CDR1 | NYGMN |
| 112. | CD33_3 | VH CDR2 | WINTYTGEPTYADDFKG |
| 113. | CD33_3 | VH CDR3 | WSWSDGYYVYFDY |
| 114. | CD33_3 | VL CDR1 | KSSQSVLDSSKNKNSLA |
| 115. | CD33_3 | VL CDR2 | WASTRES |
| 116. | CD33_3 | VL CDR3 | QQSAHFPIT |
| 117. | CD33_3 | VH | QVQLVQSGAEVKKPGESVKVSCKASGYTFTNYGMNWVRQAPGQGLEWMGWINTYTGEPTYADDFKGRVTM SSDTSTSTAYLEINSLRSDDTAIYYCARWSWSDGYYVYFDYWGQGTTVTVSS |
| 118. | CD33_3 | VL | DIVMTQSPDSLTVSLGERTTINCKSSQSVLDSSKNKNSLAWYQQKPGQPPKLLLSWASTRESGIPDRFSG SGSGTDFTLTIDSLQPEDSATYYCQQSAHFPITFGQGTRLEIK |
| 119. | CD33_3 | scFv | QVQLVQSGAEVKKPGESVKVSCKASGYTFTNYGMNWVRQAPGQGLEWMGWINTYTGEPTYADDFKGRVTM SSDTSTSTAYLEINSLRSDDTAIYYCARWSWSDGYYVYFDYWGQGTTVTVSSGGGGSGGGGSGGGGSDIV MTQSPDSLTVSLGERTTINCKSSQSVLDSSKNKNSLAWYQQKPGQPPKLLLSWASTRESGIPDRFSGSGS GTDFTLTIDSLQPEDSATYYCQQSAHFPITFGQGTRLEIK |
| 120. | CD33_4 | VH CDR1 | NYGMN |
| 121. | CD33_4 | VH CDR2 | WINTYTGEPTYADDFKG |
| 122. | CD33_4 | VH CDR3 | WSWSDGYYVYFDY |
| 123. | CD33_4 | VL CDR1 | QVQLVQSGAEVKKPGASVKVSCKASGYTFTNYGMNWVKQAPGQGLKWMGWINTYTGEPTYADDFKGRVTM TSDTSTSTAYLELHNLRSDDTAVYYCARWSWSDGYYVYFDYWGQGTTVTVSS |
| 124. | CD33_4 | VL CDR2 | KSSQSVLDSSKNKNSLA |
| 125. | CD33_4 | VL CDR3 | WASTRES |
| 126. | CD33_4 | VH | QQSAHFPIT |
| 127. | CD33_4 | VL | DIVMTQSPDSLTVSLGERTTINCKSSQSVLDSSKNKNSLAWYQQKPGQPPKLLLSWASTRESGIPDRFSG SGSGTDFTLTIDSLQPEDSATYYCQQSAHFPITFGQGTRLEIK |
| 128. | CD33_4 | scFv | QVQLVQSGAEVKKPGASVKVSCKASGYTFTNYGMNWVKQAPGQGLKWMGWINTYTGEPTYADDFKGRVTM TSDTSTSTAYLELHNLRSDDTAVYYCARWSWSDGYYVYFDYWGQGTTVTVSSGGGGSGGGGSGGGGSDIV MTQSPDSLTVSLGERTTINCKSSQSVLDSSKNKNSLAWYQQKPGQPPKLLLSWASTRESGIPDRFSGSGS GTDFTLTIDSLQPEDSATYYCQQSAHFPITFGQGTRLEIK |
| 129. | CD33_5 | VH CDR1 | NYGMN |
| 130. | CD33_5 | VH CDR2 | WINTYTGEPTYADDFKG |
| 131. | CD33_5 | VH CDR3 | WSWSDGYYVYFDY |
| 132. | CD33_5 | VL CDR1 | KSSQSVLDSSKNKNSLA |
| 133. | CD33_5 | VL CDR2 | WASTRES |
| 134. | CD33_5 | VL CDR3 | QQSAHFPIT |

| SEQ ID NO: | Description | | SEQUENCE |
|---|---|---|---|
| 135. | CD33_5 | VH | QVQLVQSGAEVKKPGESVKVSCKASGYTFTNYGMNWVKQAPGQGLKWMGWINTYTGEPTYADDFKGRVTM<br>TTDTSTSTAYMEIRNLRNDDTAVYYCARWSWSDGYYVYFDYWGQGTTVTVSS |
| 136. | CD33_5 | VL | DIVMTQSPDSLTVSLGERTTINCKSSQSVLDSSKNKNSLAWYQQKPGQPPKLLLSWASTRESGIPDRFSG<br>SGSGTDFTLTIDSLQPEDSATYYCQQSAHFPITFGQGTRLEIK |
| 137. | CD33_5 | scFv | QVQLVQSGAEVKKPGESVKVSCKASGYTFTNYGMNWVKQAPGQGLKWMGWINTYTGEPTYADDFKGRVTM<br>TTDTSTSTAYMEIRNLRNDDTAVYYCARWSWSDGYYVYFDYWGQGTTVTVSSGGGGSGGGGSGGGGSDIV<br>MTQSPDSLTVSLGERTTINCKSSQSVLDSSKNKNSLAWYQQKPGQPPKLLLSWASTRESGIPDRFSGSGS<br>GTDFTLTIDSLQPEDSATYYCQQSAHFPITFGQGTRLEIK |
| 138. | CD33_6 | VH CDR1 | NYGMN |
| 139. | CD33_6 | VH CDR2 | WINTYTGEPTYADDFKG |
| 140. | CD33_6 | VH CDR3 | WSWSDGYYVYFDY |
| 141. | CD33_6 | VL CDR1 | KSSQSVLDSSKNKNSLA |
| 142. | CD33_6 | VL CDR2 | WASTRES |
| 143. | CD33_6 | VL CDR3 | QQSAHFPIT |
| 144. | CD33_6 | VH | QVQLVQSGAEVKKPGESVKVSCKASGYTFTNYGMNWVKQAPGQGLKWMGWINTYTGEPTYADDFKGRVTM<br>TSDTSTSTAYMEISSLRSDDTAVYYCARWSWSDGYYVYFDYWGQGTTVTVSS |
| 145. | CD33_6 | VL | DIVMTQSPDSLTVSLGERTTINCKSSQSVLDSSKNKNSLAWYQQKPGQPPKLLLSWASTRESGIPDRFSG<br>SGSGTDFTLTIDSLQPEDSATYYCQQSAHFPITFGQGTRLEIK |
| 146. | CD33_6 | scFv | QVQLVQSGAEVKKPGESVKVSCKASGYTFTNYGMNWVKQAPGQGLKWMGWINTYTGEPTYADDFKGRVTM<br>TSDTSTSTAYMEISSLRSDDTAVYYCARWSWSDGYYVYFDYWGQGTTVTVSSGGGGSGGGGSGGGGSDIV<br>MTQSPDSLTVSLGERTTINCKSSQSVLDSSKNKNSLAWYQQKPGQPPKLLLSWASTRESGIPDRFSGSGS<br>GTDFTLTIDSLQPEDSATYYCQQSAHFPITFGQGTRLEIK |
| 147. | CD33_7 | VH CDR1 | NYGMN |
| 148. | CD33_7 | VH CDR2 | WINTYTGETNYADKFQG |
| 149. | CD33_7 | VH CDR3 | WSWSDGYYVYFDY |
| 150. | CD33_7 | VL CDR1 | KSSQSVLDSSTNKNSLA |
| 151. | CD33_7 | VL CDR2 | WASTRE |
| 152. | CD33_7 | VL CDR3 | QQSAHFPIT |
| 153. | CD33_7 | VH | QVQLVQSGAEVKKPGESVKVSCKASGYTFTNYGMNWVKQAPGQGLEWMGWINTYTGETNYADKFQGRVTF<br>TSDTSTSTAYMELRNLKSDDTAVYYCARWSWSDGYYVYFDYWGQGTTVTVSS |
| 154. | CD33_7 | VL | DIVMTQSPDSMTVSLGERTTINCKSSQSVLDSSTNKNSLAWYQQKPGQPPKLLLSWASTRESGIPDRFSG<br>SGSGTDFTLTIDSLQPEDSATYYCQQSAHFPITFGQGTRLDIK |
| 155. | CD33_7 | scFv | QVQLVQSGAEVKKPGESVKVSCKASGYTFTNYGMNWVKQAPGQGLEWMGWINTYTGETNYADKFQGRVTF<br>TSDTSTSTAYMELRNLKSDDTAVYYCARWSWSDGYYVYFDYWGQGTTVTVSSGGGGSGGGGSGGGGSDIV<br>MTQSPDSMTVSLGERTTINCKSSQSVLDSSTNKNSLAWYQQKPGQPPKLLLSWASTRESGIPDRFSGSGS<br>GTDFTLTIDSLQPEDSATYYCQQSAHFPITFGQGTRLDIK |
| 156. | CD33_8 | VH CDR1 | NYGMN |
| 157. | CD33_8 | VH CDR2 | WINTYTGETNYADKFQG |
| 158. | CD33_8 | VH CDR3 | WSWSDGYYVYFDY |
| 159. | CD33_8 | VL CDR1 | KSSQSVLDSSTNKNSLA |
| 160. | CD33_8 | VL CDR2 | WASTRES |
| 161. | CD33_8 | VL CDR3 | QQSAHFPIT |
| 162. | CD33_8 | VH | QVQLVQSGAEVKKPGESVKVSCKASGYTFTNYGMNWVKQAPGQGLEWMGWINTYTGETNYADKFQGRVTF<br>TSDTSTSTAYMELRNLKSDDTAVYYCARWSWSDGYYVYFDYWGQGTTVTVSS |
| 163. | CD33_8 | VL | DIVMTQSPDSLSVSLGERTTINCKSSQSVLDSSTNKNSLAWYQQKPGQPPKLLLSWASTRESGIPDRFSG<br>SGSGTDFTLTIDSLQPEDSATYYCQQSAHFPITFGQGTRLEIK |

| SEQ ID NO: | Description | | SEQUENCE |
|---|---|---|---|
| 164. | CD33_8 | scFv | QVQLVQSGAEVKKPGESVKVSCKASGYTFTNYGMNWVKQAPGQGLEWMGWINTYTGETNYADKFQGRVTF TSDTSTSTAYMELRNLKSDDTAVYYCARWSWSDGYYVYFDYWGQGTTVTVSSGGGGSGGGGSGGGGSDIV MTQSPDSLSVSLGERTTINCKSSQSVLDSSTNKNSLAWYQQKPGQPPKLLLSWASTRESGIPDRFSGSGS GTDFTLTIDSLQPEDSATYYCQQSAHFPITFGQGTRLEIK |
| 165. | CD33_9 | VH CDR1 | NYGMN |
| 166. | CD33_9 | VH CDR2 | WINTYTGEPTYADKFQG |
| 167. | CD33_9 | VH CDR3 | WSWSDGYYVYFDY |
| 168. | CD33_9 | VL CDR1 | KSSQSVLDSSNNKNSLA |
| 169. | CD33_9 | VL CDR2 | WASTRES |
| 170. | CD33_9 | VL CDR3 | QQSAHFPIT |
| 171. | CD33_9 | VH | QVQLVQSGAEVKKPGESVKVSCKASGYTFTNYGMNWVKQAPGQGLEWMGWINTYTGEPTYADKFQGRVTM TTDTSTSTAYMEIRNLRSDDTAVYYCARWSWSDGYYVYFDYWGQGTTVTVSS |
| 172. | CD33_9 | VL | DIVMTQSPDSLTVSLGERTTINCKSSQSVLDSSNNKNSLAWYQQKPGQPPKLLLSWASTRESGIPDRFSG SGSGTDFTLTIDGLQPEDSATYYCQQSAHFPITFGQGTRLEIK |
| 173. | CD33_9 | scFv | QVQLVQSGAEVKKPGESVKVSCKASGYTFTNYGMNWVKQAPGQGLEWMGWINTYTGEPTYADKFQGRVTM TTDTSTSTAYMEIRNLRSDDTAVYYCARWSWSDGYYVYFDYWGQGTTVTVSSGGGGSGGGGSGGGGSDIV MTQSPDSLTVSLGERTTINCKSSQSVLDSSNNKNSLAWYQQKPGQPPKLLLSWASTRESGIPDRFSGSGS GTDFTLTIDGLQPEDSATYYCQQSAHFPITFGQGTRLEIK |
| 174. | CD19 | bi-specific molecule | DIQLTQSPASLAVSLGQRATISCKASQSVDYDGDSYLNWYQQIPGQPPKLLIYDASNLVSGIPPRFSGSGSGTDFTL NIHPVEKVDAATYHCQQSTEDPWTFGGGTKLEIKGGGGSGGGGSGGGGSQVQLQQSGAELVRPGSSVKISCKASGYA FSSYWMNWVKQRPGQGLEWIGQIWPGDGDTNYNGKFKGKATLTADESSSTAYMQLSSLASEDSAVYFCARRETTTVG RYYYAMDYWGQGTTVTVSSGGGGSDIKLQQSGAELARPGASVKMSCKTSGYTFTRYTMHWVKQRPGQGLEWIGYINP SRGYTNYNQKFKDKATLTTDKSSSTAYMQLSSLTSEDSAVYYCARYDDHYCLDYWGQGTTLTVSSVEGGSGGSGGS GGSGGVDDIQLTQSPAIMSASPGEKVTMTCRASSSVSYMNWYQQKSGTSPKRWIYDTSKVASGVPYRFSGSGSGTSY SLTISSMEAEDAATYYCQQWSSNPLTFGAGTKLELKHHHHHH |
| 175. | CD33_2 | bi-specific molecule + hALB | QVQLVQSGAEVKKPGESVKVSCKASGYTFTNYGMNWVKQAPGQCLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSLQPEDSATYYC QQSAHFPITFGCGTRLEIKSGGGGSEVQLVESGGGLVQPGGSLKLSCAASGFTFNKYAMNWVRQAPGKGLEWVARIR SKYNNYATYYADSVKDRFTISRDDSKNTAYLQMNNLKTEDTAVYYCVRHGNFGNSYISYWAYWGQGTLVTVSSGGGG SGGGGSGGGGSQTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVLPGGGGSDAHKSEVAHRFKDLGEENFKALVLIAFA QYLQQCPFEDHVKLVNEVTEFAKTCVADESAENCDKSLHTLFGDKLCTVATLRETYGEMADCCAKQEPERNECFLQH KDDNPNLPRLVRPEVDVMCTAFHDNEETFLKKYLYEIARRHPYFYAPELLFFAKRYKAAFTECCQAADKAACLLPKL DELRDEGKASSAKQRLKCASLQKFGERAFKAWAVARLSQRFPKAEFAEVSKLVTDLTKVHTECCHGDLLECADDRAD LAKYICENQDSISSKLKECCEKPLLEKSHCIAEVENDEMPADLPSLAADFVESKDVCKNYAEAKDVFLGMFLYEYAR RHPDYSVVLLLRLAKTYETTLEKCCAAADPHECYAKVFDEFKPLVEEPQNLIKQNCELFEQLGEYKFQNALLVRYTK KVPQVSTPTLVEVSRNLGKVGSKCCKHPEAKRMPCAEDYLSVVLNQLCVLHEKTPVSDRVTKCCTESLVNRRPCFSA LEVDETYVPKEFNAETFTFHADICTLSEKERQIKKQTALVELVKHKPKATKEQLKAVMDDFAAFVEKCCKADDKETC FAEEGKKLVAASQAALGLDYHHHHHH |
| 176. | MS_4 | bi-specific molecule + hALB | QVQLVESGGGLVKPGGSLRLSCAASGFTFSDYYMTWIRQAPGKGLEWLSYISSSGSTIYYADSVKGRFTISRDNAKN SLFLQMNSLRAEDTAVYYCARDRNSHFDYWGQGTLVTVSSGGGGSGGGGSGGGGSDIQMTQSPSSVSASVGDRVTIT CRASQGINTWLAWYQQKPGKAPKLLIYGASLQSGVPSRFSGSGSGTDFTLTISSLQPEDFATYYCQQAKSFPRTFG QGTKVEIKSGGGGSEVQLVESGGGLVQPGGSLKLSCAASGFTFNKYAMNWVRQAPGKGLEWVARIRSKYNNYATYYA DSVKDRFTISRDDSKNTAYLQMNNLKTEDTAVYYCVRHGNFGNSYISYWAYWGQGTLVTVSSGGGGSGGGGSGGGGS QTVVTQEPSLTVSPGGTVTLTCGSSTGAVTSGNYPNWVQQKPGQAPRGLIGGTKFLAPGTPARFSGSLLGGKAALTL SGVQPEDEAEYYCVLWYSNRWVFGGGTKLTVLPGGGGSDAHKSEVAHRFKDLGEENFKALVLIAFAQYLQQCPFEDH VKLVNEVTEFAKTCVADESAENCDKSLHTLFGDKLCTVATLRETYGEMADCCAKQEPERNECFLQHKDDNPNLPRLV RPEVDVMCTAFHDNEETFLKKYLYEIARRHPYFYAPELLFFAKRYKAAFTECCQAADKAACLLPKLDELRDEGKASS AKQRLKCASLQKFGERAFKAWAVARLSQRFPKAEFAEVSKLVTDLTKVHTECCHGDLLECADDRADLAKYICENQDS ISSKLKECCEKPLLEKSHCIAEVENDEMPADLPSLAADFVESKDVCKNYAEAKDVFLGMFLYEYARRHPDYSVVLLL RLAKTYETTLEKCCAAADPHECYAKVFDEFKPLVEEPQNLIKQNCELFEQLGEYKFQNALLVRYTKKVPQVSTPTLV EVSRNLGKVGSKCCKHPEAKRMPCAEDYLSVVLNQLCVLHEKTPVSDRVTKCCTESLVNRRPCFSALEVDETYVPKE FNAETFTFHADICTLSEKERQIKKQTALVELVKHKPKATKEQLKAVMDDFAAFVEKCCKADDKETCFAEEGKKLVAA SQAALGLDYHHHHHH |

| SEQ ID NO: | Description | | SEQUENCE |
|---|---|---|---|
| 177. | FAPa | bi-specific molecule | QVQLVQSGAEVKKPGASVKVSCKASGYTFTEYTIHWVRQAHGQSLEWMGGINPNNGIPNYNQKFKGRVTI TVDTSASTAYMELRSLRSEDTAVYYCARRRIAYGYDEGHAMDYWGQGTLVTVSSGGGGSGGGGSGGGGSD IVMTQTPFSLPVTPGEPASISCKSSQSLLYSRNQKNYLAWYQQKPGQSPKLLIYWASTRESGVPDRFSGS GSGTDFTLKISRVEAEDVGVYYCQQYFSYPLTFGGGTKVEIKSGGGGSEVQLVESGGGLVQPGGSLKLSC AASGFTFNKYAMNWVRQAPGKGLEWVARIRSKYNNYATYYADSVKDRFTISRDDSKNTAYLQMNNLKTED TAVYYCVRHGNFGNSYISYWAYWGQGTLVTVSSGGGGSGGGGSGGGGSQTVVTQEPSLTVSPGGTVTLTC GSSTGAVTSGNYPNWVQQKPGQAPRGLIGGTKFLAPGTPARFSGSLLGGKAALTLSGVQPEDEAEYYCVL WYSNRWVFGGGTKLTVLHHHHHH |
| 178. | G4S | linker | GGGS |
| 179. | F12q | scFv | EVQLVESGGGLVQPGGSLRLSCAASGFTFNSYAMNWVRQAPGKGLEWVARIRSKYNNYATYYADSVKGRFTISRDDS KNTAYLQMSLKTEDTAVYYCVRHGNFGNSYVSWWAYWGQGTLVTVSSGGGGSGGGGSGGGGSQTVVTQEPSLTVSP GGTVTLTCGSSTGAVTSGNYPNWVQQKPGQAPRGLIGGTKFLAPGTPARFSGSLLGGKAALTLSGVQPEDEAEYYCV LWYSNRWVFGGGTKLTVL |
| 180. | CD33-scFc BiTE antibody construct CD33_2-scFc | bi-specific HLE molecule | QVQLVQSGAEVKKPGESVKVSCKASGYTFTNYGMNWVKQAPGQCLEWMGWINTYTGEPTYADKFQGRVTMTTDTSTS TAYMEIRNLGGDDTAVYYCARWSWSDGYYVYFDYWGQGTSVTVSSGGGGSGGGGSGGGGSDIVMTQSPDSLTVSLGE RTTINCKSSQSVLDSSTNKNSLAWYQQKPGQPPKLLLSWASTRESGIPDRFSGSGSGTDFTLTIDSPQPEDSATYYC QQSAHFPITFGCGTRLEIKSGGGGSEVQLVESGGGLVQPGGSLKLSCAASGFTFNKYAMNWVRQAPGKGLEWVARIR SKYNNYATYYADSVKDRFTISRDDSKNTAYLQMNNLKTEDTAVYYCVRHGNFGNSYISYWAYWGQGTLVTVSSGGGG SGGGGSGGGGSQTVVTQEPSLTVSPGGTVTLTCGSSTGAVTSGNYPNWVQQKPGQAPRGLIGGTKFLAPGTPARFSG SLLGGKAALTLSGVQPEDEAEYYCVLWYSNRWVFGGGTKLTVLGGGGDKTHTCPPCPAPELLGGPSVFLFPPKPKDT LMISRTPEVTCVVVDVSHEDPEVKFNWYVDGVEVHNAKTKPCEEQYGSTYRCVSVLTVLHQDWLNGKEYKCKVSNKA LPAPIEKTISKAKGQPREPQVYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGKGGGGSGGGGSGGGGSGGGGSGGGGSGGGGSDKTH TCPPCPAPELLGGPSVFLFPPKPKDTLMISRTPEVTCVVVDVSHEDPEVKFNWYVDGVEVHNAKTKPCEEQYGSTYR CVSVLTVLHQDWLNGKEYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQKSLSLSPGK |
| 181. | FL1 | scFv | QVTLKESGPTLVKPTETLTLTCTLSGFSLNNARMGVSWIRQPPGKCLEWLAHIFSNDEKSYSTSLKNRLTISKDSSK TQVVLTMTNVDPVDTATYYCARIVGYGSGWYGFFDYWGQGTLVTVSSGGGGSGGGGSGGGGSDIQMTQSPSSLSASV GDRVTITCRASQGIRNDLGWYQQKPGKAPKRLIYAASTLQSGVPSRFSGSGSGTEFTLTISSLQPEDFATYYCLQHN SYPLTFGCGTKVEIK |
| 182. | FLT3-scFc BiTE antibody construct FL1-scFc | bi-specific HLE molecule | QVTLKESGPTLVKPTETLTLTCTLSGFSLNNARMGVSWIRQPPGKCLEWLAHIFSNDEKSYSTSLKNRLTISKDSSK TQVVLTMTNVDPVDTATYYCARIVGYGSGWYGFFDYWGQGTLVTVSSGGGGSGGGGSGGGGSDIQMTQSPSSLSASV GDRVTITCRASQGIRNDLGWYQQKPGKAPKRLIYAASTLQSGVPSRFSGSGSGTEFTLTISSLQPEDFATYYCLQHN SYPLTFGCGTKVEIKSGGGGSEVQLVESGGGLVQPGGSLKLSCAASGFTFNKYAMNWVRQAPGKGLEWVARIRSKYN NYATYYADSVKDRFTISRDDSKNTAYLQMNNLKTEDTAVYYCVRHGNFGNSYISYWAYWGQGTLVTVSSGGGGSGGG GSGGGGSQTVVTQEPSLTVSPGGTVTLTCGSSTGAVTSGNYPNWVQQKPGQAPRGLIGGTKFLAPGTPARFSGSLLG GKAALTLSGVQPEDEAEYYCVLWYSNRWVFGGGTKLTVLGGGGDKTHTCPPCPAPELLGGPSVFLFPPKPKDTLMIS RTPEVTCVVVDVSHEDPEVKFNWYVDGVEVHNAKTKPCEEQYGSTYRCVSVLTVLHQDWLNGKEYKCKVSNKALPAP IEKTISKAKGQPREPQVYTLPPSREEMTKNQVSLTCLVKGFYPSDIAVEWESNGQPENNYKTTPPVLDSDGSFFLYS KLTVDKSRWQQGNVFSCSVMHEALHNHYTQKSLSLSPGKGGGGSGGGGSGGGGSGGGGSGGGGSGGGGSDKTHTCPP CPAPELLGGPSVFLFPPKPKDTLMISRTPEVTCVVVDVSHEDPEVKFNWYVDGVEVHNAKTKPCEEQYGSTYRCVSV LTVLHQDWLNGKEYKCKVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSLSPGK |
| 183. | FL2 | scFv | QVTLKESGPALVKPTETLTLTCTLSGFSLNNARMAVSWIRQPPGKCLEWLAHIFSNDEKSYSTSLKSRLTISKDTSK SQVVLTMTNMDPEDTATYYCARIVGYGTGWYGFFDYWGQGILVTVSSGGGGSGGGGSGGGGSDIQMTQSPSSLSASV GDRVTITCRASQGIRNDLAWYQQKPGKAPKRLIYAASSLQSGVPSRFSGSGSGTEFTLTISSLQPEDFATYYCLQHN SYPLTFGCGTKVEIK |
| 184. | FLT3-scFc BiTE antibody construct FL2-scFc | bi-specific HLE molecule | QVTLKESGPALVKPTETLTLTCTLSGFSLNNARMAVSWIRQPPGKCLEWLAHIFSNDEKSYSTSLKSRLTISKDTSK SQVVLTMTNMDPEDTATYYCARIVGYGTGWYGFFDYWGQGILVTVSSGGGGSGGGGSGGGGSDIQMTQSPSSLSASV GDRVTITCRASQGIRNDLAWYQQKPGKAPKRLIYAASSLQSGVPSRFSGSGSGTEFTLTISSLQPEDFATYYCLQHN SYPLTFGCGTKVEIKSGGGGSEVQLVESGGGLVQPGGSLKLSCAASGFTFNKYAMNWVRQAPGKGLEWVARIRSKYN NYATYYADSVKDRFTISRDDSKNTAYLQMNNLKTEDTAVYYCVRHGNFGNSYISYWAYWGQGTLVTVSSGGGGSGGG GSGGGGSQTVVTQEPSLTVSPGGTVTLTCGSSTGAVTSGNYPNWVQQKPGQAPRGLIGGTKFLAPGTPARFSGSLLG GKAALTLSGVQPEDEAEYYCVLWYSNRWVFGGGTKLTVLGGGGDKTHTCPPCPAPELLGGPSVFLFPPKPKDTLMIS RTPEVTCVVVDVSHEDPEVKFNWYVDGVEVHNAKTKPCEEQYGSTYRCVSVLTVLHQDWLNGKEYKCKVSNKALPAP IEKTISKAKGQPREPQVYTLPPSREEMTKNQVSLTCLVKGFYPSDIAVEWESNGQPENNYKTTPPVLDSDGSFFLYS KLTVDKSRWQQGNVFSCSVMHEALHNHYTQKSLSLSPGKGGGGSGGGGSGGGGSGGGGSGGGGSGGGGSDKTHTCPP CPAPELLGGPSVFLFPPKPKDTLMISRTPEVTCVVVDVSHEDPEVKFNWYVDGVEVHNAKTKPCEEQYGSTYRCVSV LTVLHQDWLNGKEYKCKVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSLSPGK |
| 185. | BC1 | scFv | QVQLVQSGAEVKKPGASVKVSCKASGYTFTNHIIHWVRQAPGQCLEWMGYINPYPGYHAYNEKFQGRATMTSDTSTS TVYMELSSLRSEDTAVYYCARDGYYRDTDVLDYWGQGTLVTVSSGGGGSGGGGSGGGGSDIQMTQSPSSLSASVGDR VTITCQASQDISNYLNWYQQKPGKAPKLLIYYTSRLHTGVPSRFSGSGSGTDFTFTISSLEPEDIATYYCQQGNTLP WTFGCGTKLEIK |

| SEQ ID NO: | Description | | SEQUENCE |
|---|---|---|---|
| 186. | BCMA-scFc BiTE 1 anti-body construct BC1-scFc | bi-specific HLE molecule | QVQLVQSGAEVKKPGASVKVSCKASGYTFTNHIIHWVRQAPGQCLEWMGYINPYPGYHAYNEKFQGRATMTSDTSTS TVYMELSSLRSEDTAVYYCARDGYYRDTDVLDYWGQGTLVTVSSGGGGSGGGGSGGGGSDIQMTQSPSSLSASVGDR VTITCQASQDISNYLNWYQQKPGKAPKLLIYYTSRLHTGVPSRFSGSGSGTDFTFTISSLEPEDIATYYCQQGNTLP WTFGCGTKLEIKSGGGGSEVQLVESGGGLVQPGGSLKLSCAASGFTFNKYAMNWVRQAPGKGLEWVARIRSKYNNYA TYYADSVKDRFTISRDDSKNTAYLQMNNLKTEDTAVYYCVRHGNFGNSYISYWAYWGQGTLVTVSSGGGGSGGGGSG GGGSQTVVTQEPSLTVSPGGTVTLTCGSSTGAVTSGNYPNWVQQKPGQAPRGLIGGTKFLAPGTPARFSGSLLGGKA ALTLSGVQPEDEAEYYCVLWYSNRWVFGGGTKLTVLGGGGDKTHTCPPCPAPELLGGPSVFLFPPKPKDTLMISRTP EVTCVVVDVSHEDPEVKFNWYVDGVEVHNAKTKPCEEQYGSTYRCVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGKGGGGSGGGGSGGGGSGGGGSGGGGSDKTHTCPPCPA PELLGGPSVFLFPPKPKDTLMISRTPEVTCVVVDVSHEDPEVKFNWYVDGVEVHNAKTKPCEEQYGSTYRCVSVLTV LHQDWLNGKEYKCKVSNKALPAPIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 187. | BC2 | scFv | QVQLVQSGAEVKKPGASVKVSCKASGYTFTNHIIHWVRQAPGQCLEWMGYINPYPGYHAYNEKFQGRATMTSDTSTS TVYMELSSLRSEDTAVYYCARDGYYRDTDVLDYWGQGTLVTVSSGGGGSGGGGSGGGGSDIQMTQSPSSLSASVGDR VTITCQASQDISNYLNWYQQKPGKAPKLLIYYTSRLHTGVPSRFSGSGSGTDFTFTISSLEPEDIATYYCQQGNTLP WTFGQGTKLEIK |
| 188. | BCMA-scFc BiTE 2 anti-body construct BC2-scFc | bi-specific HLE molecule | QVQLVQSGAEVKKPGASVKVSCKASGYTFTNHIIHWVRQAPGQCLEWMGYINPYPGYHAYNEKFQGRATMTSDTSTS TVYMELSSLRSEDTAVYYCARDGYYRDTDVLDYWGQGTLVTVSSGGGGSGGGGSGGGGSDIQMTQSPSSLSASVGDR VTITCQASQDISNYLNWYQQKPGKAPKLLIYYTSRLHTGVPSRFSGSGSGTDFTFTISSLEPEDIATYYCQQGNTLP WTFGQGTKLEIKSGGGGSEVQLVESGGGLVQPGGSLKLSCAASGFTFNKYAMNWVRQAPGKGLEWVARIRSKYNNYA TYYADSVKDRFTISRDDSKNTAYLQMNNLKTEDTAVYYCVRHGNFGNSYISYWAYWGQGTLVTVSSGGGGSGGGGSG GGGSQTVVTQEPSLTVSPGGTVTLTCGSSTGAVTSGNYPNWVQQKPGQAPRGLIGGTKFLAPGTPARFSGSLLGGKA ALTLSGVQPEDEAEYYCVLWYSNRWVFGGGTKLTVLGGGGDKTHTCPPCPAPELLGGPSVFLFPPKPKDTLMISRTP EVTCVVVDVSHEDPEVKFNWYVDGVEVHNAKTKPCEEQYGSTYRCVSVLTVLHQDWLNGKEYKCKVSNKALPAPIEK TISKAKGQPREPQVYTLPPSREEMTKNQVSLTCLVKGFYPSDIAVEWESNGQPENNYKTTPPVLDSDGSFFLYSKLT VDKSRWQQGNVFSCSVMHEALHNHYTQKSLSLSPGKGGGGSGGGGSGGGGSGGGGSGGGGSDKTHTCPPCPA PELLGGPSVFLFPPKPKDTLMISRTPEVTCVVVDVSHEDPEVKFNWYVDGVEVHNAKTKPCEEQYGSTYRCVSVLTV LHQDWLNGKEYKCKVSNKALPAPIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKSLSLSPGK |

The invention claimed is:

1. A pharmaceutical composition comprising a bispecific single chain antibody construct that binds to a target cell surface antigen selected from CD19, CD33, FAPalpha, MSLN, FLT3 and BCMA via a first binding domain and to the T cell surface antigen CD3 via a second binding domain, a β-cyclodextrin and a buffer,
   wherein the binding domains have pairs of VH regions and VL regions in the format of a single chain antibody (scFv), and wherein the bispecific single chain antibody construct optionally comprises a domain for extending serum half-life which binds to Fc domains,
   wherein the composition is characterized by a reduction or prevention of the formation of protein aggregates (high molecular weight species (HMWS)), and
   wherein the β-cyclodextrin is not hydroxypropyl-β-cyclodextrin.

2. The composition according to claim 1, wherein the β-cyclodextrin is selected from the group consisting of β-cyclodextrin, methyl-β-cyclodextrin, hydroxyethyl-β-cyclodextrin, ethyl-β-cyclodextrin, butyl-β-cyclodextrin Succinyl-(2-hydroxypropyl)-β-cyclodextrin, heptakis(2,3,6-tri-O-methyl)-β-cyclodextrin, heptakis(2,3,6-tri-O-benzoyl)-β-cyclodextrin, β-cyclodextrin phosphate sodium salt, β-cyclodextrin sulphate sodium salt, triacetyl-β-cyclodextrin, heptakis(6-O-sulfo)-β-cyclodextrin heptasodium salt, carboxymethyl-β-cyclodextrin sodium salt, sulfobutylether-β-cyclodextrin sodium salt, and 6-O-p-toluenesulfonyl-β-cyclodextrin.

3. The composition according to claim 1, wherein the β-cyclodextrin is present in a concentration in the range of 0.1% to 20% (w/v).

4. The composition according to claim 1, wherein the β-cyclodextrin is sulfobutylether-β-cyclodextrin sodium salt.

5. The composition according to claim 1, wherein the bispecific single chain antibody construct is present in a concentration range of 0.1-5 mg/ml.

6. The composition according to claim 1, wherein the buffer is selected from the group consisting of potassium phosphate, acetic acid/sodium acetate, citric acid/sodium citrate, succinic acid/sodium succinate, tartaric acid/sodium tartrate, histidine/histidine HCl, glycine, Tris, glutamate, acetate and mixtures thereof.

7. The composition according to claim 6, wherein the buffer is selected from the group consisting of potassium phosphate, citric acid/sodium citrate, succinic acid, histidine, glutamate, acetate and combinations thereof.

8. The composition according to claim 1, wherein the pH of the composition is in the range of 4-7.5.

9. The composition according to claim 1, further comprising one or more excipients selected from the group consisting of sucrose, trehalose, mannitol, sorbitol, arginine, lysine, polysorbate 20, polysorbate 80, poloxamer 188, pluronic and combinations thereof.

10. The composition according to claim 1, further comprising one or more preservatives.

11. The composition according to claim 10, wherein the one or more preservative is selected from the group consisting of benzyl alcohol, chlorobutanol, phenol, meta-cresol, methylparaben, phenoxyethanol, propylparaben and thiomerosal.

12. The composition according to claim 1, wherein the first binding domain comprises the amino acid sequence selected from the group consisting of SEQ ID NO: 99, 109, 119, 128, 137, 146, 155, 164, 173, 183, 185 and 187, and the second binding domain comprises the amino acid sequence selected from the group consisting of SEQ ID NO: 9, 18, 27, 36, 45, 54, 63, 72, 81, 179 and 90.

13. The composition according to claim 12, wherein the composition is free of preservatives, wherein the first and second binding domains of the antibody comprise the amino acid sequence set forth in SEQ ID NO 100 or 110 and the antibody is present at a concentration of about 0.5 mg/ml, wherein the β-cyclodextrin is sulfobutylether-β-cyclodextrin sodium salt and is present at a concentration of about 1% (w/v), wherein the buffer is potassium phosphate and is present at a concentration of about 10 mM, and wherein the composition further comprises sucrose at a concentration of about 8% (w/v) and polysorbate 80 at a concentration of about 0.01% (w/v) at a pH of about 6.0.

14. The composition according to claim 3, wherein the β-cyclodextrin is present in a concentration in the range of 0.5% to 2% (w/v).

15. The composition according to claim 14, wherein the β-cyclodextrin is present in a concentration in the range of 0.8% to 1.5% (w/v).

16. The composition according to claim 5, wherein the bispecific single chain antibody construct is present in a concentration range of 0.2-2.5 mg/ml.

17. The composition according to claim 16, wherein the bispecific single chain antibody construct is present in a concentration range of 0.25-1.0 mg/ml.

18. The composition according to claim 1, wherein the amino acid sequence of the bispecific single chain antibody construct is SEQ ID NO: 174.

19. The composition according to claim 1, wherein the cyclodextrin is sulfobutylether-β-cyclodextrin sodium salt in a concentration of about 1% (w/v) and the buffer is potassium phosphate in concentration of about 10 mM, and wherein the composition further comprises mannitol in a concentration of about 42%, sucrose in a concentration of about 2% (w/v), and polysorbate 80 in concentration of about 0.01% (w/v) at a pH of about 6.0.

* * * * *